(12) United States Patent
Heinelt et al.

(10) Patent No.: US 7,868,003 B2
(45) Date of Patent: Jan. 11, 2011

(54) SUBSTITUTED 4-PHENYLTETRAHYDROISOQUINOLINES, PHARMACEUTICAL COMPOSITIONS COMPRISING THEM AND THERAPEUTIC METHODS FOR THEIR USE

(75) Inventors: Uwe Heinelt, Wiesbaden (DE); Hans-Jochen Lang, Hofheim (DE); Klaus Wirth, Kriftel (DE); Thomas Licher, Bad Soden (DE); Armin Hofmeister, Dexheim (DE)

(73) Assignee: Sanofi-Aventis, Paris (FR)

( * ) Notice: Subject to any disclaimer, the term of this patent is extended or adjusted under 35 U.S.C. 154(b) by 666 days.

(21) Appl. No.: 11/776,041

(22) Filed: Jul. 11, 2007

(65) Prior Publication Data

US 2008/0058328 A1 Mar. 6, 2008

Related U.S. Application Data

(63) Continuation of application No. PCT/EP2005/014127, filed on Dec. 30, 2005.

(30) Foreign Application Priority Data

Jan. 12, 2005 (DE) .................. 10 2005 001 411

(51) Int. Cl.
C07D 217/12 (2006.01)
A61K 31/47 (2006.01)

(52) U.S. Cl. .................. 514/235.2; 514/307; 544/128; 546/144

(58) Field of Classification Search .................. None
See application file for complete search history.

(56) References Cited

FOREIGN PATENT DOCUMENTS

| EP | 0825178 | 2/1998 |
|---|---|---|
| WO | WO 01/21582 | 3/2001 |
| WO | WO 01/32624 | 5/2001 |
| WO | WO 01/44164 | 6/2001 |
| WO | WO 01/72742 | 10/2001 |
| WO | WO 01/79186 | 10/2001 |
| WO | WO 03/048129 | 6/2003 |
| WO | WO 03/055880 | 7/2003 |
| WO | WO 2004/085404 | 10/2004 |

OTHER PUBLICATIONS

Akhter, S., et. al., Squalamine, a Novel Cationic Steroid, Specifically Inhibits the Brush-border Na+/H+ Exchanger Isoform NHE3, The American Physiological Society, 1999, c136-c144.
Ben-Ishai, D., et. al., Intra VS. Intermolecular Amidoalkylation of Aromatics, Tetrahedron vol. 43, No. 2, pp. 439-450 (1987).
Cuevas, et. al., alpha'-Silylated Tertiary Benzamides as Dual Ortho- and alpha'-Carbanion Synthons. , Tetrahedron Letters; 30;43;1989; pp. 5837-5840.
Fliegel, L., et. al., Regulation and Characterization of the Na+/H+ Exchanger, Biochem. Cell. Biol., 76: (1998), 735-741.
Johnson, P.D., et. al., Synthesis of N-Substituted 1,2,5-Thiadiazolidine and 1,2,6-Thiadiazinane 1,1-dioxides from Primary Amines, Tetrahedron Letters vol. 44, (2003), pp. 5483-5485.
Kano, S., et. al., A Synthesis of Simple 4,4-Disubstituted Tetrahydroisoquinolines by Cyclization of Alpha, Alpha-Disubstituted Phenylacetamides, Chem. Pham. Bull. 33(1) 340-346 (1985).
Klapars, A., et. al. , A General and Efficient Copperr Catalyst for the Amidation of Aryl Halides, J. Am. Chem. Soc. vol. 124, (2002) pp. 7421-7428.
Klapars, A., et. al., A General and Efficient Copper Catalyst for the Amidation of Aryl Halides and the N-Arylation of Nitrogen Heterocycles, J. Am. Chem. Soc., (2001) pp. 7727-7729 vol. 123.
Ma, E., et. al., Expression and Localization of Na+/H+ Exchangers in Rat Central Nervous System, Neuroscience vol. 79, No. 2, pp. 591-603 (1997).
Mederski, W. W. K. R., et. al., A Convenient Synthesis of 4-Aminoaryl Substituted Cyclic Imides, Tetrahedron Letters vol. 44, (2003) pp. 2133-2136.
Wang, J., et. al., Aminolysis of Esters or Lactones Promoted by NaHMDS-A General and Effecient Method for the Preparation of N-Aryl Amides, Synlett (2001) No. 9, pp. 1485-1487.
Zhao, X., et. al., A Practical Synthesis of 4-(3',4'-Dihydroxyphenyl)-1,2,3,4-tetrahydroisoquinoline, OPPI Briefs; 27;4;1995; pp. 513-516.

*Primary Examiner*—Zinna N Davis
(74) *Attorney, Agent, or Firm*—Jiang Lin

(57) ABSTRACT

The invention relates to substituted 4-phenyltetrahydroisoquinolines of formula I

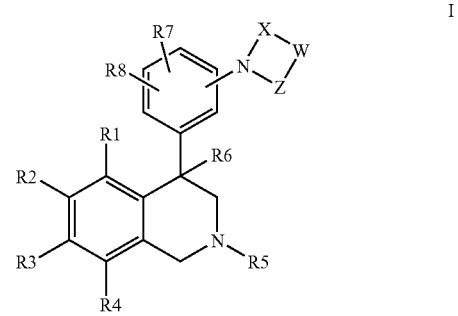

wherein R1-R8, N, W, X and Z are defined herein. These compounds and pharmaceutical compositions comprising them are useful in the treatment of respiratory disorders, sleep apnea, kidney disorders, high blood pressure, hypertension, disorders of the central nervous system and the like.

10 Claims, No Drawings

SUBSTITUTED 4-PHENYLTETRAHYDROISOQUINOLINES, PHARMACEUTICAL COMPOSITIONS COMPRISING THEM AND THERAPEUTIC METHODS FOR THEIR USE

CROSS-REFERENCE TO RELATED APPLICATIONS

This application is a continuation of International Patent Application No. PCT/EP2005/014127 filed on Dec. 30, 2005 which is incorporated herein by reference in its entirety which also claims the benefit of priority of German Patent Appln. No. 10/200,5001411.9 filed on Jan. 12, 2005.

FIELD OF THE INVENTION

The invention relates generally to pharmaceutical compositions useful in the prevention or treatment of respiratory disorders, sleep-related disorders, sleep apneas, snoring, acute and the like including related disorders of the central nervous system. More specifically, the present invention relates to a class of compounds known as tetrahydroisoquinolines which are inhibitors of the sodium-hydrogen exchanger (NHE), especially the sodium-hydrogen exchanger of the subtype 3 (NHE3) and therefore possess surprisingly effective therapeutic and pharmacological properties.

BACKGROUND OF THE INVENTION

It has been possible to show that compounds of the present invention are outstanding inhibitors of the sodium-hydrogen exchanger (NHE), especially the sodium-hydrogen exchanger of the subtype-3 (NHE-3).

The NHE-3 inhibitors known to date derive, for example, from compounds of the acylguanidine type (EP825178), norbornylamine type (WO0144164), 2-guanidino-quinazoline type (WO0179186) or benzamidine type (WO0121582, WO0172742). Squalamine, which has likewise been described as an NHE3 inhibitor (M. Donowitz et al., Am. J. Physiol. 276 (Cell Physiol. 45): C136-C144), according to the current state of knowledge, does not act immediately like the compounds of the formula I but rather via an indirect mechanism and thus attains its maximum intensity of action only after one hour.

Tetrahydroisoquinolines as inhibitors of the sodium-hydrogen exchanger of the subtype 3 (NHE3) have already been described in the patent application WO03048129, WO2004085404 and German application No. 102004046492.8. The patent application WO03055880 describes the related compound class of the tetrahydroisoquinolinium salts as NHE3 inhibitors. It has now been found that, surprisingly, the compounds of the formula I described here likewise constitute potent inhibitors of the NHE3 and have advantageous pharmacological and pharmacokinetic properties.

The NHE-3 is found in the body of various species, preferentially in the gall bladder, the intestines and in the kidneys (Larry Fliegel et al., Biochem. Cell. Biol. 76: 735-741, 1998), but has also been found in the brain (E. Ma et al., Neuroscience 79: 591-603).

Owing to their NHE-inhibitory properties, the compounds of the present invention are suitable for the prevention and treatment of disorders which are caused by an activation of or by an activated NHE, and also of disorders which have the NHE-related damage as a secondary cause.

The compounds of the invention can also be used for the treatment and prevention of disorders in which the NHE is only partially inhibited, for example by use of a lower dose.

The use of the inventive compounds relates to the prevention and to the treatment of acute and chronic disorders in veterinary and in human medicine.

As a consequence of their pharmacological actions, the compounds of the formula I are especially suitable for improving the respiratory drive. They can therefore be employed for the treatment of disturbed respiratory states, as can occur, for example, in the event of the following clinical states and disorders: disturbed central respiratory drive (for example central sleep apneas, sudden infant death, postoperative hypoxia), muscular-related respiratory disorders, respiratory disorders after long-term ventilation, respiratory disorders in the course of adaptation in high mountains, obstructive and mixed forms of sleep apneas, acute and chronic pulmonary disorders with hypoxia and hypercapnea.

SUMMARY OF THE INVENTION

The present invention relates to a class of compounds known as tetrahydroisoquinolines which are inhibitors of the sodium-hydrogen exchanger (NHE), especially the sodium-hydrogen exchanger of the subtype 3 (NHE3) and therefore possess surprisingly effective therapeutic and pharmacological properties. Specifically, the tetrahydroisoquinolines of the present invention are represented by the structure of formula I

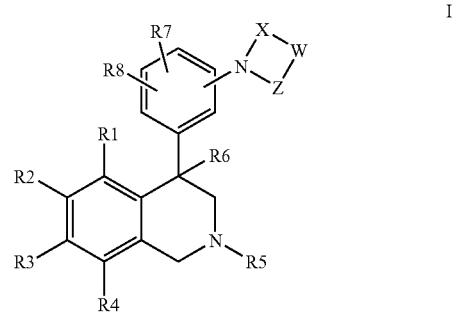

wherein R1-R8, N, X, W and Z are defined herein. These compounds exhibit protective action against pathological hypoxic and ischemic situations, and as a consequence of their ability to inhibit the cellular sodium/hydrogen proton ($Na^+/H^+$) exchange mechanism, these may be serve as medicaments for the treatment of all respiratory and sleep disorders, acute or chronic damage induced by ischemia or diseases induced primarily or secondarily thereby.

DETAILED DESCRIPTION OF THE INVENTION

The 4-phenyltetrahydroisoquinolines of the present invention are represented by the structure of formula I and are suitable for the prevention and treatment of respiratory and sleep related and central nervous system disorders as well as disorders which are caused by an activation of or by an activated NHE, and also of disorders which have the NHE-related damage as a secondary cause.

The present invention comprises compounds of the formula I

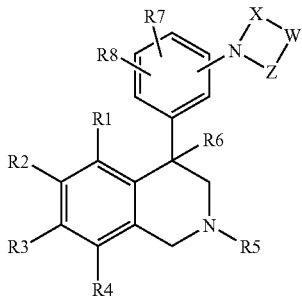

wherein:
R1, R2, R3 and R4
  are each independently hydrogen, F, Cl, Br, I, CN, $NO_2$ or R11-$(C_mH_{2m})$-$A_n$-;
  m is zero, 1, 2, 3 or 4;
  n is zero or 1;
  R11 is hydrogen, methyl or $C_pF_{2p+1}$;
  A is oxygen, NH, $N(CH_3)$ or $S(O)_q$;
    p is 1, 2 or 3;
    q is zero, 1 or 2;
R5 is hydrogen, alkyl having 1, 2, 3, 4, 5 or 6 carbon atoms or cycloalkyl having 3, 4, 5 or 6 carbon atoms;
R6 is hydrogen, OH, F, $CF_3$, alkyl having 1, 2, 3 or 4 carbon atoms or cycloalkyl having 3, 4, 5 or 6 carbon atoms;
R7 and R8
  are each independently hydrogen, F, Cl, Br, CN, $CO_2R12$, NR13R14 or R16-$(C_{mm}H_{2mm})$—$B_{nn}$—;
  R12 is hydrogen, alkyl having 1, 2, 3 or 4 carbon atoms or cycloalkyl having 3, 4, 5 or 6 carbon atoms;
  R13 and R14
    are each independently hydrogen, alkyl having 1, 2, 3 or 4 carbon atoms or cycloalkyl having 3, 4, 5 or 6 carbon atoms;
  or
  R13 and R14,
    with the nitrogen atom to which they are bonded, form a 4-, 5-, 6- or 7-membered ring in which one $CH_2$ group may be replaced by NR15, S or oxygen;
      R15 is hydrogen, alkyl having 1, 2, 3 or 4 carbon atoms or cycloalkyl having 3, 4, 5 or 6 carbon atoms;
    mm is zero, 1, 2, 3 or 4;
    nn is zero or 1;
    R16 is hydrogen, methyl or $C_{pp}F_{2pp+1}$;
    B is oxygen or $S(O)_{qq}$;
      pp is 1, 2 or 3;
      qq is zero, 1 or 2;
W is $C_rH_{2r}$ or $C_sH_{2s-2}$;
  where one or more $CH_2$ groups in $C_rH_{2r}$ and $C_sH_{2s-2}$ may be replaced by NR17, oxygen or S;
  R17 is hydrogen, alkyl having 1, 2, 3 or 4 carbon atoms or cycloalkyl having 3, 4, 5 or 6 carbon atoms;
  r is 1, 2, 3, 4, 5, 6, 7 or 8;
  s is 2, 3, 4, 5, 6, 7 or 8;
X is —C(O)— or —S(O)$_2$—;
Z is —C(O)— or a bond;

and also their pharmaceutically acceptable salts and trifluoroacetates.

In one embodiment, preference is given to compounds of the formula I in which
R1, R2, R3 and R4
  are each independently hydrogen, F, Cl, Br, CN or R11-$(C_mH_{2m})$-$A_n$-;
  m is zero or 1;
  n is zero or 1;
  R11 is hydrogen, methyl or $C_pF_{2p+1}$;
  A is oxygen, $NCH_3$ or $S(O)_q$;
    p is 1 or 2;
    q is zero, 1 or 2;
R5 is hydrogen, methyl, ethyl or cyclopropyl;
R6 is hydrogen or methyl;
R7 and R8
  are each independently hydrogen, F, Cl, CN, $CO_2R12$, NR13R14 or R16-$(C_{mm}H_{2mm})$—$B_{nn}$—;
  R12 is hydrogen, methyl or ethyl;
  R13 and R14
    are each independently hydrogen, alkyl having 1, 2, 3 or 4 carbon atoms or cycloalkyl having 3, 4, 5 or 6 carbon atoms;
  or
  R13 and R14,
    with the nitrogen atom to which they are bonded, form a 5-, 6- or 7-membered ring in which one $CH_2$ group may be replaced by NR15, S or oxygen;
      R15 is hydrogen, alkyl having 1, 2, 3 or 4 carbon atoms or cycloalkyl having 3, 4, 5 or 6 carbon atoms;
    mm is zero, 1 or 2;
    nn is zero or 1;
    R16 is hydrogen, methyl or $C_{pp}F_{2pp+1}$;
    B is oxygen or $S(O)_{qq}$;
      pp is 1 or 2;
      qq is zero, 1 or 2;
W is $C_rH_{2r}$ or $C_sH_{2s-2}$;
  where one or more $CH_2$ groups in $C_rH_{2r}$ and $C_sH_{2s-2}$ may be replaced by NR17, oxygen or S;
  R17 is hydrogen, alkyl having 1, 2, 3 or 4 carbon atoms or cycloalkyl having 3, 4, 5 or 6 carbon atoms;
  r is 2, 3, 4, 5, 6, 7 or 8;
  s is 2, 3, 4, 5, 6, 7 or 8;
X is —C(O)— or —S(O)$_2$—;
Z is —C(O)—;

and also their pharmaceutically acceptable salts and trifluoroacetates.

Particular preference is given to compounds of the formula I in which
R1 and R3
  are each hydrogen;
R2 and R4
  are each independently hydrogen, F, Cl, Br, $NH_2$, $NHCH_3$ or $N(CH_3)_2$;
R5 is hydrogen, methyl, ethyl or cyclopropyl;
R6 is hydrogen or methyl;
R7 and R8
  are each hydrogen;
W is $C_rH_{2r}$ or $C_sH_{2s-2}$;
  where one or more $CH_2$ groups in $C_rH_{2r}$ and $C_sH_{2s-2}$ may be replaced by NR17, oxygen or S;
  R17 is hydrogen or methyl;
  r is 2, 3, 4, 5 or 6;
  s is 2, 3, 4, 5 or 6;
X is —C(O)— or —S(O)$_2$—;
Z is —C(O)—;

and also their pharmaceutically acceptable salts and trifluoroacetates.

In a further embodiment, preference is given to compounds of the formula I in which R1 and R3
  are each hydrogen;
R2 and R4
  are each independently hydrogen, F, Cl, NH$_2$, NHCH$_3$ or N(CH$_3$)$_2$;
R5 is hydrogen, methyl, ethyl or cyclopropyl;
R6 is hydrogen or methyl;
R7 and R8
  are each hydrogen;
W is C$_r$H$_{2r}$ or C$_s$H$_{2s-2}$;
  where one or more CH$_2$ groups in C$_r$H$_{2r}$ and C$_s$H$_{2s-2}$ may be replaced by NR17, oxygen or S;
  R17 is hydrogen or methyl;
  r is 2, 3, 4, 5 or 6;
  s is 2, 3, 4, 5 or 6;
X is —C(O)— or —S(O)$_2$—;
Z is —C(O)—;

and also their pharmaceutically acceptable salts and trifluoroacetates.

Very particularly preferred are compounds of the formula I selected from the group of:

1-[2-(8-bromo-6-chloro-2-methyl-1,2,3,4-tetrahydroisoquinolin-4-yl)phenyl]pyrrolidine-2,5-dione,
3-[2-((R)-6,8-dichloro-2-cyclopropyl-1,2,3,4-tetrahydroisoquinolin-4-yl)phenyl]-1-methylimidazolidine-2,4-dione,
3-[2-((R)-6,8-dichloro-2-methyl-1,2,3,4-tetrahydroisoquinolin-4-yl)phenyl]-1-methyl-imidazolidine-2,4-dione
3-[2-((R)-6,8-dichloro-2-cyclopropyl-1,2,3,4-tetrahydroisoquinolin-4-yl)phenyl]-imidazolidine-2,4-dione
(S)-1-[2-((R)-6,8-dichloro-2-cyclopropyl-1,2,3,4-tetrahydroisochinolin-4-yl)phenyl]-3-hydroxypyrrolidine-2,5-dione,
(R)-1-[2-((R)-6,8-dichloro-2-cyclopropyl-1,2,3,4-tetrahydroisoquinolin-4-yl)phenyl]-3-hydroxypyrrolidine-2,5-dione,
(R)-1-[2-((R)-6,8-dichloro-2-methyl-1,2,3,4-tetrahydroisoquinolin-4-yl)phenyl]-3-hydroxypyrrolidine-2,5-dione,
(S)-1-[2-((R)-6,8-dichloro-2-methyl-1,2,3,4-tetrahydroisoquinolin-4-yl)phenyl]-3-hydroxypyrrolidine-2,5-dione,
4-[2-((R)-6,8-dichloro-2-methyl-1,2,3,4-tetrahydroisoquinolin-4-yl)phenyl]morpholine-3,5-dione,
3-[2-((R)-6,8-dichloro-2-methyl-1,2,3,4-tetrahydroisoquinolin-4-yl)phenyl]oxazolidine-2,4-dione,
3-[2-((R)-6,8-dichloro-2-methyl-1,2,3,4-tetrahydroisoquinolin-4-yl)phenyl]thiazolidine-2,4-dione,
1-[2-((R)-6,8-dichloro-2-cyclopropyl-1,2,3,4-tetrahydroisoquinolin-4-yl)phenyl]-pyrrolidine-2,5-dione,
(S)-1-[2-((R)-6,8-dichloro-2-methyl-1,2,3,4-tetrahydroisoquinolin-4-yl)phenyl]-3-methyl-piperidine-2,6-dione,
(R)-1-[2-((R)-6,8-dichloro-2-methyl-1,2,3,4-tetrahydroisoquinolin-4-yl)phenyl]-3-methyl-piperidine-2,6-dione,
1-[2-((R)-6,8-dichloro-2-methyl-1,2,3,4-tetrahydroisoquinolin-4-yl)phenyl]-3,5-dimethyl-piperidine-2,6-dione,
1-[2-((R)-6,8-dichloro-2-methyl-1,2,3,4-tetrahydroisoquinolin-4-yl)phenyl]-3-methyl-pyrrolidine-2,5-dione,
1-[2-((R)-6,8-dichloro-2-methyl-1,2,3,4-tetrahydroisoquinolin-4-yl)phenyl]-3,3-dimethyl-pyrrolidine-2,5-dione,
1-[2-(6,8-dichloro-2-cyclopropyl-1,2,3,4-tetrahydroisoquinolin-4-yl)phenyl]pyrrolidine-2,5-dione,
1-[4-((S)-6,8-dichloro-2-methyl-1,2,3,4-tetrahydroisoquinolin-4-yl)phenyl]piperidine-2,6-dione,
1-[4-((S)-6,8-dichloro-2-methyl-1,2,3,4-tetrahydroisoquinolin-4-yl)phenyl]pyrrolidine-2,5-dione,
1-[4-(6,8-dichloro-2-methyl-1,2,3,4-tetrahydroisoquinolin-4-yl)phenyl]pyrrolidine-2,5-dione,
1-[2-((R)-6,8-dichloro-2-methyl-1,2,3,4-tetrahydroisoquinolin-4-yl)phenyl]piperidine-2,6-dione,
1-[2-(6,8-dichloro-2-methyl-1,2,3,4-tetrahydroisoquinolin-4-yl)phenyl]piperidine-2,6-dione,
1-[3-((S)-6,8-dichloro-2-methyl-1,2,3,4-tetrahydroisoquinolin-4-yl)phenyl]pyrrole-2,5-dione,
1-[2-(6,8-dichloro-2-methyl-1,2,3,4-tetrahydroisoquinolin-4-yl)phenyl]pyrrolidine-2,5-dione,
1-[2-((R)-6,8-dichloro-2-methyl-1,2,3,4-tetrahydroisoquinolin-4-yl)phenyl]pyrrolidine-2,5-dione,
3-[2-((R)-6,8-dichloro-2-methyl-1,2,3,4-tetrahydroisoquinolin-4-yl)phenyl]imidazolidine-2,4-dione,
3-[2-(6,8-dichloro-2-methyl-1,2,3,4-tetrahydroisoquinolin-4-yl)phenyl]imidazolidine-2,4-dione,
3-[3-((S)-6,8-dichloro-2-methyl-1,2,3,4-tetrahydroisoquinolin-4-yl)phenyl]imidazolidine-2,4-dione,
3-[4-((S)-6,8-dichloro-2-methyl-1,2,3,4-tetrahydroisoquinolin-4-yl)phenyl]imidazolidine-2,4-dione,
3-[4-(6,8-dichloro-2-methyl-1,2,3,4-tetrahydroisoquinolin-4-yl)phenyl]imidazolidine-2,4-dione,
3-[2-((R)-6,8-dichloro-2-cyclopropyl-1,2,3,4-tetrahydroisoquinolin-4-yl)phenyl]-oxazolidine-2,4-dione,
3-[2-((R)-6,8-dichloro-2-methyl-1,2,3,4-tetrahydroisoquinolin-4-yl)phenyl]-5-methyl-imidazolidine-2,4-dione,
(3R,4S)-1-[2-((R)-6,8-dichloro-2-methyl-1,2,3,4-tetrahydroisoquinolin-4-yl)phenyl]-3,4-dimethylpyrrolidine-2,5-dione,
1-[4-((S)-6,8-dichloro-2-methyl-1,2,3,4-tetrahydroisoquinolin-4-yl)phenyl]-pyrrole-2,5-dione,
1-[3-((S)-6,8-dichloro-2-methyl-1,2,3,4-tetrahydroisoquinolin-4-yl)phenyl]piperidine-2,6-dione,
1-[3-((S)-6,8-dichloro-2-methyl-1,2,3,4-tetrahydroisoquinolin-4-yl)phenyl]pyrrolidine-2,5-dione,
1-[4-(6,8-dichloro-2-methyl-1,2,3,4-tetrahydroisoquinolin-4-yl)phenyl]piperidine-2,6-dione,
3-[3-(6,8-dichloro-2-methyl-1,2,3,4-tetrahydroisoquinolin-4-yl)phenyl]imidazolidine-2,4-dione,
1-[2-((R)-2-methyl-1,2,3,4-tetrahydroisoquinolin-4-yl)phenyl]pyrrolidine-2,5-dione,
3-[2-((R)-6,8-dichloro-2-methyl-1,2,3,4-tetrahydroisoquinolin-4-yl)phenyl]-5-isopropyl-imidazolidine-2,4-dione,
3-[2-((R)-6,8-dichloro-2-methyl-1,2,3,4-tetrahydroisoquinolin-4-yl)phenyl]-5-isobutyl-imidazolidine-2,4-dione,
(R and S)-3-[2-((R)-6,8-dichloro-2-methyl-1,2,3,4-tetrahydroisoquinolin-4-yl)phenyl]-5-(2-methylsulfanylethyl)imidazolidine-2,4-dione,
3-[2-((R)-6,8-dichloro-2-methyl-1,2,3,4-tetrahydroisoquinolin-4-yl)phenyl]-5,5-dimethyl-imidazolidine-2,4-dione,
1-[2-((R)-6,8-dichloro-1,2,3,4-tetrahydroisoquinolin-4-yl)phenyl]pyrrolidine-2,5-dione,
3-[2-((R)-6,8-dichloro-2-cyclopropyl-1,2,3,4-tetrahydroisoquinolin-4-yl)phenyl]-thiazolidine-2,4-dione,
1-[2-((S)-6,8-dichloro-2-methyl-1,2,3,4-tetrahydroisoquinolin-4-yl)phenyl]pyrrolidine-2,5-dione,
1-[2-((S)-6,8-dichloro-2-cyclopropyl-1,2,3,4-tetrahydroisoquinolin-4-yl)-phenyl]-pyrrolidine-2,5-dione,
1-[2-((R)-6,8-dichloro-2-methyl-1,2,3,4-tetrahydroisoquinolin-4-yl)phenyl]-3,3,4,4-tetra-methylpyrrolidine-2,5-dione,
(S)-1-[2-((R)-6,8-dichloro-2-cyclopropyl-1,2,3,4-tetrahydroisoquinolin-4-yl)phenyl]-3-methylpiperidine-2,6-dione, 1-[4-(6,8-dichloro-2-methyl-1,2,3,4-tetrahydroisoquinolin-4-yl)phenyl]-4,4-dimethyl-piperidine-2,6-dione
and 1-[2-(6,8-dichloro-2-methyl-1,2,3,4-tetrahydroisoquinolin-4-yl)phenyl]pyrrole-2,5-dione, and also its pharmaceutically acceptable salts and trifluoroacetates.

Especially preferred are compounds of the formula I selected from the group of

1-[2-(8-bromo-6-chloro-2-methyl-1,2,3,4-tetrahydroisoquinolin-4-yl)phenyl]pyrrolidine-2,5-dione,
3-[2-((R)-6,8-dichloro-2-cyclopropyl-1,2,3,4-tetrahydroisoquinolin-4-yl)phenyl]-1-methyl-imidazolidine-2,4-dione,
3-[2-((R)-6,8-dichloro-2-methyl-1,2,3,4-tetrahydroisoquinolin-4-yl)phenyl]-1-methyl-imidazolidine-2,4-dione
3-[2-((R)-6,8-dichloro-2-cyclopropyl-1,2,3,4-tetrahydroisoquinolin-4-yl)phenyl]-imidazolidine-2,4-dione
(S)-1-[2-((R)-6,8-dichloro-2-cyclopropyl-1,2,3,4-tetrahydroisoquinolin-4-yl)phenyl]-3-hydroxypyrrolidine-2,5-dione,
(R)-1-[2-((R)-6,8-dichloro-2-cyclopropyl-1,2,3,4-tetrahydroisoquinolin-4-yl)phenyl]-3-hydroxypyrrolidine-2,5-dione,
(R)-1-[2-((R)-6,8-dichloro-2-methyl-1,2,3,4-tetrahydroisoquinolin-4-yl)phenyl]-3-hydroxypyrrolidine-2,5-dione,
(S)-1-[2-((R)-6,8-dichloro-2-methyl-1,2,3,4-tetrahydroisoquinolin-4-yl)phenyl]-3-hydroxypyrrolidin-2,5-dione,
4-[2-((R)-6,8-dichloro-2-methyl-1,2,3,4-tetrahydroisoquinolin-4-yl)phenyl]morpholine-3,5-dione,
3-[2-((R)-6,8-dichloro-2-methyl-1,2,3,4-tetrahydroisoquinolin-4-yl)phenyl]oxazolidine-2,4-dione,
3-[2-((R)-6,8-dichloro-2-methyl-1,2,3,4-tetrahydroisoquinolin-4-yl)phenyl]thiazolidine-2,4-dione,
1-[2-((R)-6,8-dichloro-2-cyclopropyl-1,2,3,4-tetrahydroisoquinolin-4-yl)phenyl]-pyrrolidine-2,5-dione,
(S)-1-[2-((R)-6,8-dichloro-2-methyl-1,2,3,4-tetrahydroisoquinolin-4-yl)phenyl]-3-methyl-piperidine-2,6-dione,
(R)-1-[2-((R)-6,8-dichloro-2-methyl-1,2,3,4-tetrahydroisoquinolin-4-yl)phenyl]-3-methyl-piperidine-2,6-dione,
1-[2-((R)-6,8-dichloro-2-methyl-1,2,3,4-tetrahydroisoquinolin-4-yl)phenyl]-3,5-dimethyl-piperidine-2,6-dione,
1-[2-((R)-6,8-dichloro-2-methyl-1,2,3,4-tetrahydroisoquinolin-4-yl)phenyl]-3-methyl-pyrrolidine-2,5-dione,
1-[2-((R)-6,8-dichloro-2-methyl-1,2,3,4-tetrahydroisoquinolin-4-yl)phenyl]-3,3-dimethyl-pyrrolidine-2,5-dione,
1-[2-(6,8-dichloro-2-cyclopropyl-1,2,3,4-tetrahydroisoquinolin-4-yl)phenyl]pyrrolidine-2,5-dione,
1-[4-((S)-6,8-dichloro-2-methyl-1,2,3,4-tetrahydroisoquinolin-4-yl)phenyl]piperidine-2,6-dione,
1-[4-((S)-6,8-dichloro-2-methyl-1,2,3,4-tetrahydroisoquinolin-4-yl)phenyl]pyrrolidine-2,5-dione,
1-[4-(6,8-dichloro-2-methyl-1,2,3,4-tetrahydroisoquinolin-4-yl)phenyl]pyrrolidine-2,5-dione,
1-[2-((R)-6,8-dichloro-2-methyl-1,2,3,4-tetrahydroisoquinolin-4-yl)phenyl]piperidine-2,6-dione,
1-[2-(6,8-dichloro-2-methyl-1,2,3,4-tetrahydroisoquinolin-4-yl)phenyl]piperidine-2,6-dione,
1-[3-((S)-6,8-dichloro-2-methyl-1,2,3,4-tetrahydroisoquinolin-4-yl)phenyl]pyrrole-2,5-dione,
1-[2-(6,8-dichloro-2-methyl-1,2,3,4-tetrahydroisoquinolin-4-yl)phenyl]pyrrolidine-2,5-dione,
1-[2-((R)-6,8-dichloro-2-methyl-1,2,3,4-tetrahydroisoquinolin-4-yl)phenyl]pyrrolidine-2,5-dione,
3-[2-((R)-6,8-dichloro-2-methyl-1,2,3,4-tetrahydroisoquinolin-4-yl)phenyl]imidazolidine-2,4-dione,
3-[2-(6,8-dichloro-2-methyl-1,2,3,4-tetrahydroisoquinolin-4-yl)phenyl]imidazolidine-2,4-dione,
3-[3-((S)-6,8-dichloro-2-methyl-1,2,3,4-tetrahydroisoquinolin-4-yl)phenyl]imidazolidine-2,4-dione,
3-[4-((S)-6,8-dichloro-2-methyl-1,2,3,4-tetrahydroisoquinolin-4-yl)phenyl]imidazolidine-2,4-dione,
3-[4-(6,8-dichloro-2-methyl-1,2,3,4-tetrahydroisoquinolin-4-yl)phenyl]imidazolidine-2,4-dione,
3-[2-((R)-6,8-dichloro-2-cyclopropyl-1,2,3,4-tetrahydroisoquinolin-4-yl)phenyl]-oxazolidine-2,4-dione,
3-[2-((R)-6,8-dichlor-2-methyl-1,2,3,4-tetrahydroquinolin-4-yl)-phenyl]-5-methyl-imidazolidine-2,4-dione,
(3R,4S)-1-[2-((R)-6,8-dichlor-2-methyl-1,2,3,4-tetrahydroquinolin-4-yl)-phenyl]-3,4-dimethyl-pyrrolidine-2,5-dione,
1-[4-((S)-6,8-dichlor-2-methyl-1,2,3,4-tetrahydroquinolin-4-yl)-phenyl]-pyrrole-2,5-dione,
1-[3-((S)-6,8-dichlor-2-methyl-1,2,3,4-tetrahydroquinolin-4-yl)-phenyl]-piperidine-2,6-dione,
1-[3-((S)-6,8-dichlor-2-methyl-1,2,3,4-tetrahydroquinolin-4-yl)-phenyl]-pyrrolidine-2,5-dione,
1-[4-(6,8-dichlor-2-methyl-1,2,3,4-tetrahydroquinolin-4-yl)-phenyl]-piperidine-2,6-dione and
3-[3-(6,8-dichlor-2-methyl-1,2,3,4-tetrahydroquinolin-4-yl)-phenyl]-imidazolidine-2,4-dione, and also their pharmaceutically acceptable salts and trifluoroacetates.

Particularly preferred are compounds of the formula I selected from the group of:

1-[2-(8-bromo-6-chloro-2-methyl-1,2,3,4-tetrahydroisoquinolin-4-yl)phenyl]pyrrolidine-2,5-dione,
3-[2-((R)-6,8-dichloro-2-cyclopropyl-1,2,3,4-tetrahydroisoquinolin-4-yl)phenyl]-1-methylimidazolidine-2,4-dione,
3-[2-((R)-6,8-dichloro-2-methyl-1,2,3,4-tetrahydroisoquinolin-4-yl)phenyl]-1-methyl-imidazolidine-2,4-dione
3-[2-((R)-6,8-dichloro-2-cyclopropyl-1,2,3,4-tetrahydroisoquinolin-4-yl)phenyl]-imidazolidine-2,4-dione
(S)-1-[2-((R)-6,8-dichloro-2-cyclopropyl-1,2,3,4-tetrahydroisoquinolin-4-yl)phenyl]-3-hydroxypyrrolidine-2,5-dione,
(R)-1-[2-((R)-6,8-dichloro-2-cyclopropyl-1,2,3,4-tetrahydroisoquinolin-4-yl)phenyl]-3-hydroxypyrrolidine-2,5-dione,
(R)-1-[2-((R)-6,8-dichloro-2-methyl-1,2,3,4-tetrahydroisoquinolin-4-yl)phenyl]-3-hydroxypyrrolidine-2,5-dione,
(S)-1-[2-((R)-6,8-dichloro-2-methyl-1,2,3,4-tetrahydroisoquinolin-4-yl)phenyl]-3-hydroxypyrrolidine-2,5-dione,
4-[2-((R)-6,8-dichloro-2-methyl-1,2,3,4-tetrahydroisoquinolin-4-yl)phenyl]morpholine-3,5-dione,
3-[2-((R)-6,8-dichloro-2-methyl-1,2,3,4-tetrahydroisoquinolin-4-yl)phenyl]oxazolidine-2,4-dione,
3-[2-((R)-6,8-dichloro-2-methyl-1,2,3,4-tetrahydroisoquinolin-4-yl)phenyl]thiazolidine-2,4-dione,
1-[2-((R)-6,8-dichloro-2-cyclopropyl-1,2,3,4-tetrahydroisoquinolin-4-yl)phenyl]-pyrrolidine-2,5-dione,
(S)-1-[2-((R)-6,8-dichloro-2-methyl-1,2,3,4-tetrahydroisoquinolin-4-yl)phenyl]-3-methyl-piperidine-2,6-dione,
(R)-1-[2-((R)-6,8-dichloro-2-methyl-1,2,3,4-tetrahydroisoquinolin-4-yl)phenyl]-3-methyl-piperidine-2,6-dione,
1-[2-((R)-6,8-dichloro-2-methyl-1,2,3,4-tetrahydroisoquinolin-4-yl)phenyl]-3,5-dimethyl-piperidine-2,6-dione,
1-[2-((R)-6,8-dichloro-2-methyl-1,2,3,4-tetrahydroisoquinolin-4-yl)phenyl]-3-methyl-pyrrolidine-2,5-dione,
1-[2-((R)-6,8-dichloro-2-methyl-1,2,3,4-tetrahydroisoquinolin-4-yl)phenyl]-3,3-dimethyl-pyrrolidine-2,5-dione, 1-[2-(6,8-dichloro-2-cyclopropyl-1,2,3,4-tetrahydroiso-quinolin-4-yl)phenyl]pyrrolidine-2,5-dione,
1-[4-((S)-6,8-dichloro-2-methyl-1,2,3,4-tetrahydroiso-quinolin-4-yl)phenyl]piperidine-2,6-dione,
1-[4-((S)-6,8-dichloro-2-methyl-1,2,3,4-tetrahydroiso-quinolin-4-yl)phenyl]pyrrolidine-2,5-dione,
1-[4-(6,8-dichloro-2-methyl-1,2,3,4-tetrahydroisoquinolin-4-yl)phenyl]pyrrolidine-2,5-dione,
1-[2-((R)-6,8-dichloro-2-methyl-1,2,3,4-tetrahydroiso-quinolin-4-yl)phenyl]piperidine-2,6-dione,
1-[2-(6,8-dichloro-2-methyl-1,2,3,4-tetrahydroisoquinolin-4-yl)phenyl]piperidine-2,6-dione,
1-[3-((S)-6,8-dichloro-2-methyl-1,2,3,4-tetrahydroiso-quinolin-4-yl)phenyl]pyrrole-2,5-dione,
1-[2-(6,8-dichloro-2-methyl-1,2,3,4-tetrahydroisoquinolin-4-yl)phenyl]pyrrolidine-2,5-dione,
1-[2-((R)-6,8-dichloro-2-methyl-1,2,3,4-tetrahydroiso-quinolin-4-yl)phenyl]pyrrolidine-2,5-dione,
3-[2-((R)-6,8-dichloro-2-methyl-1,2,3,4-tetrahydroiso-quinolin-4-yl)phenyl]imidazolidine-2,4-dione,
3-[2-(6,8-dichloro-2-methyl-1,2,3,4-tetrahydroisoquinolin-4-yl)phenyl]imidazolidine-2,4-dione,
3-[3-((S)-6,8-dichloro-2-methyl-1,2,3,4-tetrahydroiso-quinolin-4-yl)phenyl]imidazol idine-2,4-dione,
3-[4-((S)-6,8-dichloro-2-methyl-1,2,3,4-tetrahydroiso-quinolin-4-yl)phenyl]imidazolidine-2,4-dione,
3-[4-(6,8-dichloro-2-methyl-1,2,3,4-tetrahydroisoquinolin-4-yl)phenyl]imidazolidine-2,4-dione and 3-[2-((R)-6,8-dichloro-2-cyclopropyl-1,2,3,4-tetrahydroiso-quinolin-4-yl)phenyl]-oxazolidine-2,4-dione, and also their pharmaceutically acceptable salts and trifluoroacetates.

A further embodiment encompasses compounds of the formula I in which
R1, R2, R3 and R4
 are each independently hydrogen, F, Cl, Br, CN or R11-$(C_mH_{2m})$-$A_n$-;
  m is zero or 1;
  n is zero or 1;
  R11 is hydrogen, methyl or $C_pF_{2p+1}$;
  A is oxygen, $NCH_3$ or $S(O)_q$;
   p is 1 or 2;
   q is zero, 1 or 2;
R5 is hydrogen, methyl, ethyl or cyclopropyl;
R6 is hydrogen or methyl;
R7 and R8
 are each independently hydrogen, F, Cl, CN, $CO_2R12$, NR13R14 or R16-$(C_{mm}H_{2mm})$—$B_{nn}$—;
  R12 is hydrogen, methyl or ethyl;
  R13, R14 are each independently hydrogen, alkyl having 1, 2, 3 or 4 carbon atoms or cycloalkyl having 3, 4, 5 or 6 carbon atoms;
  or
  R13 and R14,
   with the nitrogen atom to which they are bonded, form a 5-, 6- or 7-membered ring in which one $CH_2$ group may be replaced by NR15, S or oxygen;
    R15 is hydrogen, alkyl having 1, 2, 3 or 4 carbon atoms or cycloalkyl having 3, 4, 5 or 6 carbon atoms;
  mm is zero, 1 or 2;
  nn is zero or 1;
  R16 is hydrogen, methyl or $C_{pp}F_{2pp+1}$;
  B is oxygen or $S(O)_{qq}$;
   pp is 1 or 2;
   qq is zero, 1 or 2;
W is $C_rH_{2r}$ or $C_sH_{2s-2}$;
 where one or more $CH_2$ groups in $C_rH_{2r}$ and $C_sH_{2s-2}$ may be replaced by NR17, oxygen or S;
  R17 is hydrogen, alkyl having 1, 2, 3 or 4 carbon atoms or cycloalkyl having 3, 4, 5 or 6 carbon atoms;
  r is 1, 2, 3, 4, 5, 6, 7 or 8;
  s is 2, 3, 4, 5, 6, 7 or 8;
X is —C(O)— or —S(O)$_2$—;
Z is a bond;

and also their pharmaceutically acceptable salts and trifluoroacetates.

Preference is given to compounds of the formula I in which
R1 and R3
 are each hydrogen;
R2 and R4
 are each independently hydrogen, F, Cl, Br, $NH_2$, $NHCH_3$ or $N(CH_3)_2$;
R5 is hydrogen, methyl, ethyl or cyclopropyl;
R6 is hydrogen or methyl;
R7 and R8
 are each hydrogen;
W is $C_rH_{2r}$ or $C_sH_{2s-2}$;
 where one or more $CH_2$ groups in $C_rH_{2r}$ and $C_sH_{2s-2}$ may be replaced by NR17, oxygen or S;
  R17 is hydrogen or methyl;
  r is 1, 2, 3, 4, 5 or 6;
  s is 2, 3, 4, 5 or 6;
X is —C(O)— or —S(O)$_2$—;
z is a bond;

and also their pharmaceutically acceptable salts and trifluoroacetates.

Particular preference is given to compounds of the formula I in which
R1 and R3
 are each hydrogen;
R2 and R4
 are each independently hydrogen, F, Cl, $NH_2$, $NHCH_3$ or $N(CH_3)_2$;
R5 is hydrogen, methyl, ethyl or cyclopropyl;
R6 is hydrogen or methyl;
R7 and R8
 are each hydrogen;
W is $C_rH_{2r}$ or $C_sH_{2s-2}$;
 where one or more $CH_2$ groups in $C_rH_{2r}$ and $C_sH_{2s-2}$ may be replaced by NR17, oxygen or S;
  R17 is hydrogen, methyl;
  r is 1, 2, 3, 4, 5 or 6;
  s is 2, 3, 4, 5 or 6;
X is —C(O)— or —S(O)$_2$—;
Z is a bond;

and also their pharmaceutically acceptable salts and trifluoroacetates.

Very particular preference is given to compounds of the formula I selected from the group of:
1-[2-(8-bromo-6-chloro-2-methyl-1,2,3,4-tetrahydroiso-quinolin-4-yl)phenyl]pyrrolidin-2-one,
1-[2-((R)-6,8-dichloro-2-methyl-1,2,3,4-tetrahydroiso-quinolin-4-yl)phenyl]-3-methyl-1,3-dihydroimidazol-2-one,
(R)-6,8-dichloro-4-[2-(1,1-dioxo-1-□□-isothiazolidin-2-yl)phenyl]-2-methyl-1,2,3,4-tetrahydroisoquinoline,
3-[2-((R)-6,8-dichloro-2-methyl-1,2,3,4-tetrahydroiso-quinolin-4-yl)phenyl]-oxazolidin-2-one, 1-[2-((R)-6,8-dichloro-2-methyl-1,2,3,4-tetrahydroisoquinolin-4-yl)phenyl]-1,3-dihydro-imidazol-2-one,
1-[2-((R)-6,8-dichloro-2-methyl-1,2,3,4-tetrahydroisoquinolin-4-yl)phenyl]imidazolidin-2-one,
1-[2-((R)-6,8-dichloro-2-methyl-1,2,3,4-tetrahydroisoquinolin-4-yl)phenyl]pyrrolidin-2-one,
1-[2-((R)-6,8-dichloro-2-methyl-1,2,3,4-tetrahydroisoquinolin-4-yl)phenyl]pyrrolidin-2-one,
1-[3-((S)-6,8-dichloro-2-methyl-1,2,3,4-tetrahydroisoquinolin-4-yl)phenyl]piperidin-2-one,
1-[2-((R)-6,8-dichloro-2-cyclopropyl-1,2,3,4-tetrahydroisoquinolin-4-yl)phenyl]pyrrolidin-2-one,
3-[2-((R)-6,8-dichloro-2-cyclopropyl-1,2,3,4-tetrahydroisoquinolin-4-yl)phenyl]-oxazolidin-2-one and
6,8-dichloro-4-[4-(1,1-dioxo-1-□□-[1,2,5]thiadiazolidin-2-yl)phenyl]-2-methyl-1,2,3,4-tetrahydroisoquinoline, and also their pharmaceutically acceptable salts and trifluoroacetates.

Especially preferred are compounds of the formula I selected from the group of:
1-[2-(8-bromo-6-chloro-2-methyl-1,2,3,4-tetrahydroisoquinolin-4-yl)phenyl]pyrrolidin-2-one,
1-[2-((R)-6,8-dichloro-2-methyl-1,2,3,4-tetrahydroisoquinolin-4-yl)phenyl]-3-methyl-1,3-dihydroimidazol-2-one,
(R)-6,8-dichloro-4-[2-(1,1-dioxo-1-□□-isothiazolidin-2-yl)phenyl]-2-methyl-1,2,3,4-tetrahydroisoquinoline,
3-[2-((R)-6,8-dichloro-2-methyl-1,2,3,4-tetrahydroisoquinolin-4-yl)phenyl]oxazolidin-2-one,
1-[2-((R)-6,8-dichloro-2-methyl-1,2,3,4-tetrahydroisoquinolin-4-yl)phenyl]-1,3-dihydro-imidazol-2-one,
1-[2-((R)-6,8-dichloro-2-methyl-1,2,3,4-tetrahydroisoquinolin-4-yl)phenyl]imidazolidin-2-one,
1-[2-((R)-6,8-dichloro-2-methyl-1,2,3,4-tetrahydroisoquinolin-4-yl)phenyl]pyrrolidin-2-one,
1-[2-((R)-6,8-dichloro-2-methyl-1,2,3,4-tetrahydroisoquinolin-4-yl)phenyl]pyrrolidin-2-one,
1-[3-((S)-6,8-dichloro-2-methyl-1,2,3,4-tetrahydroisoquinolin-4-yl)phenyl]piperidin-2-one,
1-[2-((R)-6,8-dichloro-2-cyclopropyl-1,2,3,4-tetrahydroisoquinolin-4-yl)phenyl]pyrrolidin-2-one and
3-[2-((R)-6,8-dichloro-2-cyclopropyl-1,2,3,4-tetrahydroisoquinolin-4-yl)phenyl]-oxazolidin-2-one, and also their pharmaceutically acceptable salts and trifluoroacetates.

Particularly preferred are compounds of the formula I selected from the group of:
1-[2-(8-bromo-6-chloro-2-methyl-1,2,3,4-tetrahydroisoquinolin-4-yl)phenyl]pyrrolidin-2-one,
1-[2-((R)-6,8-dichloro-2-methyl-1,2,3,4-tetrahydroisoquinolin-4-yl)phenyl]-3-methyl-1,3-dihydroimidazol-2-one,
(R)-6,8-dichloro-4-[2-(1,1-dioxo-1-□□-isothiazolidin-2-yl)phenyl]-2-methyl-1,2,3,4-tetra-hydroisoquinoline,
3-[2-((R)-6,8-dichloro-2-methyl-1,2,3,4-tetrahydroisoquinolin-4-yl)phenyl]oxazolidin-2-one,
1-[2-((R)-6,8-dichloro-2-methyl-1,2,3,4-tetrahydroisoquinolin-4-yl)phenyl]-1,3-dihydro-imidazol-2-one,
1-[2-((R)-6,8-dichloro-2-methyl-1,2,3,4-tetrahydroisoquinolin-4-yl)phenyl]imidazolidin-2-one,
1-[2-((R)-6,8-dichloro-2-methyl-1,2,3,4-tetrahydroisoquinolin-4-yl)phenyl]pyrrolidin-2-one and
1-[2-((R)-6,8-dichloro-2-methyl-1,2,3,4-tetrahydroisoquinolin-4-yl)phenyl]pyrrolidin-2-one, and also their pharmaceutically acceptable salts and trifluoroacetates.

In a further embodiment, preference is given to compounds of the formula I in which the R1, R2, R3 and R4 radicals are each independently described by hydrogen, F, Cl, Br, CN or R11-($C_mH_{2m}$)-$A_n$- where m and n are each independently zero or 1, R11 is hydrogen, methyl or $C_pF_{2p+1}$ and A is oxygen, $NCH_3$ or $S(O)_q$, where p is 1 or 2 and q is zero, 1 or 2; particular preference is given to compounds of the formula I in which R1 and R3 are each hydrogen and R2 and R4 are each independently hydrogen, F, Cl, Br, $NH_2$, $NHCH_3$ or $N(CH_3)_2$, for example Cl or Br. In one embodiment, preference is given to compounds of the formula I in which R1 and R3 are each hydrogen and R2 and R4 are each independently F, Cl, $NH_2$, $NHCH_3$ or $N(CH_3)_2$, for example Cl.

In a further embodiment, preference is given to compounds of the formula I in which R5 is described by hydrogen, methyl, ethyl or cyclopropyl; particular preference is given to compounds of the formula I in which R5 is hydrogen, methyl or cyclopropyl, for example methyl.

In a further embodiment, preference is given to compounds of the formula I in which R6 is described by hydrogen or methyl, for example hydrogen.

In a further embodiment, preference is given to compounds of the formula I in which the R7 and R8 radicals are each independently described by hydrogen, F, Cl, CN, $CO_2R12$, NR13R14 or R16-($C_{mm}H_{2mm}$)—$B_{nn}$—, where R12 is hydrogen, methyl or ethyl, R13 and R14 are each independently hydrogen, alkyl having 1, 2, 3 or 4 carbon atoms or cycloalkyl having 3, 4, 5 or 6 carbon atoms, or R13 and R14, together with the nitrogen atom to which they are bonded, form a 5-, 6- or 7-membered ring in which one $CH_2$ group may be replaced by NR15, S or oxygen, and where R15 is hydrogen, alkyl having 1, 2, 3 or 4 carbon atoms or cycloalkyl having 3, 4, 5 or 6 carbon atoms, and where mm is zero, 1 or 2, nn is zero or 1, and R16 is hydrogen, methyl or $C_{pp}F_{2pp+1}$, where B is oxygen or $S(O)_{qq}$, where pp is 1 or 2 and qq is zero, 1 or 2; particular preference is given to compounds of the formula I in which R7 and R8 are each hydrogen.

In a further embodiment, preference is given to compounds of the formula I in which W is described by $C_rH_{2r}$ or $C_sH_{2s-2}$ where one or more $CH_2$ groups in $C_rH_{2r}$ and $C_sH_{2s-2}$ may be replaced by NR17, oxygen or S, where R17 is hydrogen, alkyl having 1, 2, 3 or 4 carbon atoms or cycloalkyl having 3, 4, 5 or 6 carbon atoms, especially hydrogen or methyl, for example hydrogen, and where r is 2, 3, 4, 5, 6, 7 or 8, in particular 2, 3, 4, 5 or 6, and s is 2, 3, 4, 5, 6, 7 or 8, in particular 2, 3, 4, 5 or 6.

In a further embodiment, preference is given to compounds of the formula I in which X is —C(O)— or —S(O)$_2$—.

In a further embodiment, preference is given to compounds of the formula I in which Z is —C(O)—.

In another embodiment, preference is given to compounds of the formula I in which Z is a bond.

When the compounds of the formula I contain one or more centers of asymmetry, they may each independently have either S or R configuration. The compounds may be present as optical isomers, as diastereomers, as racemates or as mixtures in all ratios thereof. The compounds of the formula I may also be present in the form of rotational isomers.

The present invention encompasses all possible tautomeric forms of the compounds of the formula I.

The present invention also encompasses derivatives of the compounds of the formula I, for example solvates such as hydrates and alcohol adducts, esters, prodrugs and other physiologically acceptable derivatives of the compounds of the formula I, and also active metabolites of the compounds of the formula I. The invention likewise encompasses all crystal modifications of the compounds of the formula I.

Alkyl radicals may be straight-chain or branched. This is also true when they bear substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl and hexyl. Preferred alkyl radicals are methyl, ethyl, n-propyl, isopropyl and n-butyl. In alkyl radicals, one or more, for example 1, 2, 3, 4, 5, 6, 7, 8, 9, 10, 11, 12, 13 or 14, hydrogen atoms may be substituted by fluorine atoms. Examples of such fluoroalkyl radicals are trifluoromethyl, 2,2,2-trifluoroethyl, pentafluoroethyl, heptafluoroisopropyl. Substituted alkyl radicals may be substituted in any positions.

Alkylene radicals, for example $C_mH_{2m}$, $C_{mm}H_{2mm}$ or $C_rH_{2r}$, may be straight-chain or branched. This is also true when they bear substituents or occur as substituents of other radicals, for example in fluoroalkylene radicals, for example in $C_pF_{2p}$ and $C_{pp}F_{2pp}$. Examples of alkylene radicals are methylene, ethylene, 1-methylmethylene, propylene, 1-methylethylene, butylene, 1-propylmethylene, 1-ethyl-1-methylmethylene, 1,2-dimethylethylene, 1,1-dimethylmethylene, 1-ethylethylene, 1-methylpropylene, 2-methylpropylene, pentylene, 1-butylmethylene, 1-propylethylene, 1-methyl-2-ethylethylene, 1,2-dimethylpropylene, 1,3-dimethylpropylene, 2,2-dimethylpropylene, hexylene and 1-methylpentylene. In alkylene radicals, one or more, for example 1, 2, 3, 4, 5, 6, 7, 8, 9, 10, 11 or 12, hydrogen atoms may be substituted by fluorine atoms.

Substituted alkylene radicals may be substituted in any positions. In the alkylene radicals, one or more $CH_2$ groups may be replaced by oxygen, S, NH, N-alkyl or N-cycloalkyl. Both in straight-chain and in branched alkylene chains, $CH_2$ groups may be replaced by oxygen, S, NH, N-alkyl or N-cycloalkyl, for example as a 1-hydroxy-ethylene radical.

Alkenylene radicals, for example $C_sH_{2s-2}$, may be straight-chain or branched. This is also true when they bear substituents, for example in fluoroalkenylene radicals. The alkenylene radicals may be unsaturated in different positions. Examples of alkenylene radicals are ethenylene, 1-methylethenylene, propenylene, but-1-enylene, but-2-enylene, 1-methylprop-1-enylene, 1,2-dimethylethylene, pentenylene or hexenylene. In alkenylene radicals, one or more, for example 1, 2, 3, 4, 5, 6, 7, 8, 9 or 10, hydrogen atoms may be substituted by fluorine atoms. Substituted alkenylene radicals may be substituted in any positions. In the alkenylene radicals, one or more $CH_2$ groups may be replaced by oxygen, S, NH, N-alkyl or N-cycloalkyl. Both in straight-chain and in branched alkenylene chains, $CH_2$ groups may be replaced by oxygen, S, NH, N-alkyl or N-cycloalkyl.

Examples of cycloalkyl radicals are cyclopropyl, cyclobutyl, cyclopentyl or cyclohexyl. In cycloalkyl radicals, one or more, for example 1, 2, 3, 4, 5, 6, 7, 8, 9, 10, 11 or 12, hydrogen atoms may be substituted by fluorine atoms. Substituted cycloalkyl radicals may be substituted in any positions. Cycloalkyl radicals may also be present in branched form as alkylcycloalkyl or cycloalkylalkyl, for example methylcyclohexyl or cyclohexylmethyl.

Examples of rings from NR13R14 where R13 and R14 with the nitrogen atom to which they are bonded form a 4-, 5-, 6- or 7-membered ring are morpholine, pyrrolidine, piperidine, piperazine and N-methylpiperazine.

The terminal $CH_3$ groups in an alkyl radical are also regarded as $CH_2$ units, and are interpreted in this context as being $CH_2$—H moieties. This also applies in branched alkylene radicals, for example $C_mH_{2m}$, $C_{mm}H_{2mm}$ or $C_rH_{2r}$.

When a variable, for example cycloalkyl or R1, occurs more than once as a component, the definitions of the variables are independent from one another at each instance.

When the compounds of the formula I contain one or more acidic or basic groups or one or more basic heterocycles, the corresponding physiologically or toxicologically acceptable salts are also included in the invention, especially the pharmaceutically usable salts. For instance, the compounds of the formula I can be deprotonated at an acidic group and be used, for example, in the form of alkali metal salts, preferably sodium or potassium salts, or in the form of ammonium salts, for example as salts with ammonia or organic amines or amino acids. Since compounds of the formula I always contain at least one basic group, they may also be prepared in the form of their physiologically acceptable acid addition salts, for example with the following acids: from inorganic acids such as hydrochloric acid, sulfuric acid or phosphonic acid, or from organic acids such as acetic acid, citric acid, tartaric acid, lactic acid, malonic acid, methanesulfonic acid, fumaric acid. Useful acid addition salts include salts of all pharmacologically acceptable salts, for example halides, especially hydrochlorides, lactates, sulfates, citrates, tartrates, acetates, phosphates, methylsulfonates, p-toluenesulfonates, adipates, fumarates, gluconates, glutamates, glycerolphosphates, maleates and pamoates (this group also corresponds to the physiologically acceptable anions); but also trifluoroacetates.

The invention also provides the processes described below for preparing compounds of the formula I.

The compounds of the formula I described here can be prepared, for example, according to or analogously to literature methods starting from aniline derivatives of the formula VIII

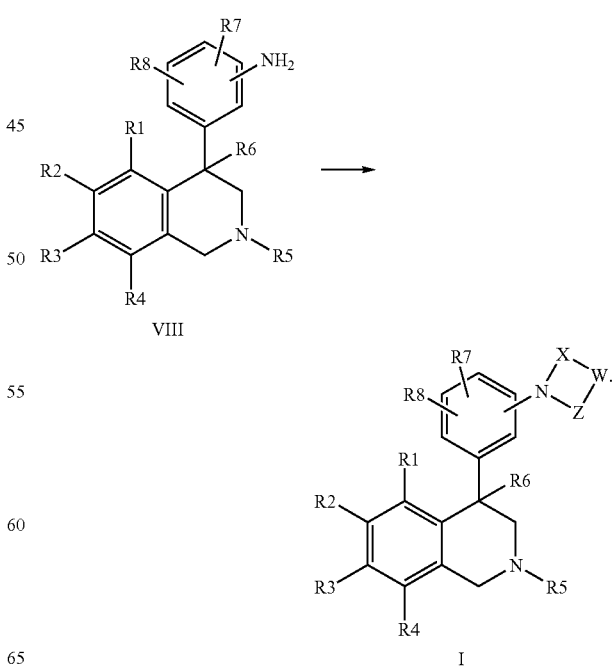

The aniline of the formula VIII can, for example, be converted by heating with the corresponding acids of the formula XXII in polyphosphoric acid (PPA) to the compounds of the formula Ia (Tetrahedron Letters 2003, 44, 2133), where R1 to R8 and W are each as defined above
and
X and Z each correspond to —C(O)—.

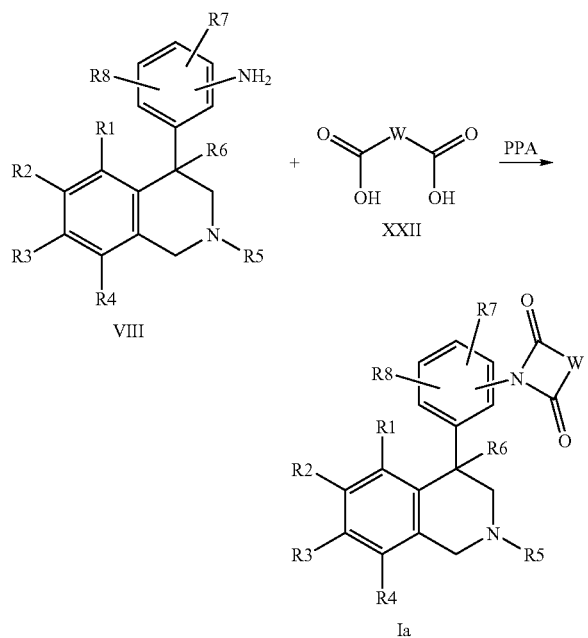

VIII

Alternatively, it is possible to obtain compounds of the formula Ia by reacting anilines of the formula VIII in aprotic solvents such as dichloromethane with anhydrides of the XXIX type to give intermediate amide acids. The desired imides of the formula Ia are then obtained by ring-closing the intermediates in aprotic solvents such as dichloromethane with suitable cyclizing reagents such as EDC in the presence of bases such as Hünig's base. Alternatively, the intermediates may also be heated in high-boiling solvents such as diphenyl ether or entirely without solvent, so that there is formation of ring closure with loss of water, where the R1-R8 and W radicals are each as defined above
and
X and Z each correspond to —C(O)—.

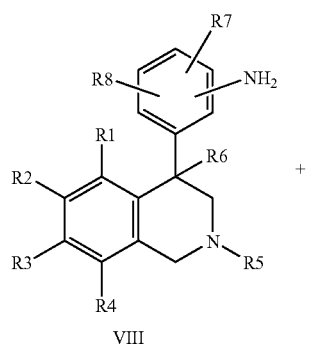

VIII

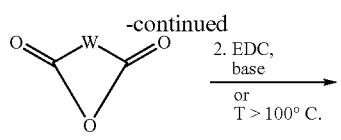

XXIX

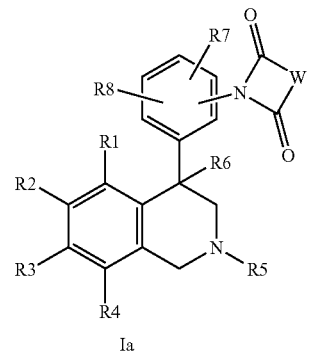

Ia

Compounds of the formula Ib may be formed, for example, in a two-stage reaction starting from isocyanatocarboxylic esters of the formula XII. In this case, the urea is formed first as an intermediate by reaction of the aniline nitrogen with the isocyanate group before there is subsequent ring closure under acid catalysis, where R1 to R8 are each as defined above, X and Z each correspond to —C(O)—, R22 is alkyl having 1, 2, 3 or 4 carbon atoms, for example methyl or ethyl, —$V_N$—NH— is a W radical in which a terminal $CH_2$ group has been replaced by NH and —V'—NCO is a W radical in which a terminal $CH_2$ group has been replaced by an isocyanate group.

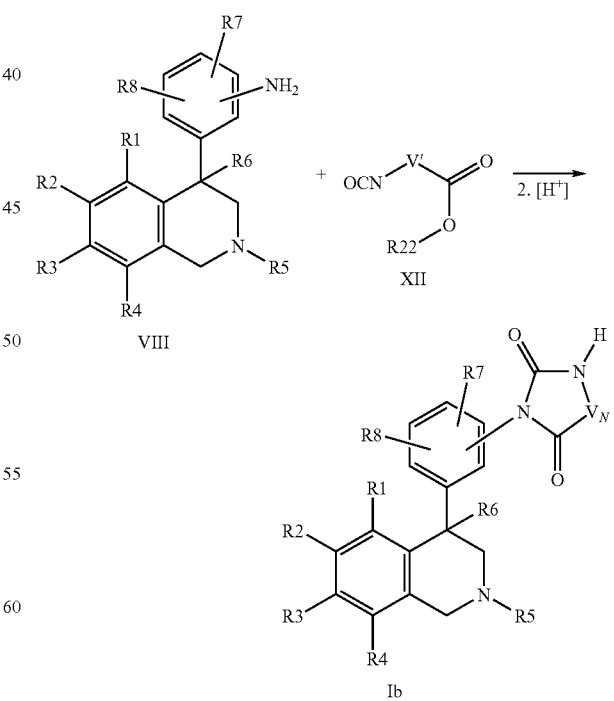

A variation in the R17 radical can subsequently be achieved by alkylating the compound of the formula Ib in the presence of a base, for example lithium diisopropylamide or lithium or sodium hexamethyldisilazide with an alkylating agent of the formula XIII, where R1 to R8 and R17 are each as defined above, X and Z each correspond to —C(O)—, —$V_N$—NH— is a W radical in which a terminal $CH_2$ group has been replaced by NH, —$V_N$—NR17- is a W radical in which a terminal $CH_2$ group has been replaced by NR17 and

LG corresponds to a leaving group common in alkylations, for example bromide, chloride, tosylate or mesylate.

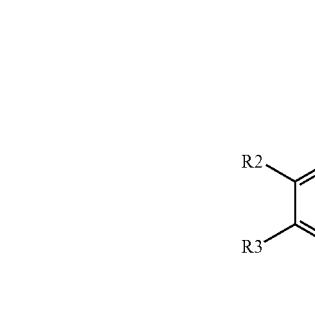

Alternatively, the ring can also be formed in a three-stage sequence. To this end, a carbonyl group is first transferred to the anilinic nitrogen. This is done, for example, with chloroformic acid derivatives of the formula XIV or carbonyldiimidazole. Subsequent reaction with amino esters of the formula XV, followed by acid- or base-catalyzed cyclization, preferably with hydrochloric acid or sodium hexamethyldisilazide, leads to compounds of the formula Ic, where R1 to R8, R17 and —$V_N$—NR17- are each as defined above, R23 is alkyl having 1, 2, 3 or 4 carbon atoms, for example methyl or ethyl, and R24 is an optionally substituted phenyl radical, for example phenyl or 4-nitrophenyl.

Cyclic ureas of the formula Id can be obtained from the product of the aniline of the formula VIII with the chloroformic acid derivative of the formula XIV by reacting the carbamate formed with amines of the formula XVI, followed by a cyclization step in the presence of a base, for example sodium hydride, potassium carbonate or sodium hexamethyldisilazide, where R1 to R8, R17, R24, —$V_N$—NR17- and —$V_N$—NHR17 are each as defined above, and Y is a leaving group, for example chlorine, or else a precursor to a leaving group, for example hydroxyl, which is then converted to a leaving group, for example with mesyl chloride.

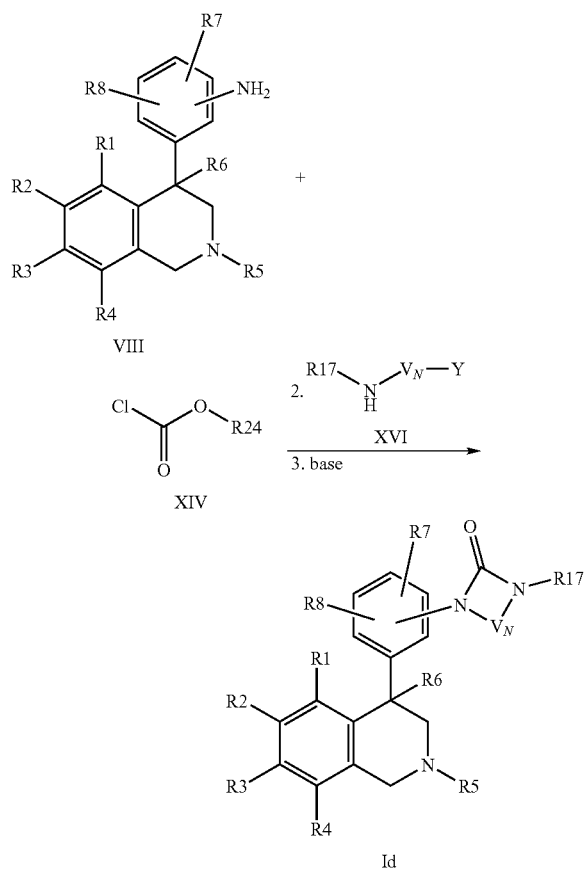

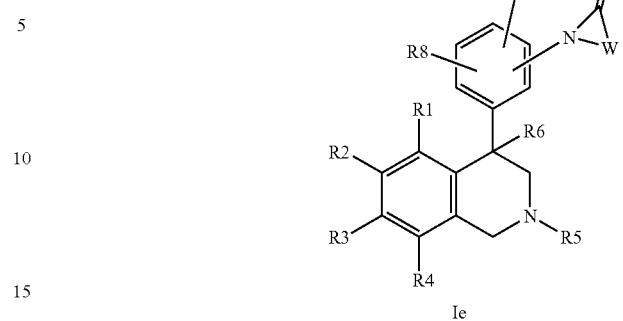

Alternatively, it is also possible to react haloaromatics of the formula XVIII directly with lactams of the formula XIX in the presence of catalysts, for example copper iodide, to give compounds of the formula Ie (J. Am. Chem. Soc. 2001, 7727, ibid. 2002, 7421), where R1-R8 and W are each as defined above, X corresponds to —C(O)—, Z is a bond and Hal is Cl, Br, I or —O-triflate.

Lactams of the formula Ie may be prepared by reacting an aniline of the formula VIII with lactones of the formula XVII (Synlett 2001, 1485) by, in the hydroxy amides formed as an intermediate, making, from the hydroxyl group by reaction with, for example, sulfonyl chlorides, anhydrides or strong acids, a good leaving group which is then subsequently substituted by the anilinic nitrogen, preferably in the presence of base, for example sodium hydride, potassium carbonate or sodium hexamethyldisilazide, where R1 to R8 and W are each as defined above, X corresponds to —C(O)— and

Z is a bond.

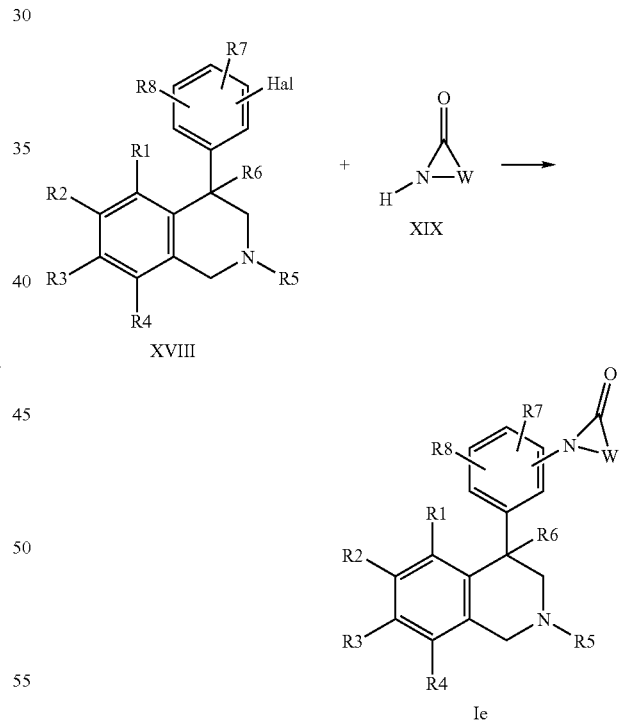

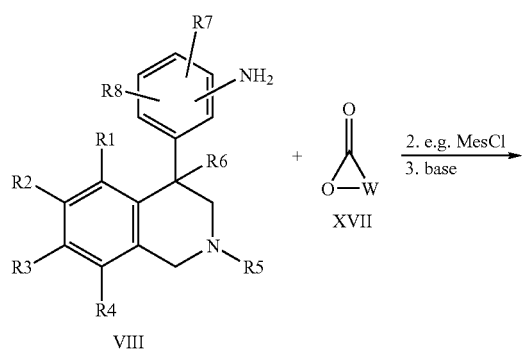

The haloaromatics of the formula XVIII are prepared starting from the carbonyl derivatives of the formula VI analogously to the formation of the aniline derivatives of the formula VIII which is described below.

A further alternative is the reaction of anilines of the formula VIII with acid chlorides of the formula XXV to give compounds of the formula Ie. The amides obtained as an intermediate are then cyclized in the presence of bases such as sodium hydride, potassium carbonate or sodium hexamethyldisilazide in solvents such as THF, DMSO and DMF. The R1 to R8, LG and W radicals are each as defined above,
Z corresponds to a bond and
X is —C(O)—.

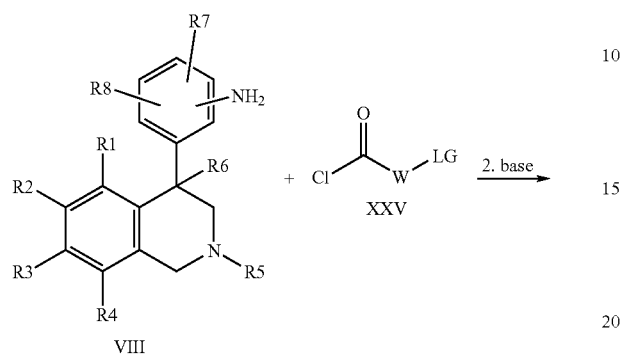

VIII

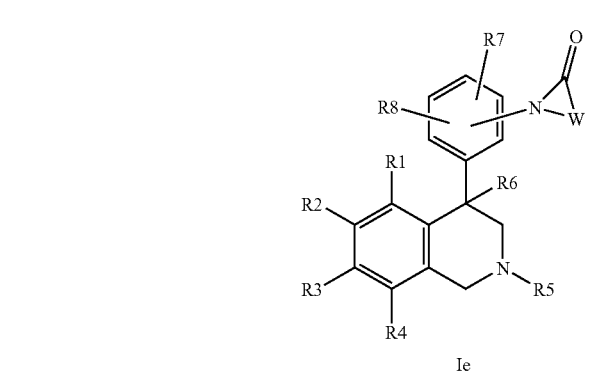

Ie

Sulfonamides of the formula If can be prepared starting from the anilines of the formula VIII by reacting with chloroalkylsulfamyl chlorides of the formula XX (Tetrahedron Letters 44, 5483 (2003)), where R1 to R8, R17 and —$V_N$—NR17- are each as defined above,
T is Cl or Br,
X corresponds to —$SO_2$—
and
Z is a bond.

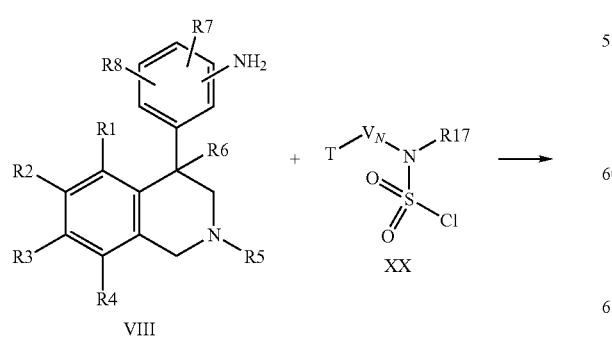

VIII

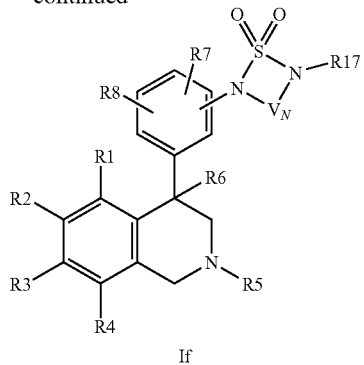

If

Compounds of the formula Ig may be formed via an acid-catalyzed cyclization reaction. Starting from the ureas of the formula XXI, which can be prepared by one of the above-mentioned methods, compounds of the formula Ig are prepared in the presence of acid, for example hydrochloric acid or formic acid, with elimination of the ketal or acetal,
where R1 to R8 and R17 are each as defined above,
X corresponds to —C(O)—,
Z is a bond,
—NR17-V'''—CV*HCV'''(ORa)$_2$ corresponds to a W radical with the definition of $C_rH_{2r}$ in which a terminal $CH_2$ group has been replaced by NR17 and a further $CH_2$ group by an acetal/ketal moiety, and V* and V''' represent possible branches of the alkylene radical, where Ra is alkyl having 1, 2, 3 or 4 carbon atoms, for example methyl or ethyl, or the two Ra radicals together form an ethylene radical and
—NR17-V''CV*=CV'''— is a W radical with the definition of $C_sH_{2s-2}$ in which a terminal $CH_2$ group has been replaced by NR17 and V* and V''' represent possible branches of the alkenyl radical.

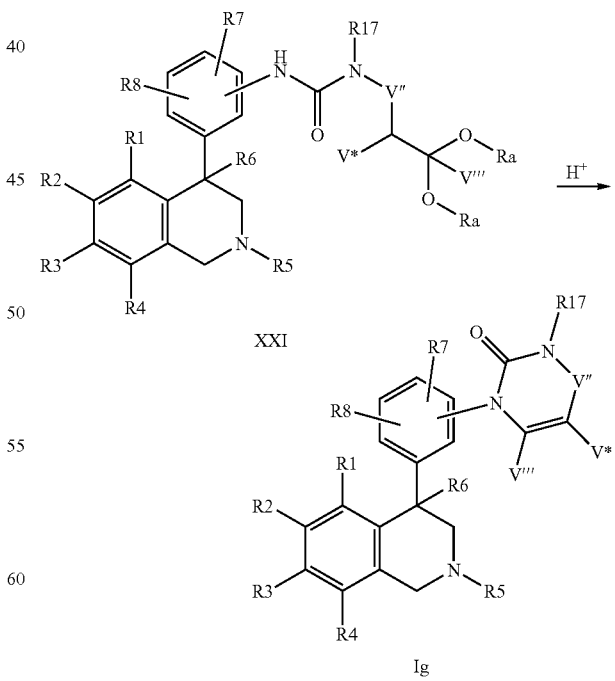

XXI

Ig

Compounds of the formula Ih may be obtained by first reacting the aniline VIII with chlorothioformates of the formula XXVI such as phenyl chlorothioformate and subsequently allowing the resulting intermediate thiocarbamate, after treatment with sodium methoxide solution, to react with an acid chloride of the type XXVII. The R1 to R8, R24 and LG radicals are each as defined above.

$V_K$ is a W group which has been shortened by one $CH_2$ group, $V_S$—S— is a W group in which one $CH_2$ group has been replaced by sulfur and X and Z each correspond to —C(O)—.

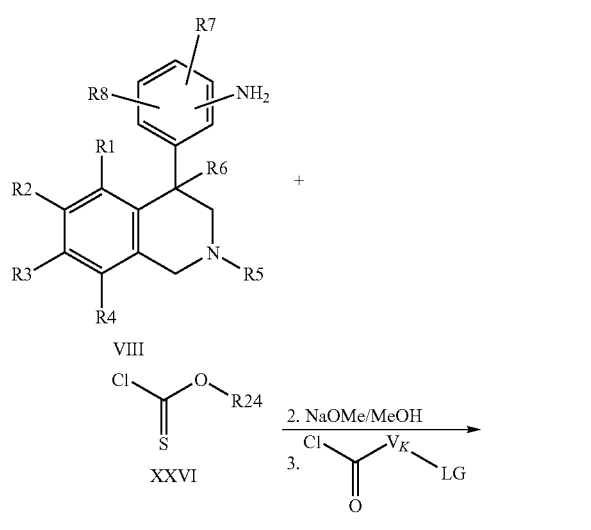

Compounds of the formula Ii can be synthesized in a three-stage sequence as follows. First, anilines of the type VIII are reacted in aprotic solvents such as THF in the presence of bases such as sodium hexamethyldisilazide with acid chlorides of type XXVIII to give intermediate amides. Subsequently, the protecting group P is removed from the oxygen in the presence of nucleophiles and bases such as potassium carbonate in methanol. Finally, the resulting alcohol is reacted in an aprotic solvent such as THF with a carbonyl equivalent such as 1,1-carbonyldiimidazole or phosgene in the presence of a base such as sodium hexamethyldisilazide.

The R1-R8 radicals are each as defined above, $V_O$—O— corresponds to a W group in which one $CH_2$ group has been replaced by oxygen, P corresponds to a protecting group such as acetyl, benzoyl, benzoxycarbonyl or trityl and X and Z each correspond to —C(O)—.

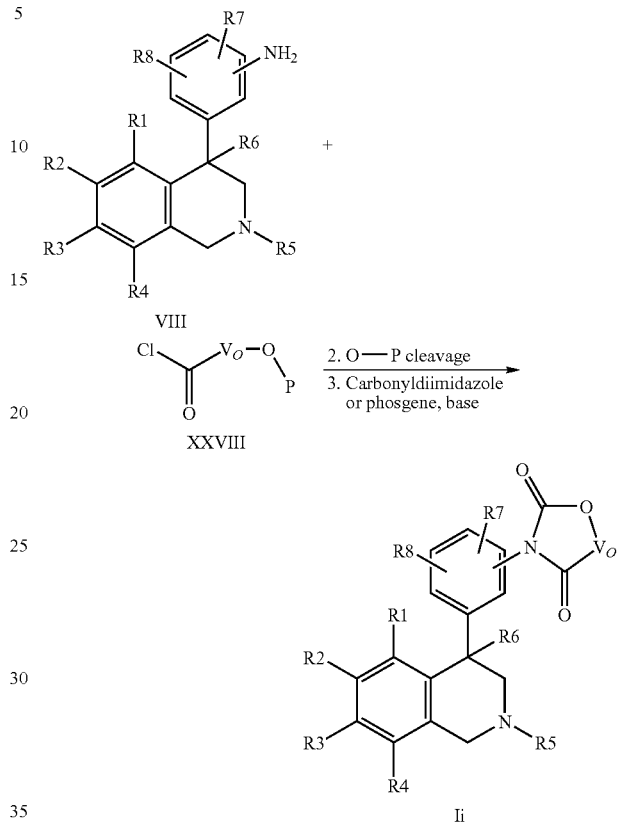

Compounds of the formula Ij can be prepared by reacting anilines of the formula VIII with chloroformates of the formula XXX in aprotic solvents such as THF, and subsequently ring-closing the intermediate carbamate formed in aprotic solvents such as THF in the presence of a base such as sodium hydride. The R1-R8, LG and $V_O$—O radicals are each as defined above and Z corresponds to a bond and X is —C(O)—.

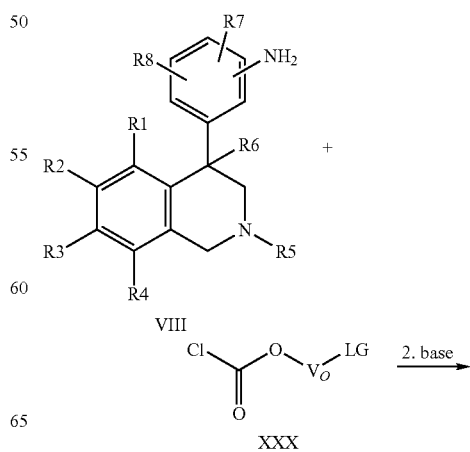

-continued

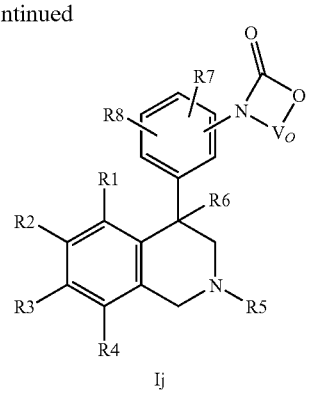

Ij

Compounds of the formula Ik can be obtained by reacting anilines of the formula VIII with sulfonyl chlorides of the formula XXXI in aprotic solvents such as THF in the presence of bases such as sodium hexamethyldisilazide. The R1-R2, T and W radicals are each as defined above and Z corresponds to a bond and X is —$SO_2$—.

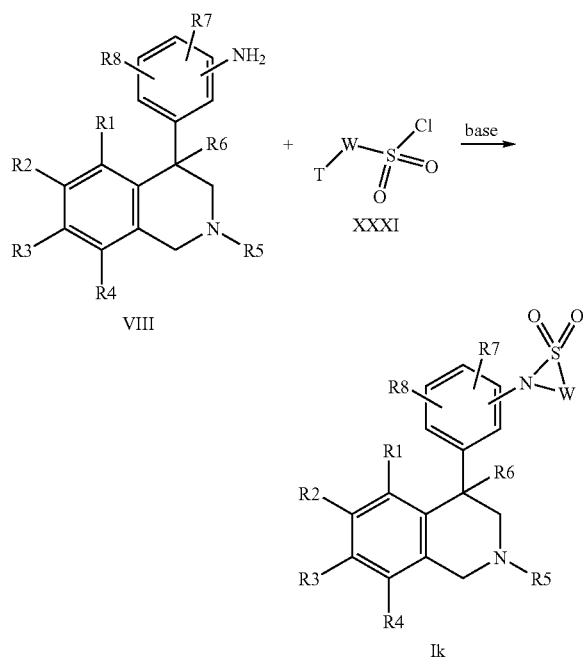

The compounds of the formulae XII, XIII, XIV, XV, XVI, XVII, XIX, XX, XXII, XXV, XXVI, XXVII, XXVIII, XXIX, XXX and XXXI are commercially available or can be prepared according to or analogously to processes which are described in the literature and are known to those skilled in the art.

The starting compounds of the formula VIII can be prepared as follows:

Reduction of the carbonyl moiety in compounds of the formula VI and subsequent acid-catalyzed cyclization of the corresponding alcohols of the formula VII (cf. Tetrahedron Lett. 1989, 30, 5837; Org. Prep. Proced. Int. 1995, 27, 513) can afford tetrahydroisoquinolines of the formula VIIIa by known processes, where R1 to R8 are each as defined above and R20 is a nitrogen protecting group familiar to those skilled in the art, for example an acetyl radical.

Compounds of the formula VIII are subsequently obtained in the manner known to those skilled in the art starting from compounds of the type of the formula VIIIa by removing the protecting group R20. This is done in protic solvents such as water or lower alcohols, preferably under acid catalysis, for example with hydrochloric acid or trifluoroacetic acid, or under base catalysis, for example in the presence of sodium methoxide or ethoxide.

Alternatively, on completion of reduction, the protecting group R20 can be detached before the cyclization, which advantageously succeeds in the presence of strong bases, for example sodium methoxide or ethoxide in methanol or ethanol. However, it is also possible to remove R20 with acids such as hydrochloric acid, advantageously in the presence of alcohols such as methanol or ethanol. Preceding removal of R20 is advisable particularly in the case of the ortho-amino derivatives. It is thus possible to directly obtain the unprotected anilines of the formula VIII.

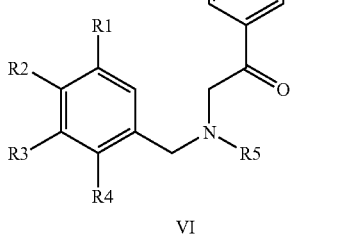

VI

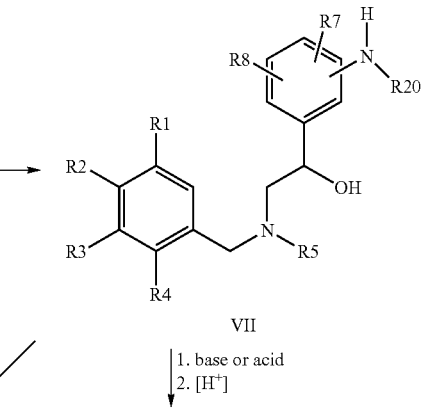

VII

[H+]

1. base or acid
2. [H+]

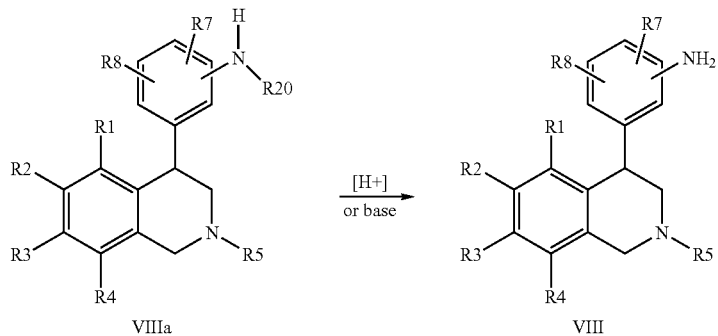

To prepare alkyl-branched compounds of the formula I in which R6 is not hydrogen, the corresponding diphenylacetic esters of the formula IX can be alkylated in the alpha position with R6 by known methods. Advantageously, the anilinic hydrogen atom is replaced by the protecting group R21, for example allyl or benzyl. The compounds of the formula X can be converted by standard processes to the corresponding amides of the formula XI which are converted in a Pictet-Spengler-like reaction to the desired tetrahydroisoquinolines of the formula VIIIb (cf. Tetrahedron 1987, 43, 439; Chem. Pharm. Bull. 1985, 33, 340), where R1 to R8 and R20 are each as defined above, R21 is a protecting group, for example allyl or benzyl and LG corresponds to a leaving group common in alkylations, for example chloride, bromide, tosylate or mesylate.

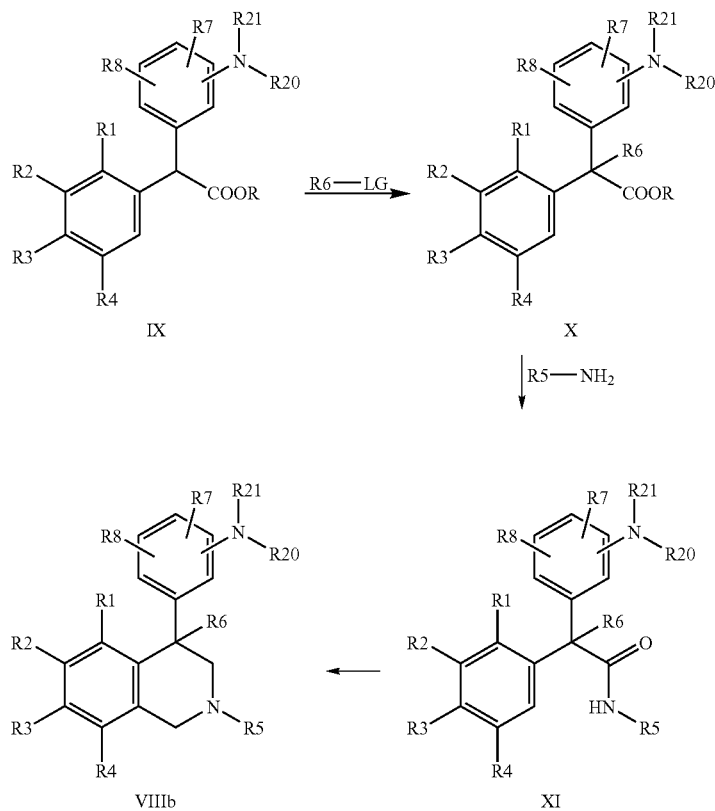

Deprotection of the compound of the formula VIIIb by means of the process known to those skilled in the art affords the free aniline of the formula VIII. Depending on the type of protecting group, carbonyl protecting groups such as acetyl are removed advantageously under acid catalysis (e.g. aqueous HCl) or base catalysis (for example by means of sodium methoxide or ethoxide), while benzyl or allyl protecting groups are best detached by hydrogenation.

Compounds of the formula IX are commercially available or can be prepared according to or analogously to processes which are described in the literature and known to those skilled in the art.

The compounds of the formula VI used above are preferably prepared from benzylamines of the formula IV in the manner known to those skilled in the art and the appropriate amino-substituted alpha-bromoacetophenone compounds of the formula V,
where R1 to R8 and R20 are each as defined above

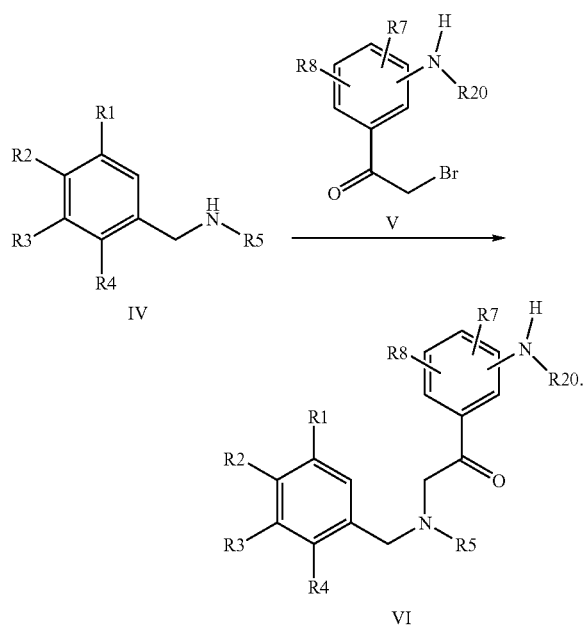

The alpha-bromoacetophenone compounds of the formula V can be obtained in literature processes from the corresponding acetophenone precursors by bromination.

If commercially unavailable, the benzylamine precursors of the formula IV can be synthesized by standard processes known to those skilled in the art from the corresponding benzyl chlorides or bromides of the formula III and the corresponding amines,
where R1 to R5 are each as defined above and X is F, Cl, Br or I, in particular Cl or Br.

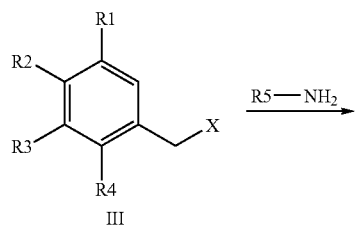

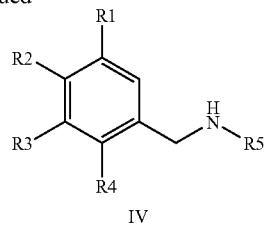

Alternatively, compounds of the formula IV are also obtainable by reductive amination of an aldehyde of the formula IIIa by standard processes known to those skilled in the art,
where R1 to R5 are each as defined above.

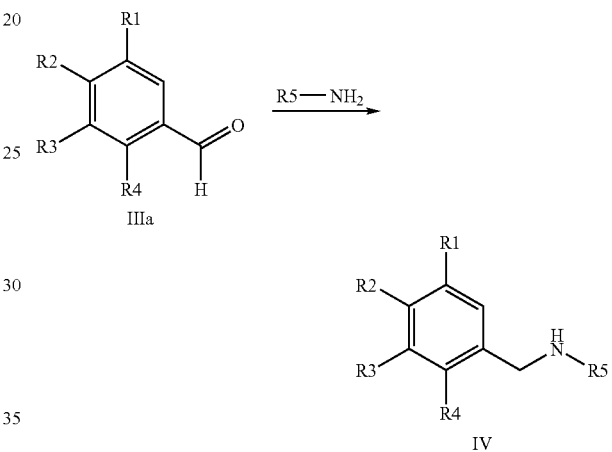

The compounds of the formulae III and IIIa and R5-NH$_2$ are commercially available or can be prepared according to or analogously to processes which are described in the literature and are known to those skilled in the art.

The products and/or intermediates are worked up and, if desired, purified by the customary methods such as extraction, chromatography or crystallization and the customary drying steps.

Not withstanding this class of compounds ability to modulate the sodium/hydrogen proton exchanger and all the respiratory and central nervous system components affected thereby, in addition, the compounds increase the muscle tone of the upper airways, so that snoring is suppressed. The compounds mentioned therefore advantageously find use for the preparation of a medicament for the prevention and treatment of sleep apneas and muscular-related respiratory disorders, and for the preparation of a medicament for the prevention and treatment of snoring.

A combination of an NHE inhibitor of the formula I with a carbonic anhydrase inhibitor (for example acetazolamide) can be found to be advantageous, the latter bringing about metabolic acidosis and thus itself increasing respiratory activity, so that enhanced action and reduced use of active ingredients can be achieved.

As a consequence of their NHE3-inhibitory action, the inventive compounds protect the cellular energy reserves which are rapidly depleted in toxic and pathogenic events and thus lead to cell damage or to cell death. The energy-intensive ATP-consuming sodium absorption in the proximal tubulus is temporarily shut down under the influence of NHE3 inhibitors and the cell can thus survive an acute pathogenic, ischemic or toxic situation. The compounds are therefore suitable, for example, as medicaments for the treatment of ischemic noxae, for example of acute renal failure. Moreover, the compounds are also suitable for the treatment of all chronic renal disorders and nephritis forms which lead to chronic kidney failure as a consequence of increased protein deposition. Accordingly, the compounds of the formula I are suitable for preparing a medicament for the treatment of late diabetic damage, diabetic nephropathy and chronic renal disorders, especially of all renal inflammations (nephritides) which are associated with increased protein/albumin deposition.

It has been found that the compounds used in accordance with the invention have a mild laxative effect and can accordingly also be used advantageously as laxatives or in the event of impending constipation.

Moreover, the inventive compounds may be used advantageously for the prevention and therapy of acute and chronic disorders of the intestinal tract which are induced, for example, by ischemic states in the intestinal region and/or by subsequent reperfusion or by inflammatory states and events. Such complications may occur, for example, as a result of inadequate bowel peristalsis, as are observed, for example, frequently after surgical interventions, in the event of constipation or greatly reduced bowel activity.

With the inventive compounds, the possibility exists of preventing gallstone formation.

The inventive NHE inhibitors are suitable generally for the treatment of disorders which are caused by ischemia and by reperfusion.

As a consequence of their pharmacological properties, the inventive compounds are suitable as antiarrhythmic medicaments.

As a result of their cardioprotective component, the NHE inhibitors are outstandingly suitable for infarction prophylaxis and infarction treatment, and also for the treatment of angina pectoris, in which cases they also inhibit or greatly reduce the pathophysiological processes in the development of ischemically induced states, especially in the triggering of ischemically induced cardiac arrhythmias. Owing to their protective actions against pathological hypoxic and ischemic situations, the compounds of the formula I used in accordance with the invention, as a consequence of inhibition of the cellular $Na^+/H^+$ exchange mechanism, may be used as medicaments for the treatment of all acute or chronic damage induced by ischemia or diseases induced primarily or secondarily thereby.

This also relates to their use as medicaments for surgical interventions. For instance, the inventive compounds may be used in organ transplants, in which case the compounds may be used both for the protection of the organs in the donor before and during the removal, for the protection of removed organs, for example in the course of treatment with or their storage in physiological bath liquids, and also in the course of transfer into the recipient organism pretreated with compounds of the formula I.

The compounds are likewise valuable, protective medicaments in the performance of angioplastic surgical interventions, for example on the heart, and also on peripheral organs and vessels.

Moreover, the inventive compounds may be used in the performance of bypass operations, for example in bypass operations on coronary vessels and in coronary artery bypass graft (CABG).

In accordance with their action against ischemically induced damage, the inventive compounds of the formula I may also be used in resuscitation after a cardiac arrest.

In accordance with their protective action against ischemically induced damage, the compounds are also suitable as medicaments for the treatment of ischemias of the nervous system, especially of the CNS, in which case they are suitable, for example, for the treatment of stroke or of cerebral edema.

Since NHE inhibitors protect human tissue and organs effectively not only against damage which is caused by ischemia and reperfusion but also against the cytotoxic action of medicaments that are used especially in cancer therapy and the therapy of autoimmune disorders, their combined administration with compounds of the formula I is suitable for the reduction or suppression of the cytotoxic effects of a therapy. The reduction in the cytotoxic effects, especially in the cardiotoxicity, as a consequence of co-medication with NHE inhibitors also allows the dose of the cytotoxic therapeutic agents to be increased and/or the medication with such medicaments to be prolonged. The therapeutic benefit of such a cytotoxic therapy can be considerably enhanced by the combination with NHE inhibitors. The compounds of the formula I are suitable in particular for improving the therapy with pharmaceutical agents or medications which have an undesired cardiotoxic component.

Generally, the NHE inhibitors described here can be combined favorably with other compounds which likewise regulate the intracellular pH, in which case possible combination partners are inhibitors of the enzyme group of the carbonic anhydrases, inhibitors of the systems transporting bicarbonate ions, such as the sodium bicarbonate cotransporter (NBC) or the sodium-dependent chloride-bicarbonate exchanger (NCBE), and also with other NHE inhibitors with inhibitory action on other NHE subtypes, because they can enhance or modulate the pharmacologically relevant pH-regulating effects of the NHE inhibitors described here.

In accordance with their protective action against ischemically induced damage, the inventive compounds are also suitable as medicaments for the treatment of ischemias of the nervous system, especially of the central nervous system, in which case they are suitable, for example, for the treatment of stroke or of cerebral edema.

The compounds of the formula I are also suitable for the therapy and prophylaxis of diseases and disorders which are induced by overexcitability of the central nervous system, especially for the treatment of epileptic disorders, centrally induced clonic and tonic spasms, states of psychological depression, anxiety disorders and psychoses. In these cases, the inventive NHE inhibitors may be employed alone or in combination with other antiepileptically active substances or antipsychotic active substances, or carbonic anhydrase inhibitors, for example with acetazolamide, and also with further inhibitors of the NHE or of the sodium-dependent chloride-bicarbonate exchanger (NCBE).

Furthermore, the inventive compounds of the formula I are likewise suitable for the treatment of types of shock, for example of allergic, cardiogenic, hypovolemic and bacterial shock.

The compounds of the formula I may likewise be used for the prevention and for the treatment of thrombotic disorders since they, as NHE inhibitors, can also inhibit platelet aggregation themselves. They can also inhibit or prevent the excessive release, taking place after ischemia and reperfusion, of inflammation and coagulation mediators, especially of von Willebrand factor and of thrombogenic selectin proteins. This allows the pathogenic action of thrombogenic and inflammation-relevant factors to be reduced and eliminated. Therefore, it is possible to combine the NHE inhibitors of the present invention with further anticoagulative and/or thrombolytic active ingredients, for example recombinant or natural tissue plasminogen activator, streptokinase, urokinase, acetylsalicylic acid, thrombin antagonists, factor Xa antagonists, fibrinolytically active medicaments, thromboxane receptor antagonists, phosphodiesterase inhibitors, factor VIIa antagonists, clopidogrel, ticlopidin, etc. Combined use of the present NHE inhibitors with NCBE inhibitors and/or with inhibitors of carbonic anhydrase, for example with acetazolamide, is particularly favorable.

Furthermore, the inventive NHE inhibitors feature strong inhibiting action on the proliferations of cells, for example fibroblast cell proliferation and the proliferation of smooth vascular muscle cells. The compounds of the formula I are therefore useful as valuable therapeutic agents for disorders in which cell proliferation constitutes a primary or secondary cause, and can therefore be used as antiatherosclerotics, agents against chronic renal failure, cancers. They may thus be used for the treatment of organ hypertrophies and hyperplasias, for example of the heart and of the prostate. Compounds of the formula I are therefore suitable for the prevention and for the treatment of heart failure (congestive heart failure=CHF) and also in the treatment and prevention of prostate hyperplasia or prostate hypertrophy.

NHE inhibitors also feature a retardation or prevention of fibrotic disorders. They are thus suitable as outstanding agents for the treatment of fibroses of the heart, and also of pulmonary fibrosis, hepatic fibrosis, renal fibrosis and other fibrotic disorders.

Since there is significant elevation in the NHE in essential hypertensives, the compounds of the formula I are suitable for the prevention and treatment of high blood pressure and of cardiovascular disorders. In these cases, they may be used alone or with a suitable combination partner for the treatment of high blood pressure and for the treatment of cardiovascular disorders. For example, one or more diuretics with a thiazide-like action, loop diuretics, aldosterone and pseudoaldosterone antagonists, such as hydrochlorothiazide, indapamide, polythiazide, furosemide, piretanide, torasemide, bumetanide, amiloride, triamterene, spironolactone or eplerone, may be combined with compounds of the formula I. Moreover, the NHE inhibitors of the present invention may be used in combination with calcium antagonists such as verapamil, diltiazem, amlodipine or nifedipine, and with ACE inhibitors, for example ramipril, enalapril, lisinopril, fosinopril or captopril. Further favorable combination partners are also β-blockers such as metoprolol, albuterol etc., antagonists of the angiotensin receptor and its receptor subtypes such as losartan, irbesartan, valsartan, omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of further potassium channels, such as Kv1.5, etc.

Owing to their antiinflammatory effect, inventive NHE inhibitors may be used as antiinflammatory drugs. In mechanistic terms, inhibition of the release of mediators of inflammation is notable in this connection. The compounds can thus be used alone or in combination with an antiinflammatory drug in the prevention or treatment of chronic and acute inflammatory disorders. The combination partners used are advantageously steroidal and non-steroidal antiinflammatory drugs.

It has additionally been found that NHE inhibitors show a beneficial effect on serum lipoproteins. They can therefore be used for the prophylaxis and regression of atherosclerotic lesions by eliminating a causal risk factor. These include not only the primary hyperlipidemias but also certain secondary hyperlipidemias as occur, for example, in the case of diabetes. In addition, NHE inhibitors lead to a distinct reduction in the infarctions induced by metabolic abnormalities and especially to a significant reduction in the induced infarction size and the severity thereof. NHE inhibitors of the formula I therefore advantageously find use for the preparation of a medicament for the treatment of hypercholesterolemia; for the preparation of a medicament for the prevention of atherogenesis; for the preparation of a medicament for the prevention and treatment of atherosclerosis, for the preparation of a medicament for the prevention and treatment of diseases induced by elevated cholesterol levels, for the preparation of a medicament for the prevention and treatment of diseases induced by endothelial dysfunction, for the preparation of a medicament for the prevention and treatment of atherosclerosis-induced hypertension, for the preparation of a medicament for the prevention and treatment of atherosclerosis-induced thromboses, for the preparation of a medicament for the prevention and treatment of hyper-cholesterolemia-induced and endothelial dysfunction-induced ischemic damage and post-ischemic reperfusion damage, for the preparation of a medicament for the prevention and treatment of cardiac hypertrophies and cardiomyopathies and of congestive heart failure (CHF), for the preparation of a medicament for the prevention and treatment of hypercholesterolemia-induced and endothelial dysfunction-induced coronary vasospasms and myocardial infarctions, for the preparation of a medicament for the treatment of said disorders in combinations with hypotensive substances, preferably with angiotensin converting enzyme (ACE) inhibitors and angiotensin receptor antagonists. A combination of an NHE inhibitor of the formula I with an active ingredient lowering the blood fat levels, preferably with an HMG-CoA reductase inhibitor (for example lovastatin or pravastatin), the latter bringing about a hypolipidemic effect and thus increasing the hypolipidemic properties of the NHE inhibitor of the formula I constitutes a favorable combination with enhanced effect and reduced use of active ingredients.

Thus, NHE inhibitors lead to effective protection against endothelial damage of different origins. This protection of the vessels against the syndrome of endothelial dysfunction means that NHE inhibitors are valuable medicaments for the prevention and treatment of coronary vasospasms, peripheral vascular diseases, in particular intermittent claudication, atherogenesis and atherosclerosis, left-ventricular hypertrophy and dilated cardiomyopathy and thrombotic disorders.

It has additionally been found that NHE inhibitors are suitable in the treatment of non-insulin-dependent diabetes (NIDDM), in which case, for example, the insulin resistance is restrained. In this case, it may be favorable to enhance the antidiabetic activity and quality of the effect of the compounds of the invention by combining them with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

In addition to the acute antidiabetic effects, NHE inhibitors counteract the development of late complications of diabetes and can therefore be used as medicaments for the prevention and treatment of late damage from diabetes, such as diabetic nephropathy, diabetic neuropathy, diabetic retinopathy, diabetic cardiomyopathy and other disorders occurring as a consequence of diabetes. They may advantageously be combined with the antidiabetic medicaments described above under NIDDM treatment. The combination with a beneficial dosage form of insulin may be particularly important in this connection.

In addition to the protective effects against acute ischemic events and the subsequent equally acutely stressing reperfusion events, NHE inhibitors also exhibit direct therapeutically utilizable effects against diseases and disorders of the entire mammalian organism which are associated with the manifestations of the chronically progressive aging process and which can also occur independently of acute ischemic states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders connected with an age-related functional impairment or with age-related manifestations of wear of organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated highly significantly by NHE inhibitors. NHE inhibitors are thus outstandingly suitable for the treatment and prevention of the age-related progression in endothelial dysfunction, especially of intermittent claudication. The NHE inhibitors are thus also outstandingly suitable for the prevention and treatment of myocardial infarction, of congestive heart failure (CHF) and also for the treatment and especially for the prevention of age-related forms of cancer.

In this context, a useful combination is that with hypotensive medicaments such as with ACE inhibitors, angiotensin receptor antagonists, diuretics, $Ca^{2+}$ antagonists, etc, or with metabolism-normalizing medicaments such as cholesterol-lowering agents. The compounds of the formula I are thus suitable for the prevention of age-related tissue changes and for maintaining health and prolonging life while retaining a high quality of life.

The inventive compounds are effective inhibitors of the cellular sodium-proton antiporter (Na/H exchanger) which is elevated in numerous disorders (essential hypertension, atherosclerosis, diabetes, etc), even in those cells which are readily amenable to measurements, for example in erythrocytes, thrombocytes or leukocytes. The compounds used in accordance with the invention are therefore suitable as outstanding and simple scientific tools, for example in their use as diagnostic agents for the determination and differentiation of different forms of hypertension, but also of atherosclerosis, of diabetes and of diabetic late complications, proliferative disorders, etc.

Moreover, NHE inhibitors are suitable for the treatment of disorders (human and veterinary) induced by bacteria and by protozoa. The diseases induced by protozoa are in particular malarial disorders in humans and coccidiosis in poultry.

The compounds are also suitable as agents for the control of sucking parasites in human and veterinary medicine and also in crop protection. Preference is given to the use as an agent against blood-sucking parasites in human and veterinary medicine.

The compounds mentioned therefore advantageously find use alone or in combination with other medicaments or active ingredients for preparing a medicament for the treatment or prophylaxis of disorders of respiratory drive, of respiratory disorders, sleep-related respiratory disorders, sleep apneas, of snoring, of acute and chronic renal disorders, of acute kidney failure and of chronic kidney failure, of disorders of intestinal function, of high blood pressure, of essential hypertension, of disorders of the central nervous system, of disorders resulting from CNS overexcitability, epilepsy and centrally induced convulsions or of states of anxiety, depressions and psychoses, of ischemic states of the peripheral or central nervous system or of stroke, of acute and chronic damage to and disorders of peripheral organs or limbs caused by ischemic events or by reperfusion events, of atherosclerosis, of disorders of lipid metabolism, of thromboses, of disorders of biliary function, of infestation by ectoparasites, of disorders caused by endothelial dysfunction, of protozoal disorders, of malaria, for the preservation and storage of transplants for surgical procedures, for use in surgical operations and organ transplants, or for the treatment of states of shock or of diabetes and late damage from diabetes, or of diseases in which cellular proliferation constitutes a primary or secondary cause, and for maintaining health and prolonging life.

The invention further relates to the use of the compounds of the formula I and their pharmaceutically acceptable salts for use as a medicament.

The invention also relates to medicines for human, veterinary or phytoprotective use, comprising an effective amount of a compound of the formula I and/or of a pharmaceutically acceptable salt thereof, and also medicines for human, veterinary or phytoprotective use, comprising an effective amount of a compound of the formula I and/or of a pharmaceutically acceptable salt thereof, alone or in combination with one or more other pharmacological active ingredients or medicaments.

Medicaments which comprise a compound of the formula I or its pharmaceutically acceptable salts can be administered, for example, orally, parenterally, intramuscularly, intravenously, rectally, nasally, by inhalation, subcutaneously or by a suitable transcutaneous administration form, the preferred administration depending on the particular characteristics of the disorder. The compounds of the formula I can be used alone or together with pharmaceutical excipients, both in veterinary and in human medicine, as well as in crop protection. The medicaments comprise active ingredients of the formula I and/or their pharmaceutically acceptable salts generally in an amount of from 0.01 mg to 1 g per dosage unit.

The excipients which are suitable for the desired pharmaceutical formulation are familiar to those skilled in the art on the basis of their expert knowledge. In addition to solvents, gel formers, suppository bases, tablet excipients and other active ingredient carriers, it is possible to use, for example, antioxidants, dispersants, emulsifiers, antifoams, flavorings, preservatives, solubilizers or colorings.

For an oral administration form, the active compounds are mixed with the additives suitable for this purpose, such as carriers, stabilizers or inert diluents and converted to the suitable dosage forms, such as tablets, coated tablets, hard gelatin capsules, aqueous, alcoholic or oily solutions by the customary methods. Examples of useful inert carriers include gum arabic, magnesia, magnesium carbonate, potassium phosphate, lactose, glucose or starch, in particular corn starch. The preparation may be either in the form of dry granules or in the form of moist granules. Examples of useful oily carriers or useful solvents are vegetable or animal oils, such as sunflower oil or cod liver oil.

For subcutaneous, percutaneous or intravenous administration, the active compounds used, if desired with the substances customary for this purpose, such as solubilizers, emulsifiers or further excipients, are converted to solution, suspension or emulsion. Examples of useful solvents are: water, physiological saline or alcohols, for example ethanol, propanol, glycerol and additionally also sugar solutions such as glucose or mannitol solutions, or else a mixture of the different solvents mentioned.

Examples of suitable pharmaceutical formulations for administration in the form of aerosols or sprays are solutions, suspensions or emulsions of the active ingredient of the formula I in a pharmaceutically acceptable solvent, in particular ethanol or water, or a mixture of such solvents. If required, the formulation may also comprise other pharmaceutical excipients such as surfactants, emulsifiers and stabilizers, and also a propellant gas. Such a preparation typically contains the active ingredient in a concentration of from about 0.1 to 10% by weight, in particular from about 0.3 to 3% by weight.

The dosage of the active ingredient of the formula I to be administered and the frequency of administration depend on the potency and duration of action of the compounds used; additionally also on the nature and severity of the disease to be treated, and also on the gender, age, weight and individual responsiveness of the mammal to be treated.

On average, the daily dose of a compound of the formula I in the case of a patient weighing about 75 kg is at least 0.001 mg/kg, preferably 0.1 mg/kg, up to at most 30 mg/kg, preferably 1 mg/kg, of body weight. In acute situations, for instance immediately after suffering apnetic states in high mountains, even higher dosages may be necessary. Especially in the case of i.v. administration, for instance in a heart attack patient in the intensive care unit, up to 300 mg/kg per day may be necessary. The daily dose can be divided into one or more, for example up to 4, individual doses.

EXPERIMENTAL DESCRIPTIONS AND EXAMPLES

List of abbreviations used:

| | |
|---|---|
| TFA | Trifluoroacetic acid |
| HPLC | High Performance Liquid Chromatography |
| LC-MS | Liquid Chromatography-Mass Spectrometry |
| Rt | Retention time |
| THF | Tetrahydrofuran |
| DMSO | Dimethyl sulfoxide |
| abs. | absolute |
| DMF | Dimethylformamide |
| ACN | Acetonitrile |
| min. | minutes |
| h | hour(s) |
| EDC | N-(3-dimethylaminopropyl)-N'-ethylcarbodiimide |
| AiBN | 2,2'-Azobis(2-methylpropionitrile) |
| NBS | N-bromosuccinimide |
| CI | Chemical ionization |
| ESI | Electrospray ionization |
| m | multiplet |
| d | doublet |
| s | singlet |

General:
Of the epimers at C-4 of the formula I, one epimer is often more active than the other.

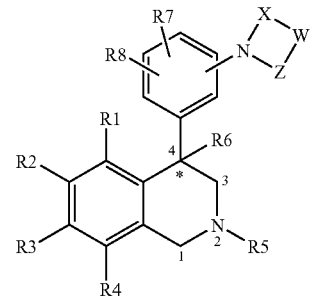

Therefore, some of the enantiomers of the ortho-, meta- and para-amines used (2-, 3- or 4-(1,2,3,4-tetrahydroisoquinolin-4-yl)phenylamine, for example 2-, 3- or 4-(6,8-dichloro-2-methyl-1,2,3,4-tetrahydroisoquinolin-4-yl)phenylamine), were separated on chiral phase, as described in WO2004085404.

Racemic amines of the formula VIII can be prepared as described in WO2004085404, for example: racemic para-amine: 4-(6,8-dichloro-2-methyl-1,2,3,4-tetrahydro-isoquinolin-4-yl)phenylamine (example 1, intermediate 6); meta-amine: 3-(6,8-dichloro-2-methyl-1,2,3,4-tetrahydroisoquinolin-4-yl)phenylamine (example 2, intermediate 1), ortho-amine: 2-(6,8-dichloro-2-methyl-1,2,3,4-tetrahydroisoquinolin-4-yl)phenylamine (example 3, intermediate 5) and subsequently separated into their enantiomers as described in WO2004085404, for example: enantiomerically pure para-amine: (S)-4-(6,8-dichloro-2-methyl-1,2,3,4-tetrahydroisoquinolin-4-yl)phenylamine (example 42, intermediate 1, enantiomer B); meta-amine: (S)-3-(6,8-dichloro-2-methyl-1,2,3,4-tetrahydroisoquinolin-4-yl)phenylamine (example 20, intermediate, enantiomer B); ortho-amine: (R)-2-(6,8-dichloro-2-methyl-1,2,3,4-tetrahydroisoquinolin-4-yl)phenylamine (example 41, intermediate 1, enantiomer B). 2-(6,8-Dichloro-2-cyclopropyl-1,2,3,4-tetrahydroisoquinolin-4-yl)phenylamine and the corresponding (R)- and (S)-enantiomers thereof can be prepared as described in example 41b).

The syntheses described were, unless stated otherwise, performed in the manner known to those skilled in the art under protective gas such as argon in standard reaction vessels such as one-, two- or three-neck flasks which, when required, were equipped with stirrers, coolers, dropping funnels and the like. The solvents were, unless stated otherwise, drawn off on a rotary evaporator in suitable vacuum and at suitable temperature.

Conditions:

Preparative HPLC:
The preparative HPLC was performed under the following conditions:

| | |
|---|---|
| stationary phase: | Merck Purospher RP18 (10 μM) 250 × 25 mm |
| mobile phase: | 90% H$_2$O (0.05% TFA)→ 90% acetonitrile in 40 min; 25 ml/min |

Analytical HPLC/MS
HPLC methods
Method A:

| | |
|---|---|
| stationary phase: | YMC J'sphere ODS H80 20 × 2.1 mm |
| mobile phase: | 90% H$_2$O (0.05% TFA)→ 95% acetonitrile in 1.9 min; |

| | |
|---|---|
| | 95% acetonitrile 0.5 min → 10% acetonitrile in 0.05 min; 1 ml/min. |
| Method B: | |
| stationary phase: | YMC J'sphere ODS H80 20 × 2.1 mm |
| mobile phase: | 96% $H_2O$ (0.05% TFA)→ 95% acetonitrile in 2.0 min; 95% acetonitrile 0.4 min → 4% acetonitrile in 0.05 min; 1 ml/min. |

Mass Spectrometry

The mass spectrometer was coupled directly to the HPLC (LC-MS). The ionization method used, unless stated otherwise, was electrospray ($ESI^+$). The retention times reported relate to the signal maximum of the ion current of the appropriate compound, as was obtained in the LC-MS coupling with the above HPLC conditions.

Example 1

3-[4-(6,8-Dichloro-2-methyl-1,2,3,4-tetrahydroisoquinolin-4-yl)phenyl]-imidazolidine-2,4-dione

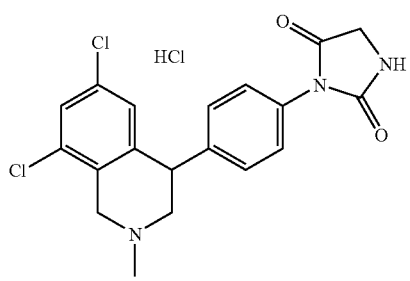

a) Ethyl {3-[4-(6,8-dichloro-2-methyl-1,2,3,4-tetrahydroisoquinolin-4-yl)phenyl]ureido}-acetate hydrochloride

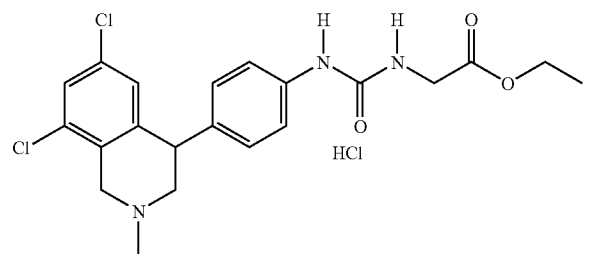

4-(6,8-Dichloro-2-methyl-1,2,3,4-tetrahydroisoquinolin-4-yl)phenylamine (95 mg; preparation as described in WO2004085404) was dissolved in acetonitrile (2 ml) and ethyl isocyanatoacetate (30 mg) was added dropwise with stirring. After 4 hours, the solution was concentrated and the residue purified by means of preparative HPLC. The fractions comprising product were combined, the acetonitrile was removed on a rotary evaporator, and the aqueous residue was neutralized with potassium carbonate and extracted three times with ethyl acetate. Drying over magnesium sulfate was followed by concentration to dryness. The residue was taken up with aqueous hydrochloric acid and freeze-dried. 107 mg of the desired compound were obtained.

LC-MS Rt (A): 1.14 min;
[M+H$^+$]: 436.5 b) 3-[4-(6,8-Dichloro-2-methyl-1,2,3,4-tetrahydroisoquinolin-4-yl)phenyl]imidazolidine-2,4-dione Ethyl {3-[4-(6,8-dichloro-2-methyl-1,2,3,4-tetrahydroisoquinolin-4-yl)phenyl]ureido}-acetate hydrochloride (30 mg) was initially charged. Water (3 ml) and 10% hydrochloric acid (231 µl) were added and subsequently refluxed with stirring for three hours. After cooling and freeze-drying of the reaction solution, a white solid was obtained.

LC-MS Rt (A): 0.98 min;
[M+H$^+$]: 390.4

Example 2

3-[4-((S)-6,8-Dichloro-2-methyl-1,2,3,4-tetrahydroisoquinolin-4-yl)phenyl]-imidazolidine-2,4-dione hydrochloride

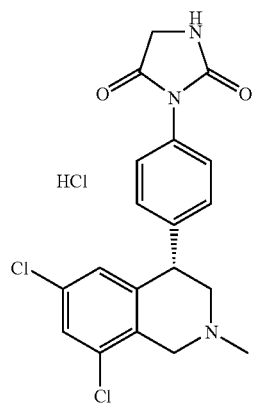

Example 2 was synthesized analogously to example 1. The (S)-4-(6,8-dichloro-2-methyl-1,2,3,4-tetrahydroisoquinolin-4-yl)phenylamine required for this purpose (enantiomer B, preparation as described in WO2004085404) was obtained from the racemate by separation on chiral phase.

LC-MS Rt (B): 0.89 min;
[M+H$^+$]: 390.1

Example 3

3-[3-(6,8-Dichloro-2-methyl-1,2,3,4-tetrahydroisoquinolin-4-yl)phenyl]-imidazolidine-2,4-dione

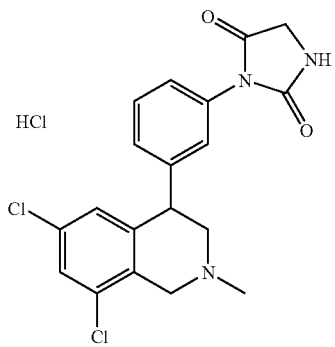

Example 3 was synthesized analogously to example 1. The 3-(6,8-dichloro-2-methyl-1,2,3,4-tetrahydroisoquinolin-4-yl)phenylamine required for this purpose was prepared as described in WO2004085404.

LC-MS Rt (A): 0.96 min;

[M+H⁺]: 390.3

Example 4

3-[3-((S)-6,8-Dichloro-2-methyl-1,2,3,4-tetrahydroisoquinolin-4-yl)phenyl]-imidazolidine-2,4-dione hydrochloride

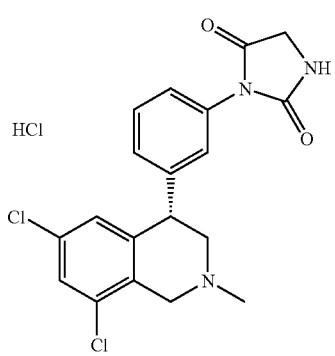

Example 4 was synthesized analogously to example 1. The (S)-3-(6,8-dichloro-2-methyl-1,2,3,4-tetrahydroisoquinolin-4-yl)phenylamine required for this purpose (enantiomer B, preparation as described in WO2004085404) was obtained from the racemate by separation on chiral phase.

LC-MS Rt (B): 0.90 min;

[M+H⁺]: 390.0

Example 5

3-[2-(6,8-Dichloro-2-methyl-1,2,3,4-tetrahydroisoquinolin-4-yl)phenyl]-imidazolidine-2,4-dione hydrochloride

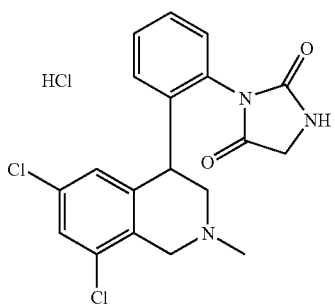

Example 5 was synthesized analogously to example 1. The 2-(6,8-dichloro-2-methyl-1,2,3,4-tetrahydroisoquinolin-4-yl)phenylamine required for this purpose was obtained as described in WO2004085404.

LC-MS Rt (A): 1.04 min;

[M+H⁺]: 390.4

Example 6

3-[2-((R)-6,8-Dichloro-2-methyl-1,2,3,4-tetrahydroisoquinolin-4-yl)phenyl]-imidazolidine-2,4-dione hydrochloride

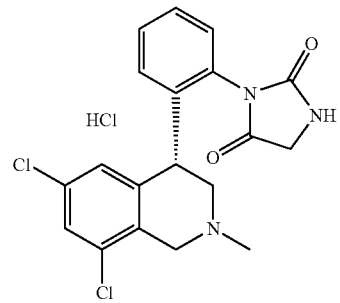

Example 6 was synthesized analogously to example 1. The (R)-2-(6,8-dichloro-2-methyl-1,2,3,4-tetrahydroisoquinolin-4-yl)phenylamine required for this purpose (enantiomer B, preparation as described in WO2004085404) was obtained from the racemate by separation on chiral phase.

LC-MS Rt (B): 0.98 min;

[M+H⁺]: 390.0

Example 7

1-[2-((R)-6,8-Dichloro-2-methyl-1,2,3,4-tetrahydroisoquinolin-4-yl)phenyl]-pyrrolidine-2,5-dione hydrochloride

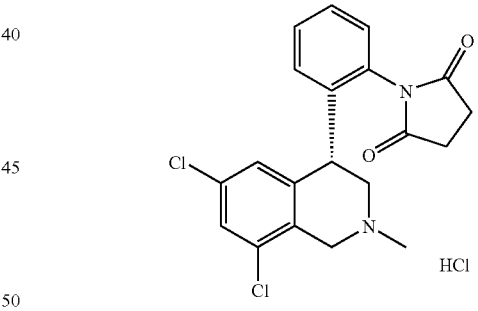

(R)-2-(6,8-Dichloro-2-methyl-1,2,3,4-tetrahydroisoquinolin-4-yl)phenylamine (100 mg; enantiomer B, preparation as described in WO2004085404) was initially charged in a flask together with succinic acid (58 mg). To this was added polyphosphoric acid (approx. 2 ml). The reaction mixture was subsequently stirred at 135° C. After 4 hours, a little more succinic acid (~9 mg) was added. After a further 2 h at 135° C., the mixture was left to stand at room temperature overnight. For workup, the mixture was poured onto ice-water, and the acidic phase was adjusted to pH 10 with saturated potassium carbonate solution and then extracted three times with ethyl acetate. The combined organic phases were washed once with water, dried over magnesium sulfate, filtered and concentrated. The crude product was purified by means of preparative HPLC. The fractions comprising product were combined, the acetonitrile was removed on a rotary evaporator, and the aqueous residue was neutralized with potassium carbonate and extracted three times with ethyl acetate. It was dried over magnesium sulfate, then filtered and concentrated to dryness. The residue was taken up with aqueous hydrochloric acid and freeze-dried.

LC-MS Rt (B): 1.03 min;
[M+H$^+$]: 389.0

Example 8

6,8-Dichloro-4-[4-(1,1-dioxo-1-$\lambda^6$-[1,2,5]thiadiazolidin-2-yl)phenyl]-2-methyl-1,2,3,4-tetrahydroisoquinoline

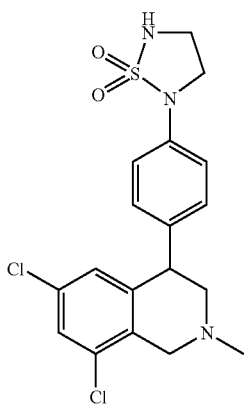

2-Chloroethylamine hydrochloride (75 mg) was stirred with sulfuryl chloride (0.32 ml) in acetonitrile (10 ml) at 75-80° C. overnight. The mixture cooled to room temperature was concentrated and the residue taken up with absolute ether (1 ml). The ether phase comprising the chlorosulfonamide was added dropwise to a solution of 4-(6,8-dichloro-2-methyl-1,2,3,4-tetrahydroisoquinolin-4-yl)phenylamine (110 mg, preparation as described in WO2004085404), absolute diethyl ether (1 ml) and triethylamine (85 µl) at −70° C. After the addition had ended, the reaction mixture was allowed to come to room temperature and stirred for a further 2.5 h. Subsequently, it was admixed with a mixture of water and saturated sodium hydrogencarbonate solution (3:1) and a little more ether was added. The phases were separated and the aqueous phase was extracted twice with diethyl ether. The combined ether phases were dried over magnesium sulfate, filtered and concentrated.

The crude product was purified by means of preparative HPLC. The fractions comprising product were combined, the acetonitrile was removed on a rotary evaporator, and the aqueous residue was neutralized with potassium carbonate and extracted three times with dichloromethane. It was dried over magnesium sulfate, then filtered and concentrated to dryness. A portion of the product thus obtained (20 mg) was dissolved in DMSO (0.5 ml), admixed with potassium carbonate (6.2 mg) and stirred at room temperature for six hours. After storing in a freezer cabinet overnight, the DMSO was removed under high vacuum and the residue admixed with a little water, saturated sodium hydrogencarbonate solution and ether. The phases were separated and the aqueous phase was extracted twice more with diethyl ether. The combined ether phases were dried over magnesium sulfate, filtered and concentrated. The crude product was purified by means of preparative HPLC. The fractions comprising product were combined, the acetonitrile was removed on a rotary evaporator, and the aqueous residue was neutralized with potassium carbonate and extracted three times with dichloromethane. It was dried over magnesium sulfate, then filtered and concentrated to dryness. The residue was taken up with aqueous hydrochloric acid and freeze-dried.

LC-MS Rt (B): 1.02 min;
[M+H$^+$]: 412.1

Starting from the corresponding amines, some of which were used in enantiomerically pure form, and the corresponding dicarboxylic acids, the following compounds were prepared analogously.

| Example | Structure | Salt | Analogously to example | MS [M + H$^+$] | LC-MS Rt [min] |
|---|---|---|---|---|---|
| 9 | 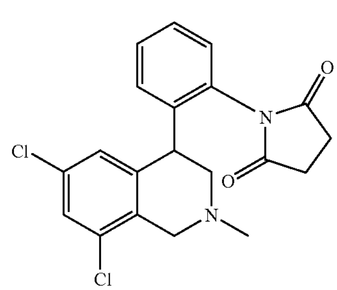 | HCl | 7 | 389.0 (ESI$^+$) | 1.03 (B) |

-continued

| Example | Structure | Salt | Analogously to example | MS [M + H⁺] | LC-MS Rt [min] |
|---|---|---|---|---|---|
| 10 | 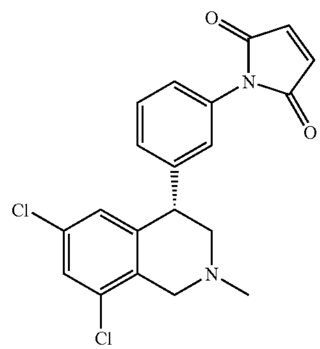 | HCl | 7 | 387.0 (ESI⁺) | 1.05 (B) |
| 11 | 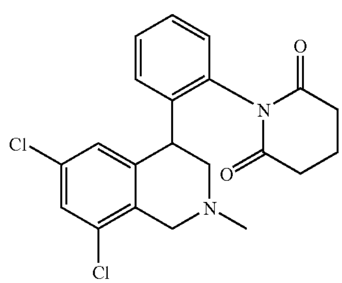 | HCl | 7 | 403.0 (ESI⁺) | 1.06 (B) |
| 12 | 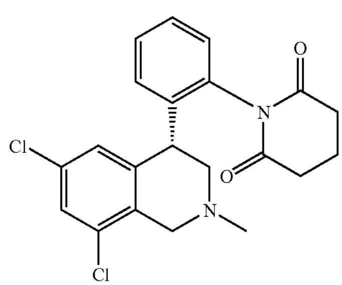 | HCl | 7 | 403.0 (ESI⁺) | 1.04 (B) |
| 13 | 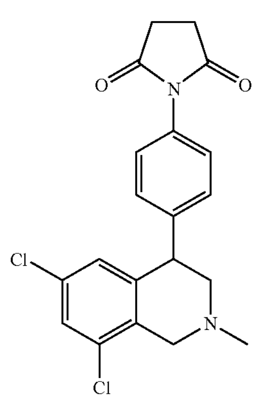 | HCl | 7 | 389.0 (ESI⁺) | 0.97 (B) |

-continued

| Example | Structure | Salt | Analogously to example | MS [M + H⁺] | LC-MS Rt [min] |
|---|---|---|---|---|---|
| 14 | 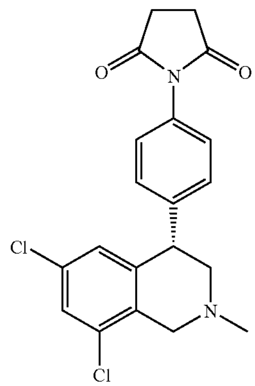 | HCl | 7 | 389.0 (ESI⁺) | 0.96 (B) |
| 15 | 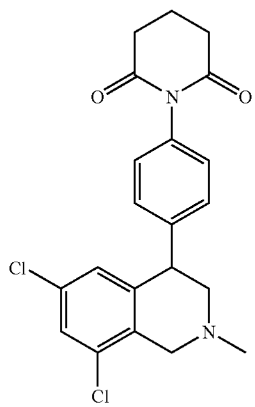 | HCl | 7 | 403.1 (ESI⁺) | 0.97 (B) |
| 16 | 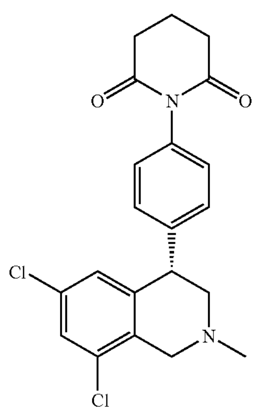 | HCl | 7 | 403.1 (ESI⁺) | 0.96 (B) |
| 17 | 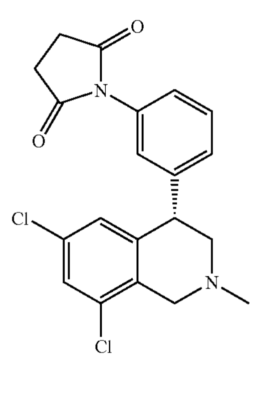 | HCl | 7 | 389.1 (ESI⁺) | 0.97 (B) |

-continued
| Example | Structure | Salt | Analogously to example | MS [M + H⁺] | LC-MS Rt [min] |
|---|---|---|---|---|---|
| 18 | 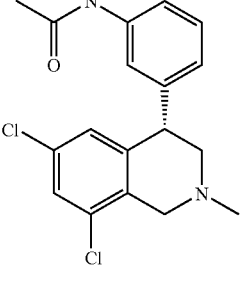 | HCl | 7 | 403.1 (ESI⁺) | 0.98 (B) |
| 19 | 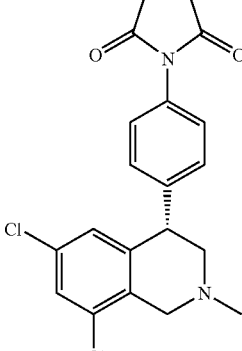 | HCl | 7 | 387.0 (ESI⁺) | 1.05 (B) |
| 20 | 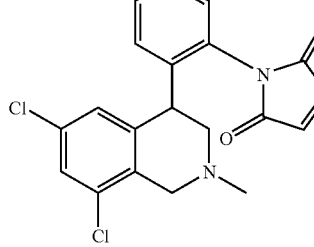 | HCl | 7 | 387.0 (ESI⁺) | 1.12 (B) |
| 21 | 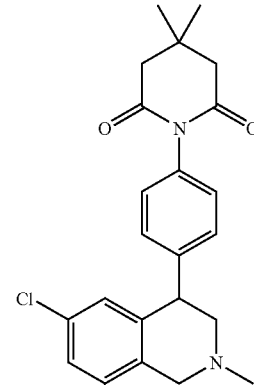 | HCl | 7 | 431.1 (ESI⁺) | 1.20 (B) |

-continued

| Example | Structure | Salt | Analogously to example | MS [M + H⁺] | LC-MS Rt [min] |
|---|---|---|---|---|---|
| 22 | 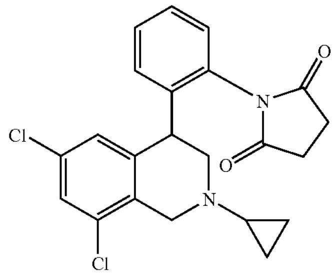 | HCl | 7 | 415.0 (ESI⁺) | 1.19 (B) |
| 23 | 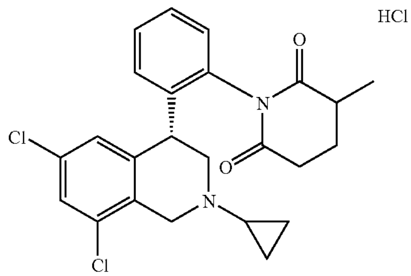 | HCl | 7 | 443.1 (ESI⁺) | 1.31 (B) |
| 24 | 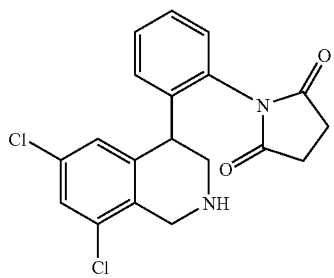 | TFA | 7 | 375.0 (ESI⁺) | 1.04 (B) |
| 25 | 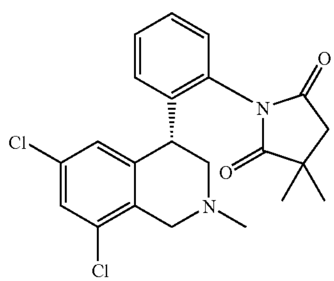 | TFA | 7 | 417.0 (ESI⁺) | 1.15 (B) |
| 26 | 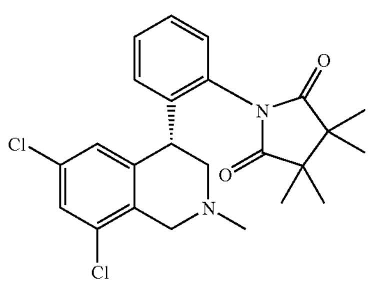 | TFA | 7 | 445.1 (ESI⁺) | 1.24 (B) |

-continued

| Example | Structure | Salt | Analogously to example | MS [M + H⁺] | LC-MS Rt [min] |
|---|---|---|---|---|---|
| 27 | 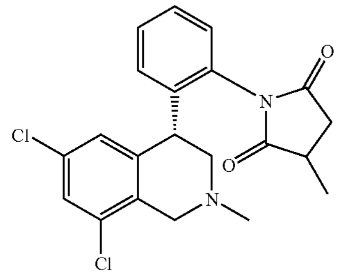 | HCl | 7 | 403.0 (ESI⁺) | 1.07 (B) |
| 28 | 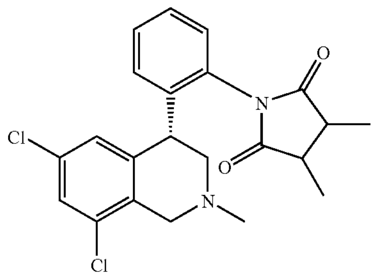 | TFA | 7 | 417.0 (ESI⁺) | 1.16 (B) |
| 29 | 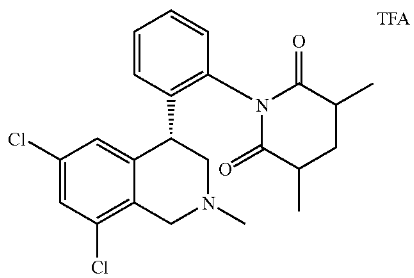 | TFA | 7 | 431.1 (ESI⁺) | 1.19 (B) |
| 30 | 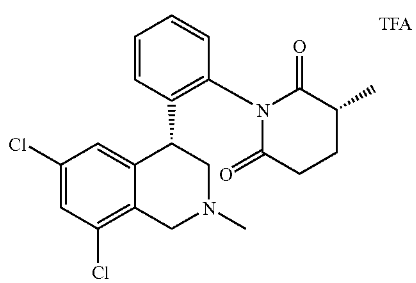 | TFA | 7 | 417.0 (ESI⁺) | 1.15 (B) |
| 31 | 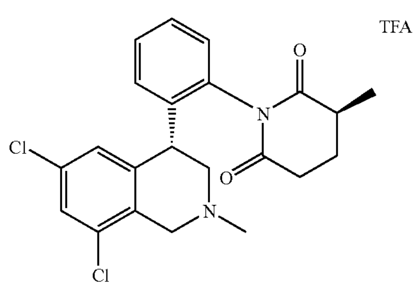 | TFA | 7 | 417.0 (ESI⁺) | 1.13 (B) |

-continued

| Example | Structure | Salt | Analogously to example | MS [M + H+] | LC-MS Rt [min] |
|---|---|---|---|---|---|
| 32 | 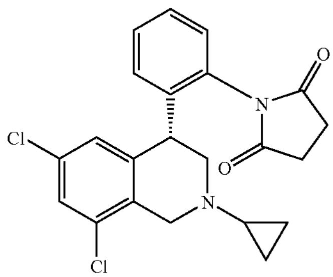 | HCl | 7 | 415.0 (ESI+) | 1.21 (B) |
| 33 | 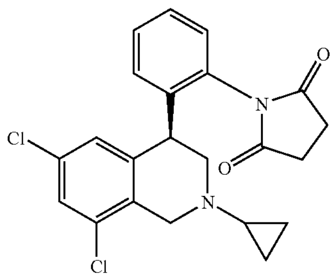 | HCl | 7 | 415.0 (ESI+) | 1.21 (B) |
| 34 | 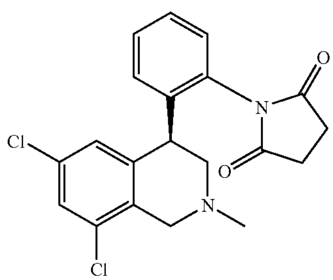 | HCl | 7 | 389.0 (ESI+) | 1.06 (B) |

Example 35

1-[2-((R)-6,8-Dichloro-2-methyl-1,2,3,4-tetrahydroisoquinolin-4-yl)phenyl]-pyrrolidin-2-one trifluoroacetate

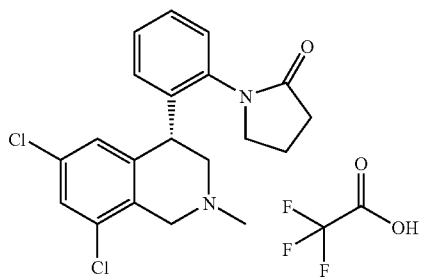

a) N-[2-((R)-6,8-Dichloro-2-methyl-1,2,3,4-tetrahydroisoquinolin-4-yl)phenyl]-4-hydroxybutyramide

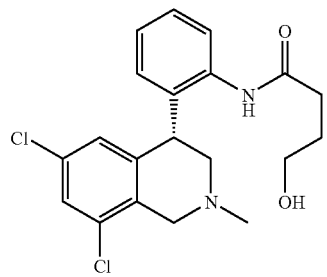

(R)-2-(6,8-Dichloro-2-methyl-1,2,3,4-tetrahydroisoquinolin-4-yl)phenylamine (100 mg, enantiomer B, preparation as described in WO2004085404) was initially charged with γ-butyrolactone (84 mg) in abs. THF (8 ml), and then sodium hexamethyldisilazide (NaHMDS; 2 M/THF; 0.65 ml) was added dropwise at 0° C. within 15 min. After stirring at 0° C. for 10 min, the ice bath was removed and the mixture was stirred for a further 2 h. The reaction was admixed with saturated ammonium chloride solution (0.6 ml), ethyl acetate and water. The phases were separated and the aqueous phase was extracted twice with ethyl acetate. The combined organic phases were washed once with saturated sodium chloride solution, dried over magnesium sulfate, filtered and concentrated. The crude product was purified by means of preparative HPLC. The fractions comprising product were combined, the acetonitrile was removed on a rotary evaporator, and the aqueous residue was neutralized with potassium carbonate and extracted three times with dichloromethane. After the combined dichloromethane phases had been dried over magnesium sulfate, they were filtered and concentrated to dryness.

LC-MS Rt (B): 0.98 min;
[M+H$^+$]: 393.1 b)  1-[2-((R)-6,8-Dichloro-2-methyl-1,2,3,4-tetrahydroisoquinolin-4-yl)phenyl]pyrrolidin-2-one trifluoroacetate N-[2-((R)-6,8-Dichloro-2-methyl-1,2,3,4-tetrahydroisoquinolin-4-yl)phenyl]-4-hydroxy-butyramide (100 mg) was dissolved in absolute THF (4 ml), and triethylamine (77 µl) and a solution of methanesulfonyl chloride (44 µl) in THF (0.5 ml) was added dropwise. After stirring at room temperature for six hours, the THF was drawn off and the residue admixed with saturated sodium hydrogencarbonate solution. After extracting three times with ethyl acetate, the combined organic phases were dried over magnesium sulfate, filtered and concentrated. A portion of the residue (44 mg) was dissolved in absolute THF (2 ml) and the reaction mixture was cooled to 0° C. At this temperature, sodium hexamethyldisilazide (96 µl) was added dropwise within 10 min. Subsequently, the mixture was stirred at 0° C. for another 10 min before the ice bath was removed. After 1.5 h, the reaction was admixed with saturated ammonium chloride solution (0.2 ml) and water. The mixture was then extracted three times with ethyl acetate. The combined organic phases were dried over magnesium sulfate, filtered and concentrated. The crude product was purified by means of preparative HPLC. The fractions comprising product were combined, the acetonitrile was removed on a rotary evaporator, and the aqueous residue was neutralized with potassium carbonate and extracted three times with dichloromethane. After the combined dichloromethane phases had been dried over magnesium sulfate, they were filtered and concentrated to dryness.

LC-MS Rt (B): 1.04 min;
[M+H$^+$]: 375.1

Example 36

1-[2-((R)-6,8-Dichloro-2-methyl-1,2,3,4-tetrahydroisoquinolin-4-yl)phenyl]-pyrrolidin-2-one hydrochloride

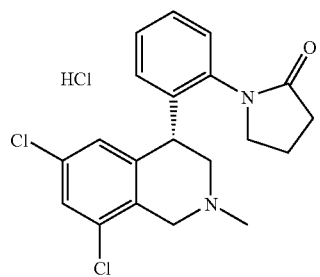

a)  4-Chloro-N-[2-((R)-6,8-dichloro-2-methyl-1,2,3,4-tetrahydroisoquinolin-4-yl)phenyl]-butyramide

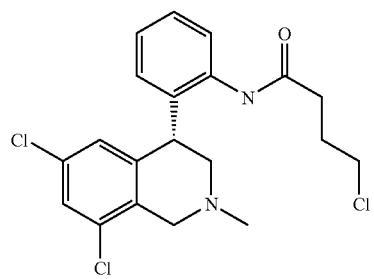

2-((R)-6,8-Dichloro-2-methyl-1,2,3,4-tetrahydroisoquinolin-4-yl)phenylamine (250 mg) was dissolved in abs. THF (20 ml). 4-Chlorobutyryl chloride (115 mg) and triethylamine (208 µl) were added with stirring. The mixture was stirred at room temperature for approx. 3 h. After standing overnight, the reaction mixture was concentrated and the residue purified by means of preparative HPLC. The fractions comprising product were combined, the acetonitrile was removed on a rotary evaporator, and the aqueous residue was neutralized with sodium hydrogencarbonate and extracted three times with ethyl acetate. After the combined ethyl acetate phases had been dried over magnesium sulfate, they were filtered and concentrated to dryness. 290 mg of an oily product were obtained.

LC-MS Rt (B): 1.14 min;
[M+H$^+$]: 411.0 b)  1-[2-((R)-6,8-Dichloro-2-methyl-1,2,3,4-tetrahydroisoquinolin-4-yl)phenyl]pyrrolidin-2-one hydrochloride 4-Chloro-N-[2-((R)-6,8-dichloro-2-methyl-1,2,3,4-tetrahydroisoquinolin-4-yl)phenyl]-butyramide (249 mg) was dissolved in abs. DMSO (10 ml) and finely powdered and dried potassium carbonate (250 mg) was added. With exclusion of moisture, the mixture was stirred vigorously at room temperature for 4 h. After standing overnight, the reaction mixture was diluted with water (50 ml) and then extracted three times with ethyl acetate. The combined extracts were dried over magnesium sulfate, filtered and concentrated. The residue was purified by means of preparative HPLC. The fractions comprising product were combined, the acetonitrile was removed on a rotary evaporator, and the aqueous residue was neutralized with sodium hydrogencarbonate and extracted three times with ethyl acetate. After the combined ethyl acetate phases had been dried over magnesium sulfate, they were filtered and concentrated to dryness. The residue was dissolved in water/acetonitrile and adjusted to pH 2 with 0.1 N HCl. After freeze-drying overnight, the desired product (116 mg) was obtained as a white powder.

LC-MS Rt (B): 1.06 min;
[M+H$^+$]: 375.1

Example 37

1-[2-((R)-6,8-Dichloro-2-cyclopropyl-1,2,3,4-tetrahydroisoquinolin-4-yl)-phenyl]pyrrolidin-2-one

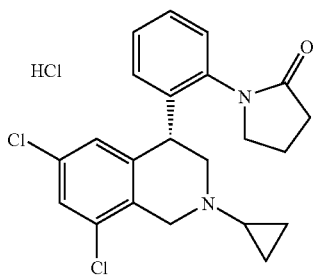

The title compound was synthesized starting from 2-((R)-6,8-dichloro-2-cyclopropyl-1,2,3,4-tetrahydroisoquinolin-4-yl)phenylamine (example 41b) analogously to example 36.

LC-MS Rt (B): 1.12 min;

[M+H$^+$]: 401.0

Example 38

1-[3-((S)-6,8-Dichloro-2-methyl-1,2,3,4-tetrahydroisoquinolin-4-yl)phenyl]-piperidin-2-one

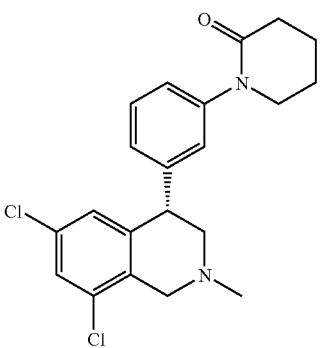

Starting from (S)-3-(6,8-dichloro-2-methyl-1,2,3,4-tetrahydroisoquinolin-4-yl)-phenylamine (enantiomer B, preparation as described in WO2004085404) and δ-valerolactone, 1-[3-((S)-6,8-dichloro-2-methyl-1,2,3,4-tetrahydroisoquinolin-4-yl)-phenyl]piperidin-2-one was synthesized analogously to example 35.

LC-MS Rt (B): 1.05 min;

[M+H$^+$]: 389.1

Example 39

1-[2-((R)-6,8-Dichloro-2-methyl-1,2,3,4-tetrahydroisoquinolin-4-yl)phenyl]-imidazolidin-2-one hydrochloride

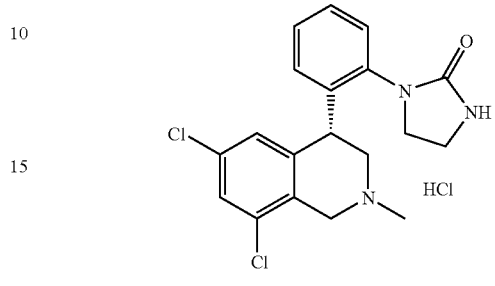

a) 1-(2-Chloroethyl)-3-[2-((R)-6,8-dichloro-2-methyl-1,2,3,4-tetrahydroisoquinolin-4-yl)-phenyl]urea

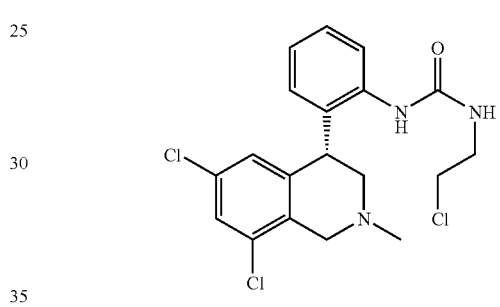

(R)-2-(6,8-Dichloro-2-methyl-1,2,3,4-tetrahydroisoquinolin-4-yl)phenylamine (100 mg, enantiomer B, preparation as described in WO2004085404) was dissolved in absolute dichloromethane (5 ml) and admixed with stirring with 4-nitrophenyl chloroformate (79 mg). After stirring at room temperature for 4 h, the mixture was left to stand overnight. The next day, further 4-nitrophenyl chloroformate (10 mg) was added and the mixture was stirred at room temperature for 1 h. The reaction mixture was concentrated to dryness under reduced pressure and the residue was dissolved in absolute dichloromethane (5 ml). After addition of triethylamine (180 µl), a solution of 2-chloroethylamine hydrochloride (61 mg) in absolute dichloromethane (3 ml) was added dropwise and the mixture was stirred at room temperature for four hours. Subsequently, the mixture was admixed with further methylene chloride and dilute potassium carbonate solution and the organic phase was extracted three times with dilute potassium carbonate solution. After drying over magnesium sulfate and filtration, the organic phase was concentrated and purified by means of preparative HPLC. The fractions comprising product were combined, the acetonitrile was removed on a rotary evaporator, and the aqueous residue was neutralized with saturated sodium hydrogencarbonate solution and extracted three times with ethyl acetate. After the combined ethyl acetate phases had been dried over magnesium sulfate, they were filtered and concentrated to dryness. 50 mg of the desired product were obtained.

LC-MS Rt (B): 1.05 min;

[M+H$^+$]: 412.1 b) 1-[2-((R)-6,8-Dichloro-2-methyl-1,2,3,4-tetrahydroisoquinolin-4-yl)phenyl]-imidazolidin-2-one hydrochloride 1-(2-Chloroethyl)-3-[2-((R)-6,8-dichloro-2-methyl-1,2,3,4-tetrahydroisoquinolin-4-yl)-phenyl]urea (40 mg) was dissolved in absolute DMSO (1 ml) and admixed with stirring with potassium carbonate (14 mg). After stirring at room temperature for four hours, a little more potassium carbonate (7 mg) was added. After being left to stand overnight, the DMSO was removed under reduced pressure, the residue was admixed with a little water and saturated sodium hydrogencarbonate solution and the resulting mixture was subsequently extracted three times with dichloromethane. The combined organic phases were dried over magnesium sulfate, filtered and concentrated. The residue was purified by means of preparative HPLC, although it was not possible to remove one impurity, so that a further chromatography on silica gel followed (100/0 to 88/12 dichloromethane/methanol within 80 min). The clean fractions were combined and concentrated to dryness, and the residue was subsequently freeze-dried with water and a little hydrochloric acid.

LC-MS Rt (B): 1.00 min;
[M+H$^+$]: 376.0

Example 40

1-[2-((R)-6,8-Dichloro-2-methyl-1,2,3,4-tetrahydroisoquinolin-4-yl)phenyl]-1,3-dihydroimidazol-2-one hydrochloride

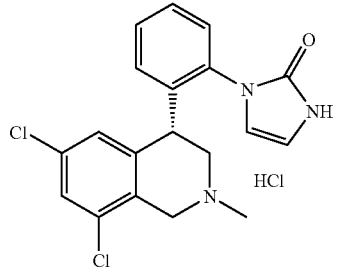

a) 1-[2-((R)-6,8-Dichloro-2-methyl-1,2,3,4-tetrahydroisoquinolin-4-yl)phenyl]-3-(2,2-diethoxyethyl)urea

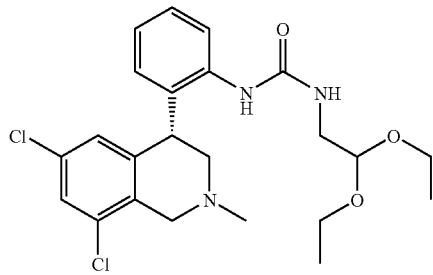

(R)-2-(6,8-Dichloro-2-methyl-1,2,3,4-tetrahydroisoquinolin-4-yl)phenylamine (75 mg, enantiomer B, preparation as described in WO2004085404) was reacted analogously to example 25a) with 4-nitrophenyl chloroformate (64 mg) and subsequently with 2,2-diethoxyethylamine (46 mg).

LC-MS Rt (B): 1.14 min;
[M+H$^+$]: 466.1 b) 1-[2-((R)-6,8-Dichloro-2-methyl-1,2,3,4-tetrahydroisoquinolin-4-yl)phenyl]-1,3-dihydroimidazol-2-one hydrochloride 1-[2-((R)-6,8-Dichloro-2-methyl-1,2,3,4-tetrahydroisoquinolin-4-yl)phenyl]-3-(2,2-diethoxyethyl)urea (65 mg) was dissolved in formic acid (0.4 ml) and stirred at room temperature for 2 hours. Subsequently, the mixture was admixed with water and neutralized with saturated sodium hydrogencarbonate solution. After extracting three times with ethyl acetate, the combined organic phases were dried over magnesium sulfate, filtered, concentrated and purified by means of preparative chromatography. The fractions comprising product were combined, the acetonitrile was removed on a rotary evaporator, and the aqueous residue was neutralized with saturated sodium hydrogencarbonate solution and extracted three times with ethyl acetate. After the combined ethyl acetate phases had been dried over magnesium sulfate, they were filtered and concentrated to dryness. The residue was taken up with aqueous HCl and freeze-dried.

LC-MS Rt (B): 1.05 min;
[M+H$^+$]: 374.0

Example 41

3-[2-((R)-6,8-Dichloro-2-cyclopropyl-1,2,3,4-tetrahydroisoquinolin-4-yl)-phenyl]thiazolidine-2,4-dione

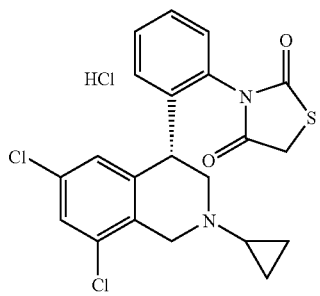

a) 1-(2-Aminophenyl)-2-[cyclopropyl(2,4-dichlorobenzyl)amino]ethanol and 2-{2-[cyclopropyl(2,4-dichlorobenzyl)amino]-1-methoxyethyl}phenylamine

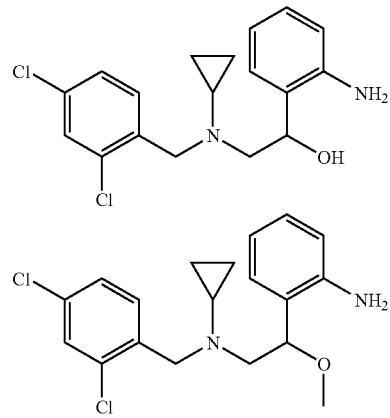

N-(2-{2-[Cyclopropyl(2,4-dichlorobenzyl)amino]-1-hydroxyethyl}phenyl)acetamide (46 g, obtained analogously to example 15 in WO 03 48129) was dissolved in methanol (250 ml). 30% sodium methoxide solution was added thereto with stirring and then the mixture was refluxed for 10 h. To complete the reaction, solid sodium methoxide (10 g) was added and the mixture was refluxed for a further 4 h. For workup, the reaction mixture was subsequently added to 1.5 l of ice-water and eluted three times with ethyl acetate. The combined ethyl acetate phases were washed once with saturated sodium chloride solution, then dried with magnesium sulfate, filtered and concentrated. After chromatographic purification on silica gel, 14 g of 1-(2-aminophenyl)-2-[cyclopropyl(2,4-dichlorobenzyl)amino]ethanol LC-MS Rt (B): 1.03 min;
[M+H$^+$]: 351.0,
13.8 g of 2-{2-[cyclopropyl(2,4-dichlorobenzyl)amino]-1-methoxyethyl}phenylamine
LC-MS Rt (B): 1.18 min;
[M+H$^+$]: 365.0 and 5.5 g of a mixed fraction of the two products were obtained.

The three fractions can all, as described below for 1-(2-aminophenyl)-2-[cyclopropyl-(2,4-dichlorobenzyl)amino]ethanol under b), be cyclized with sulfuric acid to give 2-(6,8-dichloro-2-cyclopropyl-1,2,3,4-tetrahydroisoquinolin-4-yl)phenylamine.

b) 2-((R)-6,8-Dichloro-2-cyclopropyl-1,2,3,4-tetrahydroisoquinolin-4-yl)phenylamine and 2-((S)-6,8-dichloro-2-cyclopropyl-1,2,3,4-tetrahydroisoquinolin-4-yl)phenylamine

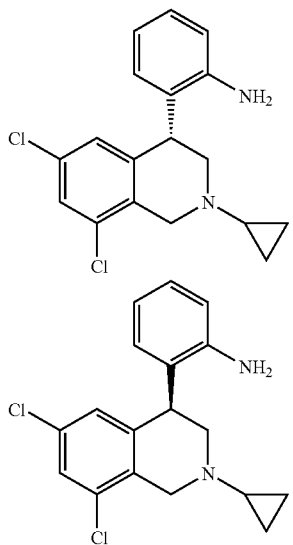

1-(2-Aminophenyl)-2-[cyclopropyl(2,4-dichlorobenzyl) amino]ethanol (14 g) was dissolved in dichloromethane (250 ml) and cooled to 0° C. with stirring. Under cold conditions, conc. sulfuric acid (50 ml) was added dropwise. After the addition had ended, the mixture was stirred at room temperature for approx. 7 h and then at 45° C. for 2 h, in the course of which the dichloromethane evaporated slowly. After standing at room temperature overnight, the reaction was completed by again adding sulfuric acid (5 ml) and keeping the temperature at 65° C. for 12 h. Afterward, the reaction mixture was added to ice-water and adjusted to pH 11 with 10 N sodium hydroxide solution. The water phase was extracted three times with dichloromethane. The combined extracts were dried over magnesium sulfate, filtered and concentrated. The crude product (12.3 g) was chromatographed on silica gel (1:1 to 4:1 ethyl acetate/n-heptane). The resulting purified racemic product (10.7 g) was subsequently separated into its enantiomers by means of chiral HPLC (Chiralpak ADH/45, eluent: 20:1:1 heptane/isopropanol/methanol+0.1% TFA).

7 g of the 2-((R)-6,8-dichloro-2-cyclopropyl-1,2,3,4-tetrahydroisoquinolin-4-yl)-phenylamine P1 which elutes first and 6 g of the more slowly eluting 2-((S)-6,8-dichloro-2-cyclopropyl-1,2,3,4-tetrahydroisoquinolin-4-yl)phenylamine P2 were obtained in the form of their double TFA salts.

Chiral HPLC:
Column: Chiralpak ADH/45, 250×4.6 mm;
Eluent: 20/1/1 heptane/isopropanol/methanol+0.1% TFA
Flow rate: 1 ml/min at 30° C.
P1: Rt: 7.27 min
P2: Rt: 12.81 min c) Phenyl [2-((R)-6,8-dichloro-2-cyclopropyl-1,2,3,4-tetrahydroisoquinolin-4-yl)phenyl]-thiocarbamate

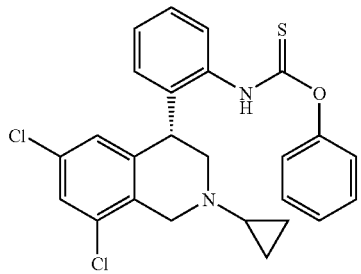

2-((R)-6,8-Dichloro-2-cyclopropyl-1,2,3,4-tetrahydroisoquinolin-4-yl)phenylamine (300 mg) was dissolved in absolute THF (5 ml) and phenyl chlorothioformate (75 µl) dissolved in absolute THF (1 ml) was added dropwise. The reaction mixture stirred at room temperature for 4 h and stood overnight. The solvent was then removed and the residue purified by means of preparative HPLC. The fractions comprising product were combined, the acetonitrile was removed on a rotary evaporator, and the aqueous residue was neutralized with saturated sodium hydrogencarbonate solution and extracted three times with ethyl acetate. After the combined ethyl acetate phases had been dried over magnesium sulfate, they were filtered and concentrated to dryness.

LC-MS Rt (B): 1.87 min;
[M+H$^+$]: 469.0 d) 3-[2-((R)-6,8-Dichloro-2-cyclopropyl-1,2,3,4-tetrahydroisoquinolin-4-yl)phenyl]-thiazolidine-2,4-dione Phenyl [2-((R)-6,8-dichloro-2-cyclopropyl-1,2,3,4-tetrahydroisoquinolin-4-yl)phenyl]-thiocarbamate (50 mg) was dissolved in 30% sodium methoxide solution in methanol (5 ml). For dissolution, the mixture was heated gently with a hot-air gun. The clear solution was stirred at room temperature for approx. 3 h and left to stand overnight. Subsequently, the reaction mixture was diluted with water and extracted three times with ethyl acetate. The combined extracts were dried with magnesium sulfate, filtered and concentrated. The crude product thus obtained (45 mg) was dissolved in absolute methylene chloride (3.5 ml) and bromoacetyl chloride (16.5 mg) was added. The mixture was stirred at room temperature with exclusion of moisture for 3 h. After standing overnight in a freezer cabinet, the solvent and the excess acid chloride were evaporated off and the residue was purified by means of preparative HPLC. The fractions comprising product were combined, the acetonitrile was removed on a rotary evaporator, and the aqueous residue was neutralized with saturated sodium hydrogencarbonate solution and extracted three times with ethyl acetate. After the combined ethyl acetate phases had been dried over magnesium sulfate, they were filtered and concentrated to dryness. A portion (12 mg) of the resulting residue (15 mg) was dissolved in water/acetonitrile, a little hydrochloric acid was added and the clear solution was freeze-dried overnight.

LC-MS Rt (B): 1.40 min;

[M+H$^+$]: 433.0

Example 42

3-[2-((R)-6,8-Dichloro-2-methyl-1,2,3,4-tetrahydroisoquinolin-4-yl)phenyl]-thiazolidine-2,4-dione

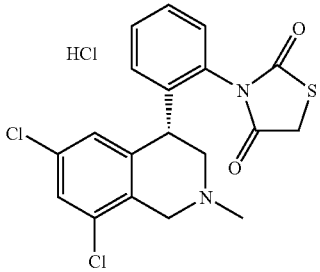

(R)-2-(6,8-Dichloro-2-methyl-1,2,3,4-tetrahydroisoquinolin-4-yl)phenylamine (enantiomer B, preparation as described in WO2004085404) was reacted analogously to example 41. The crude product exhibited a double peak of identical mass in the LC-MS, so that the two products were separated by means of preparative HPLC and subsequently identified. In addition to a contaminated fraction, the two rotational isomers P1 and P2 were isolated.

P1:

LC-MS Rt (B): 1.09 min;

[M+H$^+$]: 407.0

$^1$H NMR (500 MHz, DMSO-d6): 7.51-7.28 (m, 4H), 7.11 (m, 1H), 6.72 (s, 1H), 4.51 (d, 15 Hz, 1H), 4.34 (d, 15 Hz, 1H), 4.18 (m, 1H), 3.64 (d, 15 Hz, 1H), 3.50 (d, 15 Hz, 1H), 2.70 (m, 1H), 2.49 (m, with DMSO), 2.33 (s, 3H) [in ppm]

P2:

LC-MS Rt (B): 1.14 min;

[M+H$^+$]: 407.0

$^1$H NMR (500 MHz, DMSO-d6): 7.52-7.26 (m, 4H), 7.19-7.09 (m, 1H), 6.72 (s, 1H), 4.49 (d, 15 Hz, 1H), 4.35 (d, 15 Hz, 1H), 4.12 (m, 1H), 3.65 (d, 15 Hz, 1H), 3.50 (d, 15 Hz, 1H), 2.72 (m, 1H), 2.48 (m, with DMSO), 2.33 (s, 3H) [in ppm]

Alternative Synthesis:

When chloroacetyl chloride was used instead of bromoacetyl chloride, mainly P2 was obtained which, according to preparative HPLC, was only slightly contaminated with P1 (<10% according to $^1$H NMR).

Example 43

3-[2-((R)-6,8-Dichloro-2-methyl-1,2,3,4-tetrahydroisoquinolin-4-yl)phenyl]-oxazolidine-2,4-dione

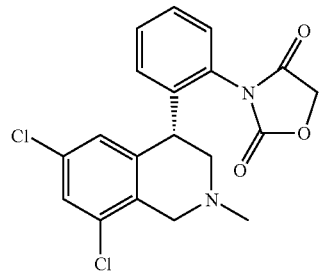

a) [2-((R)-6,8-Dichloro-2-methyl-1,2,3,4-tetrahydroisoquinolin-4-yl)phenyl-carbamoyl]methyl acetate

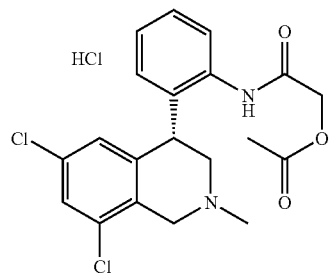

(R)-2-(6,8-Dichloro-2-methyl-1,2,3,4-tetrahydroisoquinolin-4-yl)phenylamine (300 mg, enantiomer B, preparation as described in WO2004085404) was dissolved in absolute THF (10 ml) and admixed at room temperature with stirring with sodium hexamethyl-disilazide solution (0.5 ml; 2 M in THF). After 30 min, acetoxyacetyl chloride (77 µl) was added and the mixture was stirred at room temperature for 2 h. Subsequently, the reaction mixture was concentrated, the residue was dissolved in ethyl acetate/water and basified with sodium hydrogencarbonate solution, and the phases were separated. The aqueous phase was extracted three times with ethyl acetate. The combined extracts were dried over magnesium sulfate, filtered and concentrated. 380 mg of the desired product were obtained. 40 mg thereof were dissolved in acetonitrile/water, acidified with 0.1 N hydrochloric acid and freeze-dried.

LC-MS Rt (B): 1.02 min;

[M+H$^+$]: 407.0 b) N-[2-((R)-6,8-Dichloro-2-methyl-1,2,3,4-tetrahydroisoquinolin-4-yl)phenyl]-2-hydroxyacetamide

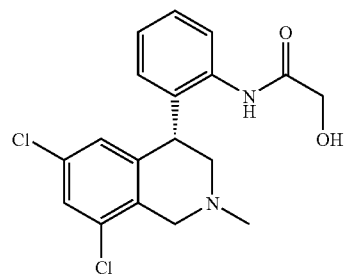

[2-((R)-6,8-Dichloro-2-methyl-1,2,3,4-tetrahydroisoquinolin-4-yl)phenyl-carbamoyl]methyl acetate (180 mg) was dissolved in methanol (5 ml). With stirring, potassium carbonate (305 mg, finely powdered) was added and the mixture was then stirred efficiently at room temperature for 4 h. Subsequently, the solvent was evaporated off, and the residue was taken up in ethyl acetate and washed three times with water. The ethyl acetate phase was dried with magnesium sulfate, filtered and concentrated. 160 mg of the desired product were obtained.

LC-MS Rt (B): 0.94 min;

[M+H⁺]: 365.0 c) 3-[2-((R)-6,8-Dichloro-2-methyl-1,2,3,4-tetrahydroisoquinolin-4-yl)phenyl]-oxazolidine-2,4-dione N-[2-((R)-6,8-Dichloro-2-methyl-1,2,3,4-tetrahydroisoquinolin-4-yl)phenyl]-2-hydroxy-acetamide (20 mg) was dissolved in absolute THF (2 ml), and reacted at room temperature with sodium hexamethyldisilazide solution (0.5 ml; 2 M in THF) with stirring. Afterward, 1,1-carbonyldiimidazole (13 mg) was added and the mixture was stirred at room temperature for 2 h. After standing overnight, the reaction mixture was concentrated, the residue was dissolved in ethyl acetate/water and basified with sodium hydrogencarbonate solution, and the phases were separated. The aqueous phase was extracted three times with ethyl acetate. The combined extracts were dried with magnesium sulfate, filtered and concentrated. The residue was purified by means of preparative HPLC. The fractions comprising product were combined, the acetonitrile was removed on a rotary evaporator, and the aqueous residue was neutralized with saturated sodium hydrogencarbonate solution and extracted three times with ethyl acetate. After the combined ethyl acetate phases had been dried over magnesium sulfate, they were filtered and concentrated to dryness. The residue was dissolved in water/acetonitrile and the clear solution was freeze-dried overnight. 10 mg of the desired product were obtained.

LC-MS Rt (B): 1.09 min;

[M+H⁺]: 391.0

Example 43a

3-[2-((R)-6,8-Dichloro-2-cyclopropyl-1,2,3,4-tetrahydroisoquinolin-4-yl)-phenyl]oxazolidine-2,4-dione hydrochloride

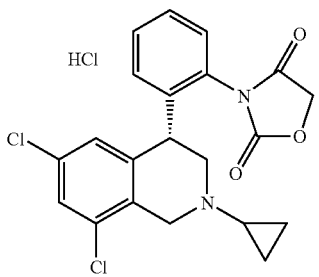

Analogously to the sequence in example 43, 25 mg of the title compound were synthesized. Trichloromethyl chloroformate was used in the cyclization step instead of 1,1-carbonyldiimidazole and the freeze drying was carried out in the presence of hydrochloric acid. LCMS-Rt (B): 1.31 min;

[M+H⁺]: 417.0

Example 44

4-[2-((R)-6,8-Dichloro-2-methyl-1,2,3,4-tetrahydroisoquinolin-4-yl)phenyl]-morpholine-3,5-dione trifluoroacetic acid salt

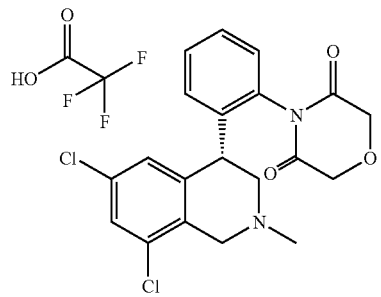

a) 4 {[2-((R)-6,8-Dichloro-2-methyl-1,2,3,4-tetrahydroisoquinolin-4-yl)phenyl-carbamoyl]methoxy}acetic acid trifluoroacetic acid salt

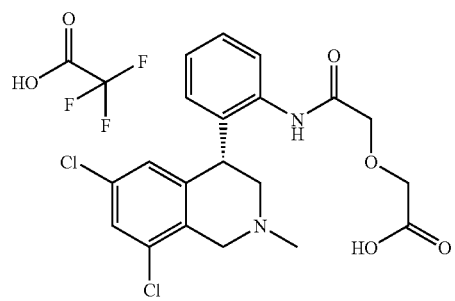

(R)-2-(6,8-Dichloro-2-methyl-1,2,3,4-tetrahydroisoquinolin-4-yl)phenylamine (70 mg, enantiomer B, preparation as described in WO2004085404) was dissolved in absolute dichloromethane (5 ml) with stirring and admixed with diglycolic anhydride (27 mg).

The mixture was stirred at room temperature for several hours and left to stand overnight. After addition of further diglycolic anhydride (26 mg), the mixture was stirred for 10 h and left to stand overnight. After the solvent had been removed, the residue was purified by means of preparative HPLC. The fractions comprising product were combined and the acetonitrile was removed on a rotary evaporator and the aqueous residue was freeze-dried.

LC-MS Rt (B): 0.93 min;

[M+H⁺]: 423.1 b) 4-[2-((R)-6,8-Dichloro-2-methyl-1,2,3,4-tetrahydroisoquinolin-4-yl)phenyl]-morpholine-3,5-dione trifluoroacetic acid salt 4 {[2-((R)-6,8-Dichloro-2-methyl-1,2,3,4-tetrahydroisoquinolin-4-yl)phenylcarbamoyl]-methoxy}acetic acid trifluoroacetic acid salt (50 mg) was dissolved in absolute dichloromethane (2 ml) with stirring and admixed with Hünig's base (46 µl). EDC (22 mg) was then added and the mixture was stirred at room temperature for several hours. After standing overnight, further EDC (22 mg) and Hünig's base (46 µl) were added. After 24 h, the solvent was removed and the residue purified by means of preparative HPLC. The product-containing fractions were combined, freed of acetonitrile and freeze-dried.

LC-MS Rt (B): 1.07 min;
[M+H⁺]: 405.0

Example 45

3-[2-((R)-6,8-Dichloro-2-cyclopropyl-1,2,3,4-tetrahydroisoquinolin-4-yl)-phenyl]oxazolidin-2-one

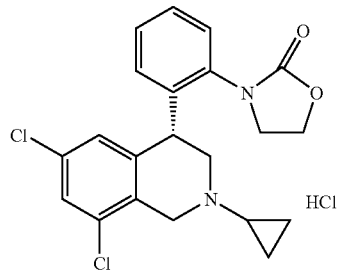

a) 2-Chloroethyl[2-((R)-6,8-dichloro-2-cyclopropyl-1,2,3,4-tetrahydroisoquinolin-4-yl)-phenyl]carbamate

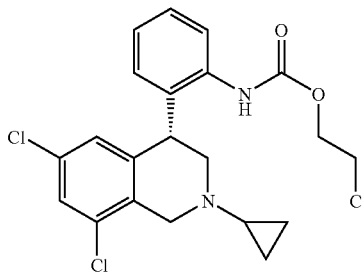

2-((R)-6,8-Dichloro-2-cyclopropyl-1,2,3,4-tetrahydroisoquinolin-4-yl)phenylamine (400 mg) was dissolved in absolute THF (25 ml), and 2-chloroethyl chloroformate (102 mg) was added with stirring. After stirring at room temperature for 3 h, the mixture was left to stand overnight. The solvent was then removed and the residue purified by means of preparative HPLC. The fractions comprising product were combined, the acetonitrile was removed on a rotary evaporator, and the aqueous residue was neutralized with saturated sodium hydrogencarbonate solution and extracted three times with ethyl acetate. After the combined ethyl acetate phases had been dried over magnesium sulfate, they were filtered and concentrated to dryness. 380 mg of the desired product were obtained.

LC-MS Rt (B): 1.66 min;
[M+H⁺]: 439.0 b) 3-[2-((R)-6,8-Dichloro-2-cyclopropyl-1,2,3,4-tetrahydroisoquinolin-4-yl)phenyl]-oxazolidin-2-one2-Chloroethyl[2-((R)-6,8-dichloro-2-cyclopropyl-1,2,3,4-tetrahydroisoquinolin-4-yl)phenyl]carbamate (320 mg) was dissolved in absolute THF (20 ml). With stirring, sodium hydride (35 mg) was added. After stirring at room temperature for 2 h, the reaction mixture was concentrated, and the residue was dissolved in ethyl acetate and washed twice with water. The ethyl acetate phase was dried over magnesium sulfate, filtered and concentrated. The residue was purified by means of preparative HPLC. The fractions comprising product were combined, the acetonitrile was removed on a rotary evaporator, and the aqueous residue was neutralized with saturated sodium hydrogencarbonate solution and extracted three times with ethyl acetate. After the combined ethyl acetate phases had been dried over magnesium sulfate, they were filtered and concentrated to dryness. The residue was dissolved in acetonitrile/water, acidified with 0.1 N hydrochloric acid and freeze-dried. 176 mg of the desired product were obtained as the hydrochloride.

LC-MS Rt (B): 1.16 min;
[M+H⁺]: 403.0

Example 46

3-[2-((R)-6,8-Dichloro-2-methyl-1,2,3,4-tetrahydroisoquinolin-4-yl)phenyl]-oxazolidin-2-one

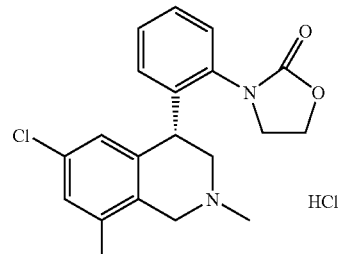

a) 2-Chloroethyl[2-((R)-6,8-dichloro-2-methyl-1,2,3,4-tetrahydroisoquinolin-4-yl)-phenyl]carbamate

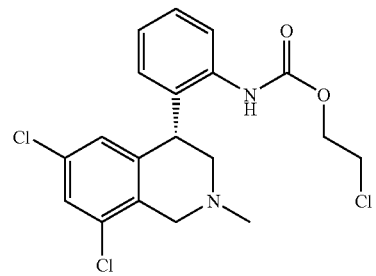

Analogously to example 45a), (R)-2-(6,8-dichloro-2-methyl-1,2,3,4-tetrahydro-isoquinolin-4-yl)phenylamine (300 mg, enantiomer B, preparation as described in WO2004085404) was reacted with 2-chloroethyl chloroformate (140 mg). 400 mg of the desired product were obtained.

LC-MS Rt (B): 1.15 min;
[M+H⁺]: 413.0 b) 3-[2-((R)-6,8-Dichloro-2-methyl-1,2,3,4-tetrahydroisoquinolin-4-yl)phenyl]oxazolidin-2-one Analogously to example 45b), 2-chloroethyl[2-((R)-6,8-dichloro-2-methyl-1,2,3,4-tetra-hydroisoquinolin-4-yl)phenyl]carbamate (340 mg) was reacted with sodium hydride (39 mg). 230 mg of the desired product were obtained as the hydrochloride.

LC-MS Rt (B): 1.01 min;
[M+H⁺]: 377.0

Example 47

(S)-1-[2-((R)-6,8-Dichloro-2-methyl-1,2,3,4-tetrahydroisoquinolin-4-yl)-phenyl]-3-hydroxypyrrolidine-2,5-dione

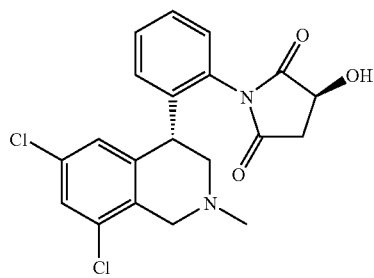

((S)-5-Oxo-2-trichloromethyl[1,3]dioxolan-4-yl)acetic acid (171 mg, see Synthesis 2002, 2165) and thionyl chloride (2 ml) were initially charged and heated to reflux with stirring for 4 h. Subsequently, the excess thionyl chloride was distilled off on a Rotavapor, the residue was dissolved in absolute toluene (14 ml), (R)-2-(6,8-dichloro-2-methyl-1,2,3,4-tetrahydroisoquinolin-4-yl)phenylamine and triethylamine (0.91 ml) were added and the mixture was refluxed for 2 h. After standing overnight, the reaction mixture was concentrated, and the residue was admixed with ethyl acetate/water, adjusted to pH 8 with sodium hydrogencarbonate solution and washed three times with saturated sodium chloride solution. The ethyl acetate phase was dried with magnesium sulfate, filtered and concentrated. The residue was recrystallized from ethyl acetate/heptane. 65 mg of the desired compound were obtained, which exhibits rotational isomerism. However, only a weak, unquantifiable splitting was found in the LC-MS.

LC-MS Rt (B): 1.02 min;
[M+H⁺]: 405.0

Example 48

(R)-1-[2-((R)-6,8-Dichloro-2-methyl-1,2,3,4-tetrahydroisoquinolin-4-yl)-phenyl]-3-hydroxypyrrolidine-2,5-dione

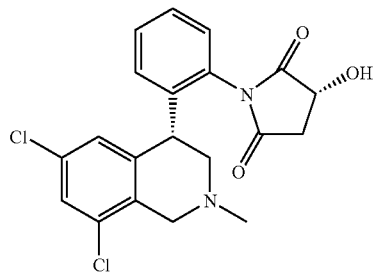

((R)-5-Oxo-2-trichloromethyl[1,3]dioxolan-4-yl)acetic acid (214 mg, see Synthesis 2002, 2165) and thionyl chloride (2.5 ml) were initially charged and heated to reflux with stirring for 4 h. Subsequently, the excess thionyl chloride was distilled off on a Rotavapor, the residue was dissolved in absolute toluene (18 ml), (R)-2-(6,8-dichloro-2-methyl-1,2,3,4-tetrahydroisoquinolin-4-yl)phenylamine (250 mg) and triethylamine (1.13 ml) were added and the mixture was refluxed for 2 h. Subsequently, the reaction mixture was concentrated, and the residue was admixed with ethyl acetate/water, adjusted to pH 8 with sodium hydrogencarbonate solution and washed three times with saturated sodium chloride solution. The ethyl acetate phase was dried with magnesium sulfate, filtered and concentrated. Subsequent crystallization from ethyl acetate/n-heptane afforded 240 mg of the desired product, which exhibits rotational isomerism, so that two signals of identical mass were found in the LC-MS.

LC-MS Rt (B): 0.99 and 1.04 min;
[M+H⁺]: 405.0

Example 49

(R)-1-[2-((R)-6,8-Dichloro-2-cyclopropyl-1,2,3,4-tetrahydroisoquinolin-4-yl)phenyl]-3-hydroxypyrrolidine-2,5-dione

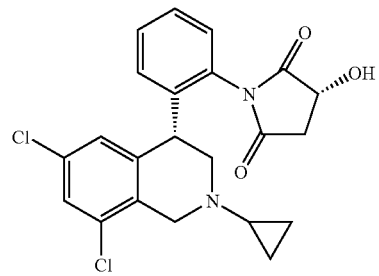

((R)-5-Oxo-2-trichloromethyl[1,3]dioxolan-4-yl)acetic acid (94 mg, see Synthesis 2002, 2165) and thionyl chloride (2 ml) were initially charged and heated to reflux with stirring for 4 h. The excess thionyl chloride was distilled off on a Rotavapor and the residue was dissolved in absolute toluene (15 ml). 2-((R)-6,8-Dichloro-2-cyclopropyl-1,2,3,4-tetrahydroisoquinolin-4-yl)phenylamine trifluoroacetic acid salt (200 mg) was added in solid form, followed by triethylamine (0.5 ml). Subsequently, the mixture was stirred at room temperature for 2 h, then at 60° C. for 1 h, then at 80° C. for 2 h and finally at 100° C. for 6 h. After cooling and removal of the solvent, the mixture was purified by means of preparative HPLC. The fractions comprising product were combined, the acetonitrile was removed on a rotary evaporator and the aqueous residue was freeze-dried. For further workup, the mixture was then purified further on silica gel (100:0 to 90:10 dichloromethane/methanol). The clean fractions were combined and freed of solvent. Freeze-drying from water/acetonitrile afforded 20 mg of the desired product.

LC-MS Rt (B): 1.15 min;
[M+H⁺]: 431.0

Example 50

(S)-1-[2-((R)-6,8-Dichloro-2-cyclopropyl-1,2,3,4-tetrahydroisoquinolin-4-yl)phenyl]-3-hydroxypyrrolidine-2,5-dione

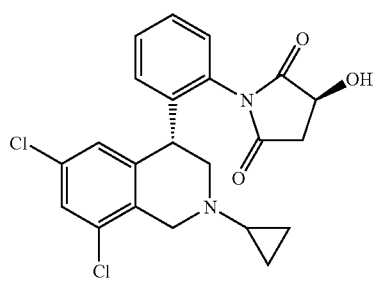

Analogously to example 49, ((R)-5-oxo-2-trichloromethyl[1,3]dioxolan-4-yl)acetic acid (94 mg, see Synthesis 2002, 2165), thionyl chloride (2 ml) and 2-((R)-6,8-dichloro-2-cyclopropyl-1,2,3,4-tetrahydroisoquinolin-4-yl)phenylamine trifluoroacetic acid salt (200 mg) were reacted. The freeze-drying from water/acetonitrile afforded 31 mg of the desired product.

LC-MS Rt (B): 1.13 min;
[M+H$^+$]: 413.0

Example 51

(R)-6,8-Dichloro-4-[2-(1,1-dioxo-1-$\lambda^6$-isothiazolidin-2-yl)phenyl]-2-methyl-1,2,3,4-tetrahydroisoquinoline hydrochloride

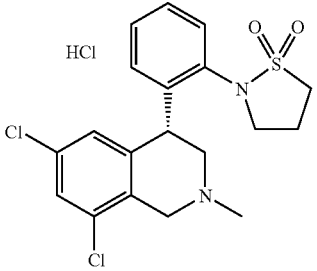

(R)-2-(6,8-Dichloro-2-methyl-1,2,3,4-tetrahydroisoquinolin-4-yl)phenylamine (100 mg) was initially charged in absolute THF (8 ml) and 3-chloropropanesulfonyl chloride (116 mg, dissolved in absolute THF (1.5 ml)) was added dropwise at room temperature and the reaction mixture was subsequently refluxed for 16 hours. To complete the reaction, chloropropanesulfonyl chloride (8 mg) was added once again, followed by sodium hexamethyldisilazide solution (0.2 ml; 2 M in THF). After stirring at room temperature for 30 min and subsequent refluxing, the reaction was completed by adding a further equivalent of sodium hexamethyldisilazide solution and refluxing again. Subsequently, the mixture was admixed with water at room temperature and extracted three times with ethyl acetate. The combined ethyl acetate phases were dried over magnesium sulfate, filtered and concentrated. The residue was subsequently purified by means of preparative HPLC. The fractions comprising product were combined, the acetonitrile was removed on a rotary evaporator, and the aqueous residue was neutralized with saturated sodium hydrogencarbonate solution and extracted three times with ethyl acetate. After the combined ethyl acetate phases had been dried over magnesium sulfate, they were filtered and concentrated to dryness. The residue was taken up with water/hydrochloric acid and freeze-dried. 12 mg of the title compound were obtained.

LC-MS Rt (B): 1.05 min;
[M+H$^+$]: 411.0

Example 52

1-[2-((R)-6,8-Dichloro-1,2,3,4-tetrahydroisoquinolin-4-yl)phenyl]-pyrrolidine-2,5-dione trifluoroacetic acid salt

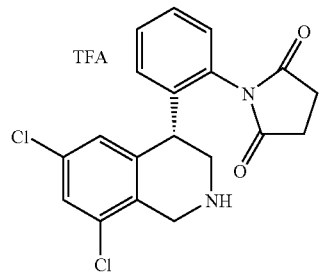

a) N-{2-[2-(2,4-Dichlorobenzylamino)-1-hydroxyethyl]phenyl}acetamide

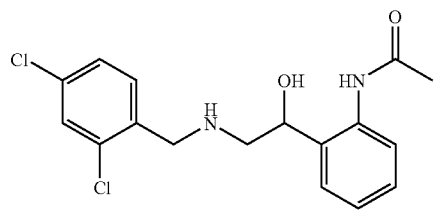

2,4-Dichlorobenzylamine (2.1 ml) was dissolved in absolute ethanol (20 ml) and N-[2-(2-bromoacetyl)phenyl]acetamide (2 g), dissolved in absolute ethanol (50 ml), was added dropwise at room temperature with stirring. After 30 min, sodium borohydride (600 mg) was added with ice cooling and stirred for a further 1.5 h. Subsequently, the solvent was removed and the residue taken up in an ethyl acetate/water mixture. The phases were separated and the aqueous phase extracted three times with ethyl acetate. The combined organic phases were dried over magnesium sulfate, filtered and concentrated. The residue was purified by means of preparative chromatography. The fractions comprising product were combined, the acetonitrile was removed on a rotary evaporator and the aqueous residue was basified with potassium carbonate and extracted three times with ethyl acetate. The combined organic phases were dried over magnesium sulfate, filtered and concentrated. 720 mg of the title compound were obtained.

LC-MS Rt (B): 0.93 min;
[M+H$^+$]: 353.0 b) 1-(2-Aminophenyl)-2-(2,4-dichlorobenzylamino)ethanol

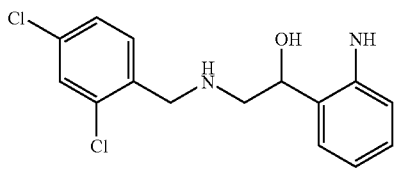

N-{2-[2-(2,4-Dichlorobenzylamino)-1-hydroxyethyl]phenyl}acetamide (100 mg) was dissolved in methanol (5 ml) and admixed with sodium methoxide solution (0.3 ml; 30% in methanol). After reflux for 6 h, the reaction mixture was poured onto ice-water, neutralized with 2 N hydrochloric acid and extracted three times with ethyl acetate. The combined organic phases were dried over magnesium sulfate, filtered and concentrated. The residue was purified by means of preparative HPLC. The fractions comprising product were combined, the acetonitrile was removed on a rotary evaporator, and the aqueous residue was neutralized with saturated potassium carbonate solution and extracted three times with ethyl acetate. After the combined ethyl acetate phases had been dried over magnesium sulfate, they were filtered and concentrated to dryness. 34 mg of the desired compound were obtained, which was reacted further directly.

LC-MS Rt (B): 0.90 min;
[M+H$^+$]: 311.0 c) 2-((R)-6,8-Dichloro-1,2,3,4-tetrahydroisoquinolin-4-yl)phenylamine

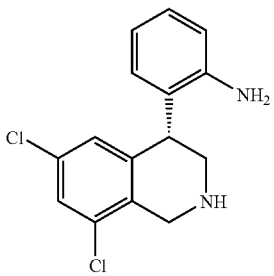

1-(2-Aminophenyl)-2-(2,4-dichlorobenzylamino)ethanol (34 mg) was dissolved in dichloromethane (1 ml) and admixed with ice cooling and stirring with concentrated sulfuric acid. Subsequently, the ice bath was removed and the mixture was stirred at 80° C. for 10 hours while evaporating off the dichloromethane. After cooling, the reaction mixture was admixed with ice-water with ice cooling and alkalized with 10 M sodium hydroxide solution. The aqueous phase was extracted three times with dichloromethane and the combined organic phases were dried over magnesium sulfate, filtered and concentrated. The residue was purified on silica gel. 22 mg of the desired compound were obtained.

LC-MS Rt (B): 0.99 min;
[M+H$^+$]: 293.0 d) 1-[2-((R)-6,8-Dichloro-1,2,3,4-tetrahydroisoquinolin-4-yl)phenyl]pyrrolidine-2,5-dione trifluoroacetic acid salt 2-((R)-6,8-Dichloro-1,2,3,4-tetrahydroisoquinolin-4-yl)phenylamine (22 mg) was heated to 150° C. together with succinic acid (10 mg) and polyphosphoric acid (2 ml) in a closed screwtop test tube for 3 h. For workup, the still-hot reaction mixture was added to ice-water and alkalized with saturated potassium carbonate solution. The aqueous phase was extracted three times with ethyl acetate and the combined organic phases were dried over magnesium sulfate, filtered and concentrated. The residue was purified by means of preparative HPLC. The fractions comprising product were combined, the acetonitrile was removed on a rotary evaporator and the residue was freeze-dried. 7 mg of the title compound were obtained.

LC-MS Rt (B): 1.04 min;
[M+H$^+$]: 375.0

Example 53

3-[2-((R)-6,8-Dichloro-2-cyclopropyl-1,2,3,4-tetrahydroisoquinolin-4-yl)-phenyl]imidazolidine-2,4-dione hydrochloride

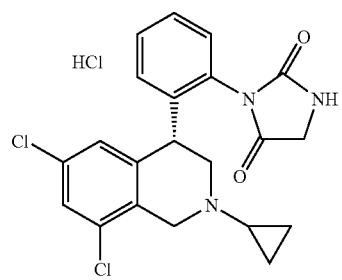

39 mg of the title compound were obtained starting from 2-((R)-6,8-dichloro-2-cyclo-propyl-1,2,3,4-tetrahydroisoquinolin-4-yl)phenylamine (example 41b) and ethyl isocyanatoacetate analogously to example 1.

LC-MS Rt (B): 1.14 min;
[M+H$^+$]: 416.0

Example 54

3-[2-((R)-6,8-Dichloro-2-methyl-1,2,3,4-tetrahydroisoquinolin-4-yl)phenyl]-1-methylimidazolidine-2,4-dione hydrochloride

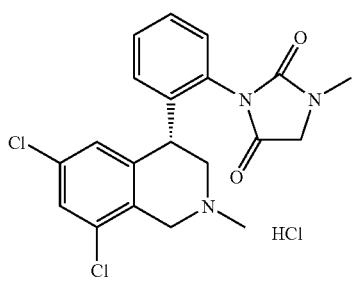

a) 4-Nitrophenyl[2-((R)-6,8-dichloro-2-methyl-1,2,3,4-tetrahydroisoquinolin-4-yl)-phenyl]carbamate

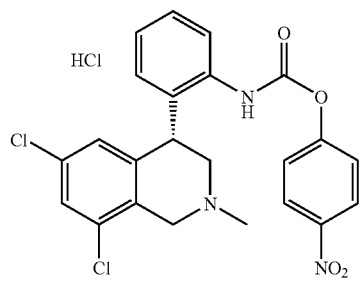

(R)-2-(6,8-Dichloro-2-methyl-1,2,3,4-tetrahydroisoquinolin-4-yl)phenylamine (200 mg, enantiomer B, preparation as described in WO2004085404) was dissolved in absolute dichloromethane (6 ml) and admixed with stirring with 4-nitrophenyl chloroformate (157 mg). After 4 h, a further 0.1 equivalent of 4-nitrophenyl chloroformate was added. After standing overnight, the dichloromethane was removed and the residue was used directly in the next stage.

LC-MS Rt (B): 1.29 min;
[M+H$^+$]: 472.0 b) 3-[2-((R)-6,8-Dichloro-2-methyl-1,2,3,4-tetrahydroisoquinolin-4-yl)phenyl]-1-methyl-imidazolidine-2,4-dione hydrochloride 4-Nitrophenyl[2-((R)-6,8-dichloro-2-methyl-1,2,3,4-tetrahydroisoquinolin-4-yl)phenyl]carbamate (125 mg) was dissolved in absolute THF (5 ml), and sarcosine methyl ester hydrochloride and triethylamine were added dropwise with stirring. After stirring for 5 h, the reaction mixture was freed of the solvent, and the residue was admixed with water and 2 N hydrochloric acid and refluxed for 2 h. After standing overnight, the reaction mixture was concentrated and admixed with ethyl acetate, water and saturated potassium carbonate solution. After separation of the phases, the organic phase was washed five times with saturated potassium carbonate solution and twice with saturated sodium chloride solution. Drying over magnesium sulfate and filtration were followed by concentration. The residue was purified by means of preparative HPLC. The fractions comprising product were combined, the acetonitrile was removed on a rotary evaporator, and the aqueous residue was neutralized with saturated potassium carbonate solution and extracted three times with ethyl acetate. After the combined ethyl acetate phases had been dried over magnesium sulfate, they were filtered and concentrated to dryness. The residue was taken up with water/hydrochloric acid and freeze-dried. 60 mg of the title compound were obtained.

LC-MS Rt (B): 1.02 min;
[M+H$^+$]: 404.0

Example 55

3-[2-((R)-6,8-Dichloro-2-cyclopropyl-1,2,3,4-tetrahydroisoquinolin-4-yl)-phenyl]-1-methylimidazolidine-2,4-dione hydrochloride

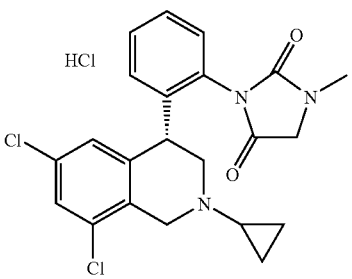

Starting from 2-((R)-6,8-dichloro-2-cyclopropyl-1,2,3,4-tetrahydroisoquinolin-4-yl)-phenylamine (example 41b), the title compound was synthesized analogously to example 54 and 55 mg of the title compound were obtained as the hydrochloride.

LC-MS Rt (B): 1.17 min;
[M+H$^+$]: 430.0

Example 56

3-[2-((R)-6,8-Dichloro-2-methyl-1,2,3,4-tetrahydroisoquinolin-4-yl)phenyl]-5,5-dimethylimidazolidine-2,4-dione hydrochloride

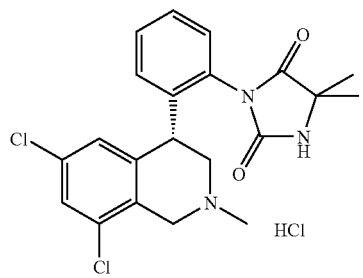

(R)-2-(6,8-Dichloro-2-methyl-1,2,3,4-tetrahydroisoquinolin-4-yl)phenylamine (50 mg, enantiomer B, preparation as described in WO2004085404) was dissolved in absolute dichloromethane (5 ml), and methyl 2-isocyanato-2-methylpropionate was added dropwise with stirring. After being stirred for 3 h and left to stand overnight, the mixture was admixed with water, the phases were separated and the aqueous phase was extracted twice with dichloromethane. The combined organic phases were dried over magnesium sulfate, filtered and concentrated. The residue was purified by means of preparative HPLC. The fractions comprising product were purified, the acetonitrile was removed on a rotary evaporator, and the aqueous residue was neutralized with saturated potassium carbonate solution and extracted three times with ethyl acetate. After the combined ethyl acetate phases had been dried over magnesium sulfate, they were filtered and concentrated to dryness. The residue was dissolved in acetonitrile (1 ml) and admixed with 10% hydrochloric acid. After stirring for 2 h, the mixture was diluted with water (3 ml) and freeze-dried. 68 mg of the title compound were obtained.
LC-MS Rt (B): 1.08 min;
[M+H$^+$]: 418.0

Example 57

(R and S)-3-[2-((R)-6,8-Dichloro-2-methyl-1,2,3,4-tetrahydroisoquinolin-4-yl)phenyl]-5-(2-methylsulfanylethyl)imidazolidine-2,4-dione trifluoroacetic acid salt

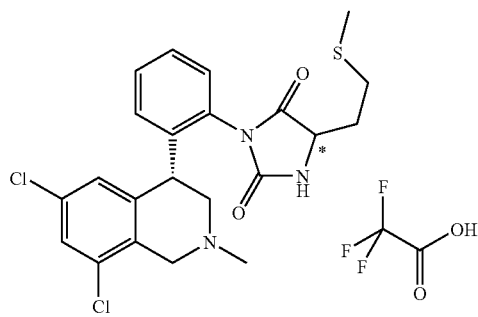

(R)-2-(6,8-Dichloro-2-methyl-1,2,3,4-tetrahydroisoquinolin-4-yl)phenylamine (50 mg, enantiomer B, preparation as described in WO2004085404) was reacted analogously to example 56 with ethyl 2-isocyanato-4-(methylthio)butyrate (33 mg) in methylene chloride, purified and ring-closed. The crude product which was then obtained was purified by means of preparative HPLC and could then be separated into its diastereomers, the more polar P1 and the less polar P2.

P1:
LC-MS Rt (B): 1.11 min;
[M+H$^+$]: 464.0

P2:
LC-MS Rt (B): 1.16 min;
[M+H$^+$]: 464.0

Starting from (R)-2-(6,8-dichloro-2-methyl-1,2,3,4-tetrahydroisoquinolin-4-yl)-phenylamine (enantiomer B, preparation as described in WO2004085404) and the corresponding isocyanates, the following products were obtained as diastereomer mixtures analogously to example 56:

| Example | Structure | Salt | Analogously to example | MS [M + H$^+$] | LC-MS Rt [min] |
|---|---|---|---|---|---|
| 58 | 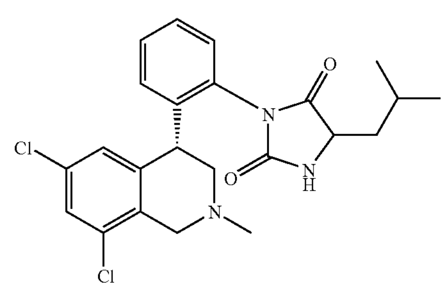 | HCl | 56 | 446.1 (ESI$^+$) | 1.25 (B) |
| 59 | 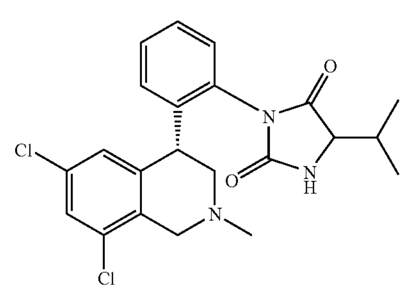 | HCl | 56 | 432.0 (ESI$^+$) | 1.13 and 1.21 (B) |

-continued

| Example | Structure | Salt | Analogously to example | MS [M + H⁺] | LC-MS Rt [min] |
|---|---|---|---|---|---|
| 60 | 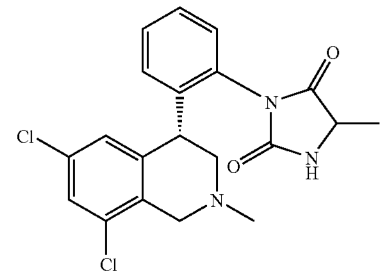 | — | 56 | 404.0 (ESI⁺) | 1.04 and 1.12 (B) |

Example 61

1-[2-((R)-2-Methyl-1,2,3,4-tetrahydroisoquinolin-4-yl)phenyl]pyrrolidine-2,5-dione hydrochloride

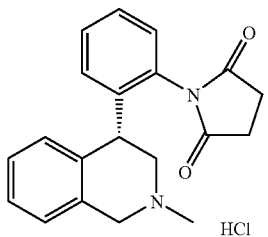

In a hydrogenation apparatus, a spatula-tip of palladium on activated carbon (5%) was added to a solution of 1-[2-((R)-6,8-dichloro-2-methyl-1,2,3,4-tetrahydroisoquinolin-4-yl)phenyl]pyrrolidine-2,5-dione (68 mg, example 7) in methanol (15 ml), and, after application of a hydrogen atmosphere, agitated for 2 h. After the hydrogen had been removed, the apparatus was left to stand under argon overnight, and then the catalyst was filtered off and washed with methanol. The filtrate was concentrated to dryness. 10 mg of the crude product were taken up with water and 10% hydrochloric acid and freeze-dried. 10 mg of the title compound were obtained.

LC-MS Rt (B): 0.87 min;
[M+H⁺]: 312.1

Example 62

1-[2-((R)-6,8-Dichloro-2-methyl-1,2,3,4-tetrahydroisoquinolin-4-yl)phenyl]-3-methyl-1,3-dihydroimidazol-2-one hydrochloride

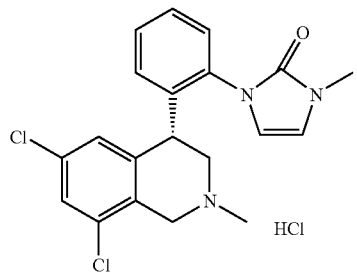

(R)-2-(6,8-Dichloro-2-methyl-1,2,3,4-tetrahydroisoquinolin-4-yl)phenylamine (enantiomer B, preparation as described in WO2004085404), 4-nitrophenyl chloroformate and methylaminoacetaldehyde dimethyl acetal were reacted analogously to example 40, and the resulting intermediate (85 mg) was subsequently cyclized with a mixture of water (1 ml) and 10% hydrochloric acid (3.2 ml). Workup and purification were analogous to example 40. 65 mg of the title compound were isolated.

LC-MS Rt (B): 1.02 min;
[M+H⁺]: 388.0

Example 63

1-[2-(8-Bromo-6-chloro-2-methyl-1,2,3,4-tetrahydroisoquinolin-4-yl)-phenyl]pyrrolidine-2,5-dione hydrochloride

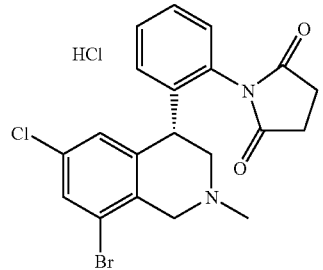

a) 2-Bromo-1-bromomethyl-4-chlorobenzene

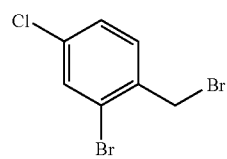

2-Bromo-4-chlorotoluene (5 g) was initially charged in carbon tetrachloride (120 ml), and then AIBN (400 mg) and NBS (4.8 g) were introduced successively with stirring. Subsequently, the reaction mixture was heated under reflux for 6 h and then further NBS (0.6 g) was added at room temperature. After a further 2 h under reflux, the heater was removed and the mixture was left to stand overnight. After the precipitate had been filtered off, the mixture was washed with carbon tetrachloride and then the filtrate was extracted three times with 0.5 N sodium hydrogencarbonate solution, followed by several washes with water until the pH of the wash solution was neutral. The organic phase was dried over magnesium sulfate, filtered and concentrated. After chromatography on silica gel, 3.57 g of the title compound were obtained.

LC-MS Rt (B): 1.85 min;

[M+H$^+$]: 202.6 (Cl$^+$)

b) (2-Bromo-4-chlorobenzyl)methylamine

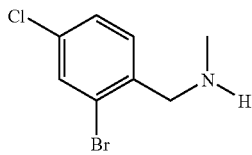

33% ethanolic methylamine solution (13 ml) was initially charged and 2-bromo-1-bromomethyl-4-chlorobenzene (3 g), dissolved in absolute ethanol (20 ml), was added dropwise with stirring within 30 min. After stirring at room temperature for 4 h, the mixture was left to stand overnight. After the solvent had been removed, the residue was taken up with ethyl acetate and extracted once with 1 N hydrochloric acid. The aqueous phase was adjusted to pH 11 with 10 N sodium hydroxide solution and then extracted three times with ethyl acetate. The combined ethyl acetate phases were dried over magnesium sulfate, filtered and concentrated. 1.7 g of the desired compound were obtained.

LC-MS Rt (B): 0.76 min;

[M+H$^+$]: 233.9 c) N-(2-{2-[(2-Bromo-4-chlorobenzyl)methylamino]acetyl}phenyl)acetamide

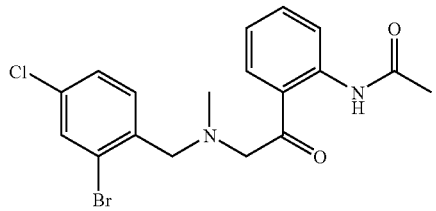

(2-Bromo-4-chlorobenzyl)methylamine (1.7 g) was initially charged in absolute ethanol (5 ml). After addition of sodium hydrogencarbonate (1.2 g), N-[2-(2-bromoacetyl)-phenyl]acetamide (2 g), dissolved in ethanol (80 ml), was added dropwise with stirring. After being stirred at room temperature for 4 h, the mixture stood overnight. For workup, the solvent was removed, the residue was admixed with ethyl acetate/water, the aqueous phase was extracted twice with ethyl acetate and the combined ethyl acetate fractions were subsequently dried over magnesium sulfate, filtered and concentrated. The crude product was purified by means of preparative HPLC. The fractions comprising product were combined, the acetonitrile was removed on a rotary evaporator, and the aqueous residue was neutralized with saturated sodium hydrogencarbonate solution and extracted three times with ethyl acetate. After the combined ethyl acetate phases had been dried over magnesium sulfate, the mixture was filtered and concentrated to dryness. 1.5 g of the desired product were obtained.

LC-MS Rt (B): 1.07 min;

[M+H$^+$]: 409.0 d) N-(2-{2-[(2-Bromo-4-chlorobenzyl)methylamino]-1-hydroxyethyl}phenyl)acetamide

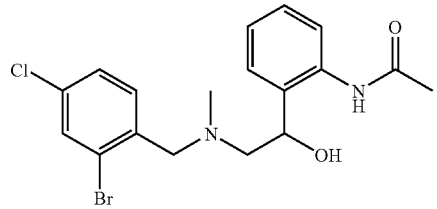

N-(2-{2-[(2-Bromo-4-chlorobenzyl)methylamino]acetyl}phenyl)acetamide (1.5 g) was initially charged in methanol (45 ml) and cooled to 0° C. with an ice bath. After sodium borohydride (266 mg) had been introduced in portions, the mixture was allowed to come to room temperature and then stirred further for 2 h. The solvent was removed and the residue admixed with ethyl acetate/water and extracted three times with ethyl acetate, and the combined organic phases were dried over magnesium sulfate, filtered and concentrated. 1.44 g of the title compound were obtained.

LC-MS Rt (B): 0.94 min;

[M+H$^+$]: 411.0 e) 1-(2-Aminophenyl)-2-[(2-bromo-4-chlorobenzyl)methylamino]ethanol

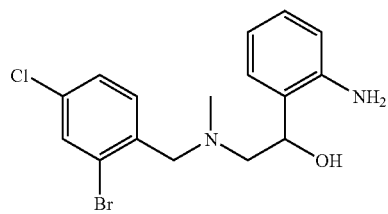

N-(2-{2-[(2-Bromo-4-chlorobenzyl)methylamino]-1-hydroxyethyl}phenyl)acetamide (1.4 g) was dissolved in absolute methanol (50 ml) and admixed with sodium methoxide solution (3.5 ml) and heated to reflux for 8 h. After sodium methoxide solution had been added again (1.5 ml), the mixture was heated to reflux for a further 4 h. The reaction mixture was added to ice-water and extracted three times with ethyl acetate, and the combined organic phases were dried over magnesium sulfate, filtered and concentrated. The residue was purified by means of preparative HPLC. The fractions comprising product were combined, the acetonitrile was removed on a rotary evaporator, and the aqueous residue was neutralized with saturated potassium carbonate solution and extracted three times with ethyl acetate. After the combined ethyl acetate phases had been dried over magnesium sulfate, they were filtered and concentrated to dryness. 801 mg of the title compound were obtained.

LC-MS Rt (B): 0.92 min;

[M+H$^+$]: 369.0 f) 2-(8-Bromo-6-chloro-2-methyl-1,2,3,4-tetrahydroisoquinolin-4-yl)phenylamine

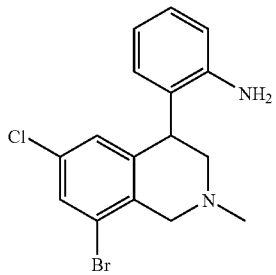

1-(2-Aminophenyl)-2-[(2-bromo-4-chlorobenzyl)methylamino]ethanol (800 mg) was dissolved in dichloromethane (1 ml) and admixed with concentrated sulfuric acid (8 ml) with ice cooling. Subsequently, the mixture was stirred at 60° C. for 7 h. For workup, the reaction mixture was added to ice-water, alkalized with 10 N sodium hydroxide solution and washed three times with ethyl acetate. The combined organic phases were dried over magnesium sulfate, filtered and concentrated. The residue was purified by means of preparative HPLC. The fractions comprising product were combined, the acetonitrile was removed on a rotary evaporator, and the aqueous residue was neutralized with saturated sodium hydrogencarbonate solution and extracted three times with ethyl acetate. After the combined ethyl acetate phases had been dried over magnesium sulfate, they were filtered and concentrated to dryness. 438 mg of the desired compound were obtained.

LC-MS Rt (B): 1.03 min;
[M+H$^+$]: 351.0 g) 1-[2-(8-Bromo-6-chloro-2-methyl-1,2,3,4-tetrahydroisoquinolin-4-yl)phenyl]-pyrrolidine-2,5-dione hydrochloride 2-(8-Bromo-6-chloro-2-methyl-1,2,3,4-tetrahydroisoquinolin-4-yl)phenylamine (60 mg) was admixed with succinic acid (22 mg) and reacted in polyphosphoric acid analogously to example 7. 47 mg of the title compound were obtained.

LC-MS Rt (B): 1.04 min;
[M+H$^+$]: 433.0

Example 64

1-[2-(8-Bromo-6-chloro-2-methyl-1,2,3,4-tetrahydroisoquinolin-4-yl)-phenyl]pyrrolidin-2-one

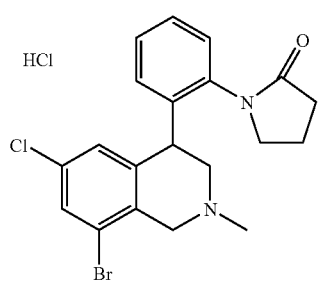

Analogously to example 36, 2-(8-bromo-6-chloro-2-methyl-1,2,3,4-tetrahydroisoquinolin-4-yl)phenylamine (80 mg) was reacted with 4-chlorobutyryl chloride (35 mg) and the resulting amide was subsequently ring-closed with potassium carbonate in DMSO.

LC-MS Rt (B): 1.05 min;
[M+H$^+$]: 419.0

Pharmacological Data:

Test Description:

In this test, the recovery in the intracellular pH (pH$_i$) of LAP1 cells, which stably express the sodium-proton exchanger subtype 3 (NHE3), after an acidification was determined. This recovery sets in even under bicarbonate-free conditions in the case of functioning NHE3. To this end, the pH$_i$ was determined with the pH-sensitive fluorescent dye BCECF (Molecular Probes, Eugene, Oreg., USA; the precursor BCECF-AM is used). The cells were first incubated with BCECF (5 μM BCECF-AM) in NH$_4$Cl buffer (NH$_4$Cl buffer: 115 mM cholineCl, 20 mM NH$_4$Cl, 5 mM KCl, 1 mM CaCl$_2$, 1 mM MgCl$_2$, 20 mM Hepes, 5 mM glucose; a pH of 7.4 is established with 1 M KOH). The intracellular acidification was induced by washing the cells incubated in NH$_4$Cl buffer with NH$_4$Cl-free buffer (133.8 mM choline chloride, 4.7 mM KCl, 1.25 mM CaCl$_2$, 1.25 mM MgCl$_2$, 0.97 mM K$_2$HPO$_4$, 0.23 mM KH$_2$PO$_4$, 5 mM Hepes, 5 mM glucose; a pH of 7.4 is established with 1 M KOH). After the washing operation, 90 μl of the NH$_4$Cl-free buffer were left on the cells. The pH recovery was started by the addition of 90 μl of Na$^+$-containing buffer (133.8 mM NaCl, 4.7 mM KCl, 1.25 mM CaCl$_2$, 1.25 mM MgCl$_2$, 0.97 mM Na$_2$HPO$_4$, 0.23 mM NaH$_2$PO$_4$, 10 mM Hepes, 5 mM glucose; a pH of 7.4 is established with 1 M NaOH) in the analytical instrument (FLIPR, "Fluorometric Imaging Plate Reader", Molecular Devices, Sunnyvale, Calif., USA). The BCECF fluorescence was determined at an excitation wavelength of 498 nm and the FLIPR emission filter 1 (band gap from 510 to 570 nm). The subsequent changes in fluorescence were registered for two minutes as a measure of the pH recovery. For the calculation of the NHE3-inhibitory potential of the tested substances, the cells were tested first in buffers in which full pH recovery, or none at all, took place. For full pH recovery (100%), the cells were incubated in Na$^+$-containing buffer (see above), and Na$^+$-free buffer for the determination of the 0% value (see above). The substances to be tested were made up in Na$^+$-containing buffer. The recovery in the intracellular pH at each tested concentration of a substance was expressed in percent of the maximum recovery. From the percentages of the pH recovery, the IC$_{50}$ value of the particular substance for the NHE3 was calculated by means of the program XLFit (idbs, Surrey, UK).

The inhibitory action (IC$_{50}$ values) of various example compounds on the NHE3 is listed in the table which follows:

| Example | IC$_{50}$ [μM] |
| --- | --- |
| 4 | 0.129 |
| 7 | 0.039 |
| 8 | 2.59 |
| 10 | 0.047 |
| 14 | 0.119 |
| 16 | 0.222 |
| 29 | 1.2 |
| 34 | 29.2 |
| 35 | 0.082 |
| 38 | 0.461 |
| 40 | 0.131 |
| 42 | 0.069 |
| 43 | 0.049 |
| 44 | 0.22 |

-continued

| Example | IC$_{50}$ [μM] |
|---|---|
| 46 | 0.22 |
| 51 | 0.141 |
| 52 | 12.3 |
| 55 | 0.12 |
| 57 | 1.4 |
| 58 | 7.4 |
| 64 | 0.25 |

What is claimed is:

1. A compound of formula I

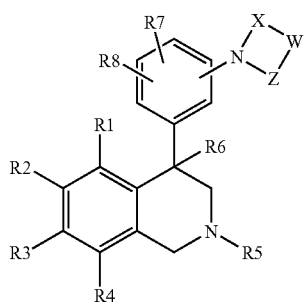

wherein:
R1, R2, R3 and R4
are each independently hydrogen, F, Cl, Br, I, CN, NO$_2$ or R11—(C$_m$H$_{2m}$)—A$_n$—;
m is zero, 1, 2, 3 or 4;
n is zero or 1;
R11 is hydrogen, methyl or C$_p$F$_{2p+1}$;
A is oxygen, NH, N(CH$_3$) or S(O)$_q$;
p is 1, 2 or 3;
q is zero, 1 or 2;
R5 is hydrogen, alkyl having 1, 2, 3, 4, 5 or 6 carbon atoms or cycloalkyl having 3, 4, 5 or 6 carbon atoms;
R6 is hydrogen, OH, F, CF$_3$, alkyl having 1, 2 or 3 or 4 carbon atoms or cycloalkyl having 3, 4, 5 or 6 carbon atoms;
R7 and R8 are each independently hydrogen, F, Cl, Br, CN, CO$_2$R12, NR13R14 or R16—(C$_{mm}$H$_{2mm}$)—B$_{nn}$—;
R12 is hydrogen, alkyl having 1, 2, 3 or 4 carbon atoms or cycloalkyl having 3, 4, 5 or 6 carbon atoms;
R13 and R14 are each independently hydrogen, alkyl having 1, 2, 3 or 4 carbon atoms or cycloalkyl having 3, 4, 5 or 6 carbon atoms; or
R13 and R14, which, including the nitrogen atom to which they are bonded, form a 4-, 5-, 6- or 7-membered ring in which one CH$_2$ group may be replaced by NR15, S or oxygen;
R15 is hydrogen, alkyl having 1, 2, 3 or 4 carbon atoms or cycloalkyl having 3, 4, 5 or 6 carbon atoms;
mm is zero, 1, 2, 3 or 4;
nn is zero or 1;
R16 is hydrogen, methyl or C$_{pp}$F$_{2pp+1}$;
B is oxygen or S(O)$_{qq}$;
pp is 1, 2 or 3;
qq is zero, 1 or 2;
W is C$_r$H$_{2r}$ or C$_s$H$_{2s-2}$; wherein one or more CH$_2$ groups in C$_r$H$_{2r}$ and C$_s$H$_{2s-2}$ may be replaced by NR17, oxygen or S;
R17 is hydrogen, alkyl having 1, 2, 3 or 4 carbon atoms or cycloalkyl having 3, 4, 5 or 6 carbon atoms;
r is 1, 2, 3, 4, 5, 6, 7 or 8;
s is 2, 3, 4, 5, 6, 7 or 8;
X is —C(O)— or —S(O)$_2$—; and
Z is —C(O)— or a bond;
or a pharmaceutically acceptable salt or trifluoroacetate thereof.

2. The compound according to claim 1 wherein
R1, R2, R3 and R4 are each independently hydrogen, F, Cl, Br, CN or R11—(C$_m$H$_{2m}$)—A$_n$—;
m is zero or 1;
n is zero or 1;
R11 is hydrogen, methyl or C$_p$F$_{2p+1}$;
A is oxygen, NCH$_3$ or S(O)$_q$;
p is 1 or 2;
q is zero, 1 or 2;
R5 is hydrogen, methyl, ethyl or cyclopropyl;
R6 is hydrogen or methyl;
R7 and R8 are each independently hydrogen, F, Cl, CN, CO$_2$R12, NR13R14 or R16—(C$_{mm}$H$_{2mm}$)—B$_{nn}$—;
R12 is hydrogen, methyl or ethyl;
R13 and R14 are each independently hydrogen, alkyl having 1, 2, 3 or 4 carbon atoms or cycloalkyl having 3, 4, 5 or 6 carbon atoms; or
R13 and R14, which, including the nitrogen atom to which they are bonded, form a 5-, 6- or 7-membered ring in which one CH$_2$ group may be replaced by NR15, S or oxygen;
R15 is hydrogen, alkyl having 1, 2, 3 or 4 carbon atoms or cycloalkyl having 3, 4, 5 or 6 carbon atoms;
mm is zero, 1 or 2;
nn is zero or 1;
R16 is hydrogen, methyl or C$_{pp}$F$_{2pp+1}$;
B is oxygen or S(O)$_{qq}$;
pp is 1 or 2;
qq is zero, 1 or 2;
W is C$_r$H$_{2r}$ or C$_s$H$_{2s-2}$ wherein one or more CH$_2$ groups in C$_r$H$_{2r}$ and C$_s$H$_{2s-2}$ may be replaced by NR17, oxygen or S;
R17 is selected from the group consisting of hydrogen, an alkyl group having 1, 2, 3 or 4 carbon atoms or cycloalkyl having 3, 4, 5 or 6 carbon atoms;
r is 2, 3, 4, 5, 6, 7 or 8;
s is 2, 3, 4, 5, 6, 7 or 8;
X is —C(O)— or —S(O)$_2$—; and
Z is —C(O)—;
or a pharmaceutically acceptable salt or trifluoroacetate thereof.

3. The compound according to claim 1 wherein
R1 and R3 are each hydrogen;
R2 and R4 are each independently hydrogen, F, Cl, Br, NH$_2$, NHCH$_3$ or N(CH$_3$)$_2$;
R5 is hydrogen, methyl, ethyl or cyclopropyl;
R6 is hydrogen or methyl;
R7 and R8 are each hydrogen;
W is C$_r$H$_{2r}$ or C$_s$H$_{2s-2}$ wherein one or more CH$_2$ groups in C$_r$H$_{2r}$ and C$_s$H$_{2s-2}$ may be replaced by NR17, oxygen or S;
R17 is hydrogen or methyl;
r is 2, 3, 4, 5 or 6;
s is 2, 3, 4, 5 or 6;
X is —C(O)— or —S(O)$_2$—; and
Z is —C(O)—;
or a pharmaceutically acceptable salt or trifluoroacetate thereof.

4. The compound according to claim 1, which is:
1-[2-(8-bromo-6-chloro-2-methyl-1,2,3,4-tetrahydroiso-quinolin-4-yl)phenyl]pyrrolidine-2,5-dione, 3-[2-((R)-6,8-dichloro-2-cyclopropyl-1,2,3,4-tetrahydroisoquinolin-4-yl)phenyl]-1-methylimidazolidine-2,4-dione,
3-[2-((R)-6,8-dichloro-2-methyl-1,2,3,4-tetrahydroisoquinolin-4-yl)phenyl]-1-methyl-imidazolidine-2,4-dione
3-[2-((R)-6,8-dichloro-2-cyclopropyl-1,2,3,4-tetrahydroisoquinolin-4-yl)phenyl]-imidazolidine-2,4-dione
(S)-1-[2-((R)-6,8-dichloro-2-cyclopropyl-1,2,3,4-tetrahydroisochinolin-4-yl)phenyl]-3-hydroxypyrrolidine-2,5-dione,
(R)-1-[2-((R)-6,8-dichloro-2-cyclopropyl-1,2,3,4-tetrahydroisoquinolin-4-yl)phenyl]-3-hydroxypyrrolidine-2,5-dione,
(R)-1-[2-((R)-6,8-dichloro-2-methyl-1,2,3,4-tetrahydroisoquinolin-4-yl)phenyl]-3-hydroxypyrrolidine-2,5-dione,
(S)-1-[2-((R)-6,8-dichloro-2-methyl-1,2,3,4-tetrahydroisoquinolin-4-yl)phenyl]-3-hydroxypyrrolidine-2,5-dione,
4-[2-((R)-6,8-dichloro-2-methyl-1,2,3,4-tetrahydroisoquinolin-4-yl)phenyl]morpholine-3,5-dione,
3-[2-((R)-6,8-dichloro-2-methyl-1,2,3,4-tetrahydroisoquinolin-4-yl)phenyl]oxazolidine-2,4-dione,
3-[2-((R)-6,8-dichloro-2-methyl-1,2,3,4-tetrahydroisoquinolin-4-yl)phenyl]thiazolidine-2,4-dione,
1-[2-((R)-6,8-dichloro-2-cyclopropyl-1,2,3,4-tetrahydroisoquinolin-4-yl)phenyl]-pyrrolidine-2,5-dione,
(S)-1-[2-((R)-6,8-dichloro-2-methyl-1,2,3,4-tetrahydroisoquinolin-4-yl)phenyl]-3-methyl-piperidine-2,6-dione,
(R)-1-[2-((R)-6,8-dichloro-2-methyl-1,2,3,4-tetrahydroisoquinolin-4-yl)phenyl]-3-methyl-piperidine-2,6-dione,
1-[2-((R)-6,8-dichloro-2-methyl-1,2,3,4-tetrahydroisoquinolin-4-yl)phenyl]-3,5-dimethyl-piperidine-2,6-dione,
1-[2-((R)-6,8-dichloro-2-methyl-1,2,3,4-tetrahydroisoquinolin-4-yl)phenyl]-3-methyl-pyrrolidine-2,5-dione,
1-[2-((R)-6,8-dichloro-2-methyl-1,2,3,4-tetrahydroisoquinolin-4-yl)phenyl]-3,3-dimethyl-pyrrolidine-2,5-dione,
1-[2-(6,8-dichloro-2-cyclopropyl-1,2,3,4-tetrahydroisoquinolin-4-yl)phenyl]pyrrolidine-2,5-dione,
1-[4-((S)-6,8-dichloro-2-methyl-1,2,3,4-tetrahydroisoquinolin-4-yl)phenyl]piperidine-2,6-dione,
1-[4-((S)-6,8-dichloro-2-methyl-1,2,3,4-tetrahydroisoquinolin-4-yl)phenyl]pyrrolidine-2,5-dione,
1-[4-(6,8-dichloro-2-methyl-1,2,3,4-tetrahydroisoquinolin-4-yl)phenyl]pyrrolidine-2,5-dione,
1-[2-((R)-6,8-dichloro-2-methyl-1,2,3,4-tetrahydroisoquinolin-4-yl)phenyl]piperidine-2,6-dione,
1-[2-(6,8-dichloro-2-methyl-1,2,3,4-tetrahydroisoquinolin-4-yl)phenyl]piperidine-2,6-dione,
1-[3-((S)-6,8-dichloro-2-methyl-1,2,3,4-tetrahydroisoquinolin-4-yl)phenyl]pyrrole-2,5-dione,
1-[2-(6,8-dichloro-2-methyl-1,2,3,4-tetrahydroisoquinolin-4-yl)phenyl]pyrrolidine-2,5-dione,
1-[2-((R)-6,8-dichloro-2-methyl-1,2,3,4-tetrahydroisoquinolin-4-yl)phenyl]pyrrolidine-2,5-dione,
3-[2-((R)-6,8-dichloro-2-methyl-1,2,3,4-tetrahydroisoquinolin-4-yl)phenyl]imidazolidine-2,4-dione,
3-[2-(6,8-dichloro-2-methyl-1,2,3,4-tetrahydroisoquinolin-4-yl)phenyl]imidazolidine-2,4-dione,
3-[3-((S)-6,8-dichloro-2-methyl-1,2,3,4-tetrahydroisoquinolin-4-yl)phenyl]imidazolidine-2,4-dione,
3-[4-((S)-6,8-dichloro-2-methyl-1,2,3,4-tetrahydroisoquinolin-4-yl)phenyl]imidazolidine-2,4-dione,
3-[4-(6,8-dichloro-2-methyl-1,2,3,4-tetrahydroisoquinolin-4-yl)phenyl]imidazolidine-2,4-dione,
3-[2-((R)-6,8-dichloro-2-cyclopropyl-1,2,3,4-tetrahydroisoquinolin-4-yl)phenyl]-oxazolidine-2,4-dione,
3-[2-((R)-6,8-dichloro-2-methyl-1,2,3,4-tetrahydroisoquinolin-4-yl)phenyl]-5-methyl-imidazolidine-2,4-dione,
(3R,4S)-1-[2-((R)-6,8-dichloro-2-methyl-1,2,3,4-tetrahydroisoquinolin-4-yl)phenyl]-3,4-dimethylpyrrolidine-2,5-dione,
1-[4-((S)-6,8-dichloro-2-methyl-1,2,3,4-tetrahydroisoquinolin-4-yl)phenyl]-pyrrole-2,5-dione,
1-[3-((S)-6,8-dichloro-2-methyl-1,2,3,4-tetrahydroisoquinolin-4-yl)phenyl]piperidine-2,6-dione,
1-[3-((S)-6,8-dichloro-2-methyl-1,2,3,4-tetrahydroisoquinolin-4-yl)phenyl]pyrrolidine-2,5-dione,
1-[4-(6,8-dichloro-2-methyl-1,2,3,4-tetrahydroisoquinolin-4-yl)phenyl]piperidine-2,6-dione,
3-[3-(6,8-dichloro-2-methyl-1,2,3,4-tetrahydroisoquinolin-4-yl)phenyl]imidazolidine-2,4-dione,
1-[2-((R)-2-methyl-1,2,3,4-tetrahydroisoquinolin-4-yl)phenyl]pyrrolidine-2,5-dione,
3-[2-((R)-6,8-dichloro-2-methyl-1,2,3,4-tetrahydroisoquinolin-4-yl)phenyl]-5-isopropyl-imidazolidine-2,4-dione,
3-[2-((R)-6,8-dichloro-2-methyl-1,2,3,4-tetrahydroisoquinolin-4-yl)phenyl]-5-isobutyl-imidazolidine-2,4-dione,
(R and S)-3-[2-((R)-6,8-dichloro-2-methyl-1,2,3,4-tetrahydroisoquinolin-4-yl)phenyl]-5-(2-methylsulfanylethyl)imidazolidine-2,4-dione,
3-[2-((R)-6,8-dichloro-2-methyl-1,2,3,4-tetrahydroisoquinolin-4-yl)phenyl]-5,5-dimethyl-imidazolidine-2,4-dione,
1-[2-((R)-6,8-dichloro-1,2,3,4-tetrahydroisoquinolin-4-yl)phenyl]pyrrolidine-2,5-dione,
3-[2-((R)-6,8-dichloro-2-cyclopropyl-1,2,3,4-tetrahydroisoquinolin-4-yl)phenyl]-thiazolidine-2,4-dione,
1-[2-((S)-6,8-dichloro-2-methyl-1,2,3,4-tetrahydroisoquinolin-4-yl)phenyl]pyrrolidine-2,5-dione,
1-[2-((S)-6,8-dichloro-2-cyclopropyl-1,2,3,4-tetrahydroisoquinolin-4-yl)-phenyl]-pyrrolidine-2,5-dione,
1-[2-((R)-6,8-dichloro-2-methyl-1,2,3,4-tetrahydroisoquinolin-4-yl)phenyl]-3,3,4,4-tetra-methylpyrrolidine-2,5-dione,
(S)-1-[2-((R)-6,8-dichloro-2-cyclopropyl-1,2,3,4-tetrahydroisoquinolin-4-yl)phenyl]-3-methylpiperidine-2,6-dione,
1-[4-(6,8-dichloro-2-methyl-1,2,3,4-tetrahydroisoquinolin-4-yl)phenyl]-4,4-dimethyl-piperidine-2,6-dione or
1-[2-(6,8-dichloro-2-methyl-1,2,3,4-tetrahydroisoquinolin-4-yl)phenyl]pyrrole-2,5-dione, or a pharmaceutically acceptable salt or trifluoroacetate thereof.

5. The compound according to claim 1, which is:
1-[2-(8-bromo-6-chloro-2-methyl-1,2,3,4-tetrahydroisoquinolin-4-yl)phenyl]pyrrolidine-2,5-dione,
3-[2-((R)-6,8-dichloro-2-cyclopropyl-1,2,3,4-tetrahydroisochinolin-4-yl)phenyl]-1-methyl-imidazolidine-2,4-dione,
3-[2-((R)-6,8-dichloro-2-methyl-1,2,3,4-tetrahydroisoquinolin-4-yl)phenyl]-1-methyl-imidazolidine-2,4-dione
3-[2-((R)-6,8-dichloro-2-cyclopropyl-1,2,3,4-tetrahydroisoquinolin-4-yl)phenyl]-imidazolidine-2,4-dione (S)-1-[2-((R)-6,8-dichloro-2-cyclopropyl-1,2,3,4-tetrahydroisoquinolin-4-yl)phenyl]-3-hydroxypyrrolidine-2,5-dione,
(R)-1-[2-((R)-6,8-dichloro-2-cyclopropyl-1,2,3,4-tetrahydroisoquinolin-4-yl)phenyl]-3-hydroxypyrrolidine-2,5-dione,
(R)-1-[2-((R)-6,8-dichloro-2-methyl-1,2,3,4-tetrahydroisoquinolin-4-yl)phenyl]-3-hydroxypyrrolidine-2,5-dione,
(S)-1-[2-((R)-6,8-dichloro-2-methyl-1,2,3,4-tetrahydroisoquinolin-4-yl)phenyl]-3-hydroxypyrrolidin-2,5-dione,
4-[2-((R)-6,8-dichloro-2-methyl-1,2,3,4-tetrahydroisoquinolin-4-yl)phenyl]morpholine-3,5-dione,
3-[2-((R)-6,8-dichloro-2-methyl-1,2,3,4-tetrahydroisoquinolin-4-yl)phenyl]oxazolidine-2,4-dione,
3-[2-((R)-6,8-dichloro-2-methyl-1,2,3,4-tetrahydroisoquinolin-4-yl)phenyl]thiazolidine-2,4-dione,
1-[2-((R)-6,8-dichloro-2-cyclopropyl-1,2,3,4-tetrahydroisoquinolin-4-yl)phenyl]-pyrrolidine-2,5-dione,
(S)-1-[2-((R)-6,8-dichloro-2-methyl-1,2,3,4-tetrahydroisoquinolin-4-yl)phenyl]-3-methyl-piperidine-2,6-dione,
(R)-1-[2-((R)-6,8-dichloro-2-methyl-1,2,3,4-tetrahydroisoquinolin-4-yl)phenyl]-3-methyl-piperidine-2,6-dione,
1-[2-((R)-6,8-dichloro-2-methyl-1,2,3,4-tetrahydroisoquinolin-4-yl)phenyl]-3,5-dimethyl-piperidine-2,6-dione,
1-[2-((R)-6,8-dichloro-2-methyl-1,2,3,4-tetrahydroisoquinolin-4-yl)phenyl]-3-methyl-pyrrolidine-2,5-dione,
1-[2-((R)-6,8-dichloro-2-methyl-1,2,3,4-tetrahydroisoquinolin-4-yl)phenyl]-3,3-dimethyl-pyrrolidine-2,5-dione,
1-[2-(6,8-dichloro-2-cyclopropyl-1,2,3,4-tetrahydroisoquinolin-4-yl)phenyl]pyrrolidine-2,5-dione,
1-[4-((S)-6,8-dichloro-2-methyl-1,2,3,4-tetrahydroisoquinolin-4-yl)phenyl]piperidine-2,6-dione,
1-[4-((S)-6,8-dichloro-2-methyl-1,2,3,4-tetrahydroisoquinolin-4-yl)phenyl]pyrrolidine-2,5-dione,
1-[4-(6,8-dichloro-2-methyl-1,2,3,4-tetrahydroisoquinolin-4-yl)phenyl]pyrrolidine-2,5-dione,
1-[2-((R)-6,8-dichloro-2-methyl-1,2,3,4-tetrahydroisoquinolin-4-yl)phenyl]piperidine-2,6-dione,
1-[2-(6,8-dichloro-2-methyl-1,2,3,4-tetrahydroisoquinolin-4-yl)phenyl]piperidine-2,6-dione,
1-[3-((S)-6,8-dichloro-2-methyl-1,2,3,4-tetrahydroisoquinolin-4-yl)phenyl]pyrrole-2,5-dione,
1-[2-(6,8-dichloro-2-methyl-1,2,3,4-tetrahydroisoquinolin-4-yl)phenyl]pyrrolidine-2,5-dione,
1-[2-((R)-6,8-dichloro-2-methyl-1,2,3,4-tetrahydroisoquinolin-4-yl)phenyl]pyrrolidine-2,5-dione,
3-[2-((R)-6,8-dichloro-2-methyl-1,2,3,4-tetrahydroisoquinolin-4-yl)phenyl]imidazolidine-2,4-dione,
3-[2-(6,8-dichloro-2-methyl-1,2,3,4-tetrahydroisoquinolin-4-yl)phenyl]imidazolidine-2,4-dione,
3-[3-((S)-6,8-dichloro-2-methyl-1,2,3,4-tetrahydroisoquinolin-4-yl)phenyl]imidazolidine-2,4-dione,
3-[4-((S)-6,8-dichloro-2-methyl-1,2,3,4-tetrahydroisoquinolin-4-yl)phenyl]imidazolidine-2,4-dione,
3-[4-(6,8-dichloro-2-methyl-1,2,3,4-tetrahydroisoquinolin-4-yl)phenyl]imidazolidine-2,4-dione or
3-[2-((R)-6,8-dichloro-2-cyclopropyl-1,2,3,4-tetrahydroisoquinolin-4-yl)phenyl]-oxazolidine-2,4-dione,
or a pharmaceutically acceptable salt or trifluoroacetate thereof.

6. The compound according to claim 1, wherein
R1, R2, R3 and R4 are each independently F, Cl, Br, CN or R11—$(C_mH_{2m})$—$A_n$—;
m is zero or 1;
n is zero or 1;
R11 is hydrogen, methyl or $C_pF_{2p+1}$;
A is oxygen, $NCH_3$ or $S(O)_q$;
p is 1 or 2;
q is zero, 1 or 2;
R5 is hydrogen, methyl, ethyl or cyclopropyl;
R6 is hydrogen or methyl;
R7 and R8 are each independently hydrogen, F, Cl, CN, $CO_2R12$, NR13R14 or R16—$(C_{mm}H_{2mm})$—$B_{nn}$—;
R12 is hydrogen, methyl or ethyl;
R13 and R14 are each independently hydrogen, alkyl having 1, 2, 3 or 4 carbon atoms or cycloalkyl having 3, 4, 5 or 6 carbon atoms; or
R13 and R14 including the nitrogen atom to which they are bonded, form a 5-, 6- or 7-membered ring in which one $CH_2$ group may be replaced by NR15, S or oxygen;
R15 is hydrogen, alkyl having 1, 2, 3 or 4 carbon atoms or cycloalkyl having 3, 4, 5 or 6 carbon atoms;
mm is zero, 1 or 2;
nn is zero or 1;
R16 is hydrogen, methyl or $C_{pp}F_{2pp+1}$;
B is oxygen or $S(O)_{qq}$;
pp is 1 or 2;
qq is zero, 1 or 2;
W is $C_rH_{2r}$ or $C_sH_{2s-2}$, where one or more $CH_2$ groups in $C_rH_{2r}$ and $C_sH_{2s-2}$ may be replaced by NR17, oxygen or S;
R17 is hydrogen, alkyl having 1, 2, 3 or 4 carbon atoms or cycloalkyl having 3, 4, 5 or 6 carbon atoms;
r is 1, 2, 3, 4, 5, 6, 7 or 8;
s is 2, 3, 4, 5, 6, 7 or 8;
X is —C(O)— or —S(O)$_2$—; and
Z is a bond;
or a pharmaceutically acceptable salt or trifluoroacetate thereof.

7. The compound according to claim 1 wherein:
R1 and R3 are each hydrogen;
R2 and R4 are each independently hydrogen, F, Cl, Br, $NH_2$, $NHCH_3$ or $N(CH_3)_2$;
R5 is hydrogen, methyl, ethyl or cyclopropyl;
R6 is hydrogen or methyl;
R7 and R8 are each hydrogen;
W is $C_rH_{2r}$ or $C_sH_{2s-2}$ where one or more $CH_2$ groups in $C_rH_{2r}$ and $C_sH_{2s-2}$ may be replaced by NR17, oxygen or S;
R17 is hydrogen or methyl;
r is 1, 2, 3, 4, 5 or 6;
s is 2, 3, 4, 5 or 6;
X is —C(O)— or —S(O)$_2$—; and
Z is a bond;
or a pharmaceutically acceptable salt or trifluoroacetate thereof.

8. The compound of formula I as recited in claim 1, which is:
1-[2-(8-bromo-6-chloro-2-methyl-1,2,3,4-tetrahydroisoquinolin-4-yl)phenyl]pyrrolidin-2-one,
1-[2-((R)-6,8-dichloro-2-methyl-1,2,3,4-tetrahydroisoquinolin-4-yl)phenyl]-3-methyl-1,3-dihydroimidazol-2-one,
(R)-6,8-dichloro-4-[2-(1,1-dioxo-1-$\lambda^6$-isothiazolidin-2-yl)phenyl]-2-methyl-1,2,3,4-tetra-hydroisoquinoline, 3-[2-((R)-6,8-dichloro-2-methyl-1,2,3,4-tetrahydroiso-quinolin-4-yl)phenyl]oxazolidin-2-one,
1-[2-((R)-6,8-dichloro-2-methyl-1,2,3,4-tetrahydroiso-quinolin-4-yl)phenyl]-1,3-dihydro-imidazol-2-one,
1-[2-((R)-6,8-dichloro-2-methyl-1,2,3,4-tetrahydroiso-quinolin-4-yl)phenyl]imidazolidin-2-one,
1-[2-((R)-6,8-dichloro-2-methyl-1,2,3,4-tetrahydroiso-quinolin-4-yl)phenyl]pyrrolidin-2-one,
1-[2-((R)-6,8-dichloro-2-methyl-1,2,3,4-tetrahydroiso-quinolin-4-yl)phenyl]pyrrolidin-2-one,
1-[3-((S)-6,8-dichloro-2-methyl-1,2,3,4-tetrahydroiso-quinolin-4-yl)phenyl]piperidin-2-one,
1-[2-((R)-6,8-dichloro-2-cyclopropyl-1,2,3,4-tetrahy-droisoquinolin-4-yl)phenyl]-pyrrolidin-2-one,
3-[2-((R)-6,8-dichloro-2-cyclopropyl-1,2,3,4-tetrahy-droisoquinolin-4-yl)phenyl]-oxazolidin-2-one, or
6,8-dichloro-4-[4-(1,1-dioxo-1-$\lambda^6$-[1,2,5]thiadiazolidin-2-yl)phenyl]-2-methyl-1,2,3,4-tetrahydroisoquino-lines, or a pharmaceutically acceptable salt and trifluoroacetate thereof.

9. The compound according to claim 1, which is:
1-[2-(8-bromo-6-chloro-2-methyl-1,2,3,4-tetrahydroiso-quinolin-4-yl)phenyl]pyrrolidin-2-one,
1-[2-((R)-6,8-dichloro-2-methyl-1,2,3,4-tetrahydroiso-quinolin-4-yl)phenyl]-3-methyl-1,3-dihydroimidazol-2-one,
(R)-6,8-dichloro-4-[2-(1,1-dioxo-1-$\lambda^6$-isothiazolidin-2-yl)phenyl]-2-methyl-1,2,3,4-tetra-hydroisoquinoline,
3-[2-((R)-6,8-dichloro-2-methyl-1,2,3,4-tetrahydroiso-quinolin-4-yl)phenyl]oxazolidin-2-one,
1-[2-((R)-6,8-dichloro-2-methyl-1,2,3,4-tetrahydroiso-quinolin-4-yl)phenyl]-1,3-dihydro-imidazol-2-one,
1-[2-((R)-6,8-dichloro-2-methyl-1,2,3,4-tetrahy-droisochinolin-4-yl)phenyl]imidazolidin-2-one,
1-[2-((R)-6,8-dichloro-2-methyl-1,2,3,4-tetrahydroiso-quinolin-4-yl)phenyl]pyrrolidin-2-one or
1-[2-((R)-6,8-dichloro-2-methyl-1,2,3,4-tetrahydroiso-quinolin-4-yl)phenyl]pyrrolidin-2-one, or a pharmaceutically acceptable salt or trifluoroacetate thereof.

10. A pharmaceutical composition comprising the compound according to claim 1 or a pharmaceutically acceptable salt thereof in combination with pharmaceutically acceptable carrier or excipient.

* * * * *